(12) United States Patent
Maahs et al.

(10) Patent No.: US 8,992,420 B2
(45) Date of Patent: Mar. 31, 2015

(54) METHODS AND APPARATUS FOR OFF-AXIS VISUALIZATION

(75) Inventors: Tracy D. Maahs, Yorba Linda, CA (US);
Richard C. Ewers, Fullerton, CA (US);
Arvin T. Chang, West Covina, CA (US);
Chris Rothe, San Jose, CA (US);
Eugene C. Chen, Carlsbad, CA (US);
Marvin C. Elmer, Rancho Santa Margarita, CA (US); Gilbert Madrid, Dana Point, CA (US); Kabir Gambhir, Encinitas, CA (US)

(73) Assignee: USGI Medical, Inc., San Clemente, CA (US)

(*) Notice: Subject to any disclaimer, the term of this patent is extended or adjusted under 35 U.S.C. 154(b) by 146 days.

(21) Appl. No.: 13/597,072

(22) Filed: Aug. 28, 2012

(65) Prior Publication Data

US 2013/0041214 A1    Feb. 14, 2013

Related U.S. Application Data

(63) Continuation-in-part of application No. 11/129,513, filed on May 13, 2005, now abandoned, which is a continuation-in-part of application No. 10/824,936, filed on Apr. 14, 2004, now Pat. No. 8,512,229.

(60) Provisional application No. 60/670,426, filed on Apr. 11, 2005.

(51) Int. Cl.
*A61B 1/00* (2006.01)
*A61B 1/005* (2006.01)
*A61B 1/018* (2006.01)
*A61B 1/05* (2006.01)

(52) U.S. Cl.
CPC ........... *A61B 1/0051* (2013.01); *A61B 1/00179* (2013.01); *A61B 1/00183* (2013.01); *A61B 1/018* (2013.01); *A61B 1/05* (2013.01); *A61B 1/00085* (2013.01); *A61B 1/00089* (2013.01); *A61B 1/00098* (2013.01)
USPC ........................... 600/114; 600/160; 600/170

(58) Field of Classification Search
USPC ......... 600/104, 103, 106–107, 137, 139, 160, 600/170, 172, 173, 129, 114
See application file for complete search history.

(56) References Cited

U.S. PATENT DOCUMENTS

| 4,245,624 | A | * | 1/1981 | Komiya | 600/106 |
| 4,763,662 | A | * | 8/1988 | Yokoi | 600/461 |
| 5,853,368 | A | * | 12/1998 | Solomon et al. | 600/439 |
| 7,591,781 | B2 | * | 9/2009 | Hirata | 600/114 |

(Continued)

*Primary Examiner* — John P Leubecker
*Assistant Examiner* — Arnaldo Torres Diaz
(74) *Attorney, Agent, or Firm* — Kenneth H. Ohriner; Perkins Coie LLP

(57) ABSTRACT

Methods and apparatus for off-axis visualization are described herein. An endoluminal tissue manipulation assembly is disclosed which provides for a stable endoluminal platform and which also provides for effective triangulation of tools. Such an apparatus may comprise an optionally shape-lockable elongate body defining a longitudinal axis and adapted for endoluminal advancement in a patient body, at least one articulatable visualization lumen disposed near or at a distal region of the elongate body, the at least one articulating visualization lumen being adapted to articulate off-axis relative to a longitudinal axis of the elongate body, and at least one articulatable tool arm member disposed near or at the distal region of the elongate body, the at least one articulatable tool arm member being adapted to articulate off-axis and manipulate a tissue region of interest.

18 Claims, 45 Drawing Sheets

(56) References Cited

U.S. PATENT DOCUMENTS

| | | | |
|---|---|---|---|
| 7,654,951 B2* | 2/2010 | Ishikawa | 600/114 |
| 7,662,089 B2* | 2/2010 | Okada et al. | 600/113 |
| 8,277,373 B2* | 10/2012 | Maahs et al. | 600/107 |
| 8,562,513 B2* | 10/2013 | Yamatani | 600/106 |
| 2004/0147958 A1 | 7/2004 | Lam et al. | |
| 2004/0249367 A1* | 12/2004 | Saadat et al. | 606/1 |
| 2005/0038317 A1* | 2/2005 | Ratnakar | 600/101 |
| 2005/0049455 A1* | 3/2005 | Ootawara et al. | 600/107 |
| 2005/0090709 A1* | 4/2005 | Okada et al. | 600/104 |
| 2005/0234294 A1 | 10/2005 | Saadat et al. | |
| 2005/0234296 A1 | 10/2005 | Saadat et al. | |
| 2005/0251176 A1 | 11/2005 | Swanstrom et al. | |
| 2007/0293727 A1* | 12/2007 | Goldfarb et al. | 600/178 |

* cited by examiner

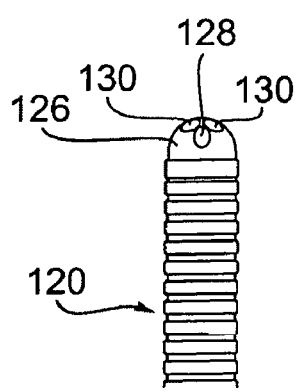
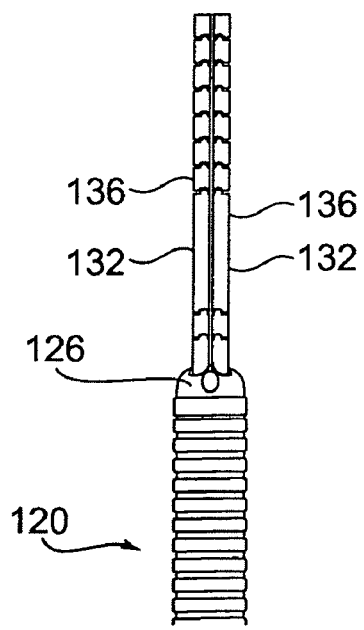
FIG. 13A  FIG. 13B
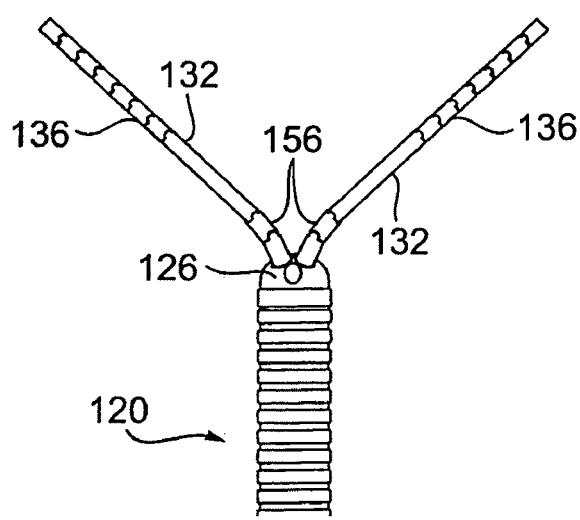
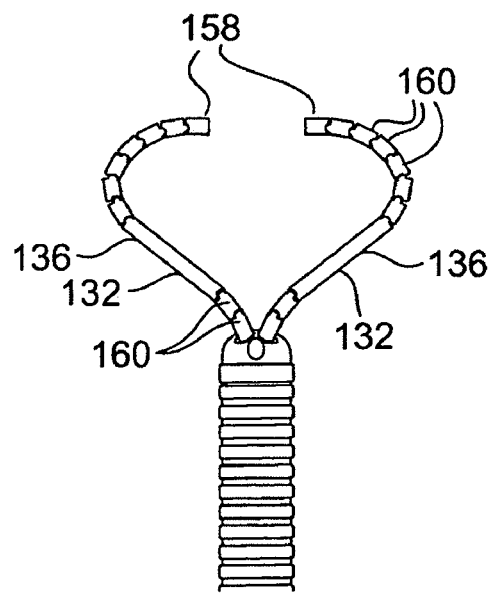
FIG. 13C  FIG. 13D

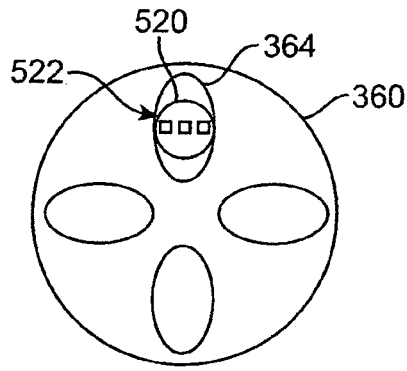
FIG. 45A
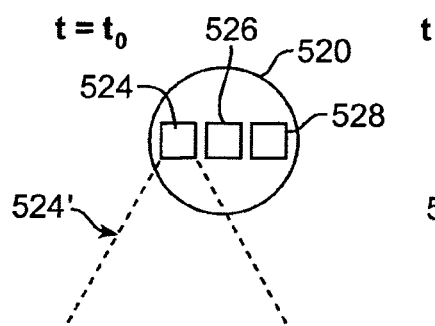 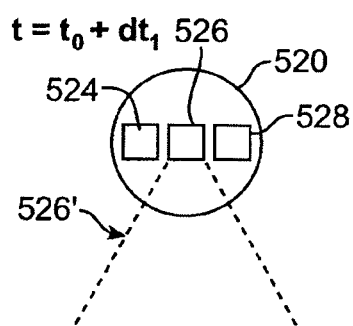 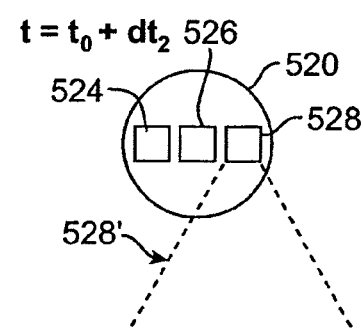
FIG. 45B  FIG. 45C  FIG. 45D
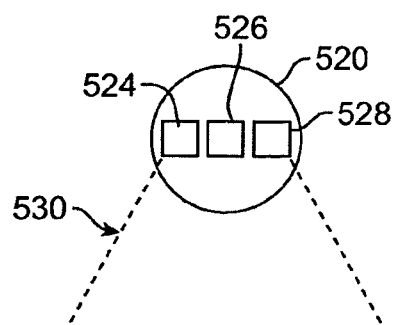
FIG. 45E

METHODS AND APPARATUS FOR OFF-AXIS VISUALIZATION

CROSS-REFERENCES TO RELATED APPLICATIONS

This application is a Continuation of U.S. patent application Ser. No. 11/365,088, filed Feb. 28, 2006, and now pending, which is a continuation-in-part of U.S. patent application Ser. No. 11/129,513 filed May 13, 2005 and now abandoned. U.S. patent application Ser. No. 11/129,513 is a continuation-in-part of U.S. patent application Ser. No. 10/824,936 filed Apr. 14, 2004, now pending, and also claims priority to U.S. Provisional Patent Application No. 60/670,426 filed Apr. 11, 2005. Each of these applications is incorporated herein by reference.

BACKGROUND OF THE INVENTION

Field of the Invention

The present invention relates to methods and apparatus for performing endoluminal procedures within a body lumen. More particularly, the present invention relates to methods and apparatus for visualizing and/or performing procedures endoluminally within a body lumen utilizing off-axis articulation and/or visualization.

Medical endoscopy entails the insertion of an elongate body into a body lumen, conduit, organ, orifice, passageway, etc. The elongate body typically has a longitudinal or working axis and a distal region, and a visualization element disposed near the distal region in-line with the working axis. The visualization element may comprise an optical fiber that extends through the elongate body, or a video chip having an imaging sensor, the video chip coupled to or including a signal-processing unit that converts signals obtained by the imaging sensor into an image. The elongate body may also include a working lumen to facilitate passage of diagnostic or therapeutic tools therethrough, or for injection of fluids or to draw suction.

The maximum delivery profile for a medical endoscope may be limited by the cross-sectional profile of the body lumen, conduit, organ, orifice, passageway, etc., in which the endoscope is disposed. At the same time, advances in therapeutic endoscopy have led to an increase in the complexity of operations attempted with endoscopes, as well as the complexity of tools advanced through the working lumens of endoscopes. As tool complexity has increased, a need has arisen in the art for endoscopes having relatively small delivery profiles that allow access through small body lumens, but that have relatively large working lumens that enable passage of complex diagnostic or therapeutic tools. Furthermore, as the complexity of operations attempted with endoscopes has increased, there has arisen a need for enhanced visualization platforms, including three-dimensional or stereoscopic visualization platforms.

As with endoscopy, ever more challenging procedures are being conducted utilizing laparoscopic techniques. Due to, among other factors, the profile of instruments necessary to perform these procedures, as well as a need to provide both visualization and therapeutic instruments, laparoscopic procedures commonly require multiple ports to obtain the necessary access. Multiple ports also may be required due to the limited surgical space accessible with current, substantially rigid straight-line laparoscopic instruments.

Moreover, conventional endoscopes and instruments provide generally inadequate platforms to perform complex surgeries within patient bodies. The flexible nature of conventional endoscopes and the structural weakness and functional limitations of the instruments passed through small channels within the endoscopes make vigorous tissue manipulation and organ retraction extremely difficult.

Instruments pushed distally through a retroflexed gastroscope, for example, simply push the unsupported endoscope away from the target tissue. As the instrument is further advanced against the tissue surface, the endoscope is typically flexed or pushed away from the tissue region due to a lack of structural rigidity or stability inherent in conventional endoscopes.

Endoscopic surgery is further limited by the lack of effective triangulation due in part to a 2-dimensional visual field typically provided by an endoscope which limits depth perception within the body lumen. Moreover, conventional endoscopic procedures are generally limited to instruments which allow only for co-axial force exertion along a longitudinal axis of the endoscope and instruments which have an inability to work outside of the endoscopic axis.

In view of the foregoing, it would be desirable to provide methods and apparatus for performing endoluminal procedures that facilitate introduction of the apparatus into relatively small body lumens, while providing for introduction of at least one relatively large tool, as compared to standard endoscopes or laparoscopes. It also would be desirable to provide methods and apparatus that facilitate single port laparoscopy.

BRIEF SUMMARY OF THE INVENTION

The endoluminal tissue treatment assembly described herein may comprise, in part, a flexible and elongate body which may utilize a plurality of locking links which enable the elongate body to transition between a flexible state and a rigidized or shape-locked configuration. Details of such a shape-lockable body may be seen in further detail in U.S. Pat. Nos. 6,783,491; 6,790,173; and 6,837,847, each of which is incorporated herein by reference in its entirety.

Additionally, the elongate body may also incorporate additional features that may enable any number of therapeutic procedures to be performed endoluminally. An elongate body may be accordingly sized to be introduced per-orally. However, the elongate body may also be configured in any number of sizes, for instance, for advancement within and for procedures in the lower gastrointestinal tract, such as the colon.

The assembly, in one variation, may have several separate controllable bending sections along its length to enable any number of configurations for the elongate body. For instance, in one variation, elongate body may further comprise a bending section located distal of the elongate body; the bending section may be configured to bend in a controlled manner within a first and/or second plane relative to the elongate body. In yet another variation, the elongate body may further comprise another bending section located distal of the first bending section. In this variation, the bending section may be configured to articulate in multiple planes, e.g., 4-way articulation, relative to the first bending section and elongate body. In a further variation, a third bending section may also be utilized along the length of the device.

In yet another variation, each of the bending sections and the elongate body may be configured to lock or shape-lock its configuration into a rigid set shape once the articulation has been desirably configured. An example of such an apparatus having multiple bending sections which may be selectively rigidized between a flexible configuration and a shape-locked configuration may be seen in further detail in U.S. Pat. Pubs.

2004/0138525 A1; 2004/0138529 A1; 2004/0249367 A1; and 2005/0065397 A1, each of which is incorporated herein by reference in its entirety.

As the bending sections may be articulated in any number of configurations via control wires routed through the elongate body, the assembly may be actively steered to reach all areas of the stomach, including retroflexion to the gastroesophageal junction. The assembly may also be configured to include any number of features such as lumens defined through the elongate body for insufflation, suction, and irrigation similar to conventional endoscopes.

Once a desired position is achieved within a patient body, the elongate body may be locked in place. After insertion and positioning, the distal end of a visualization lumen can be elevated above or off-axis relative to the elongate body to provide off-axis visualization. The off-axis visualization lumen may be configured in any number of variations, e.g., via an articulatable platform or an articulatable body to configure itself from a low-profile delivery configuration to an off-axis deployment configuration. The visualization lumen may define a hollow lumen for the advancement or placement of a conventional endoscope therethrough which is appropriately sized to provide off-axis visualization during a procedure.

Alternatively, various imaging modalities, such as CCD chips and LED lighting may also be positioned within or upon the lumen. In yet another alternative, an imaging chip may be disposed or positioned upon or near the distal end of lumen to provide for wireless transmission of images during advancement of the assembly into a patient and during a procedure. The wireless imager may wirelessly transmit images to a receiving unit located externally to a patient for visualization. Various examples of various articulatable off-axis visualization platforms may be seen in further detail in U.S. patent application Ser. No. 10/824,936 filed Apr. 14, 2004, which is incorporated herein by reference in its entirety.

In addition to the off-axis visualization, an end effector assembly having one or more articulatable tools, e.g., graspers, biopsy graspers, needle knives, snares, etc., may also be disposed or positioned upon or near the distal end of the assembly. The tools may be disposed respectively upon a first and a second articulatable lumen. Each of the articulatable lumens may be individually or simultaneously articulated with respect to bending section and the off-axis lumen and any number of tools may be advanced through the assembly and their respective lumens. During advancement endoluminally within the patient body, tools may be retracted within their respective lumens so as to present an atraumatic distal end to contacted tissue. Alternatively, tools may be affixed upon the distal ends of lumens and atraumatic tips may be provided thereupon to prevent trauma to contacted tissue during endoluminal advancement.

Any number of lumens, articulatable or otherwise, may be utilized as practicable. Examples of articulatable lumens are shown in further detail in U.S. Pat. Pubs. 2004/0138525 A1; 2004/0138529 A1; 2004/0249367 A1; and 2005/0065397 A1, each of which have been incorporated by reference above.

The utilization of off-axis visualization and off-axis tool articulation may thereby enable the effective triangulation of various instruments to permit complex, two-handed tissue manipulations. The endoluminal assembly may accordingly be utilized to facilitate any number of advanced endoluminal procedures, e.g., extended mucosal resection, full-thickness resection of gastric and colonic lesions, and gastric remodeling, among other procedures. Moreover, the endoluminal assembly may be utilized in procedures, e.g., trans-luminal interventions to perform organ resection, anastomosis, gastric bypass or other surgical indications within the peritoneal cavity, etc.

BRIEF DESCRIPTION OF THE DRAWINGS

FIGS. 13A to 13D illustrate possible movements of the articulatable off-axis tool arms relative to the elongate body.

FIGS. 39A and 39B illustrate an inflatable balloon assembly in an un-inflated and inflated state where the balloon defines one or more curved lumens therethrough for passing tools or instruments through.

FIG. 45A shows an example of a visualization enhancement where an imaging assembly may provide multiple adjacent imaging chips, e.g., CCD or CMOS.

FIGS. 45B to 45E illustrate how sequential imaging, capturing, and processing of the captured images can be utilized to provide for panoramic endoluminal visualization.

DETAILED DESCRIPTION OF THE INVENTION

Endoluminal access may be achieved more effectively by utilizing off-axis articulation with an endoluminal tissue manipulation assembly advanced within a body lumen, e.g., advanced endoluminally or laparoscopically within the body lumen. As described herein, off-axis articulating elements may act as reconfigurable platforms from which various tools and/or imagers may be advanced or therapies may be conducted. Once the assembly has been desirably situated within the body, a versatile platform from which to access, manipulate, and visualize a greater portion of the body lumen may be deployed from a device having a relatively small delivery profile.

Figure 1:
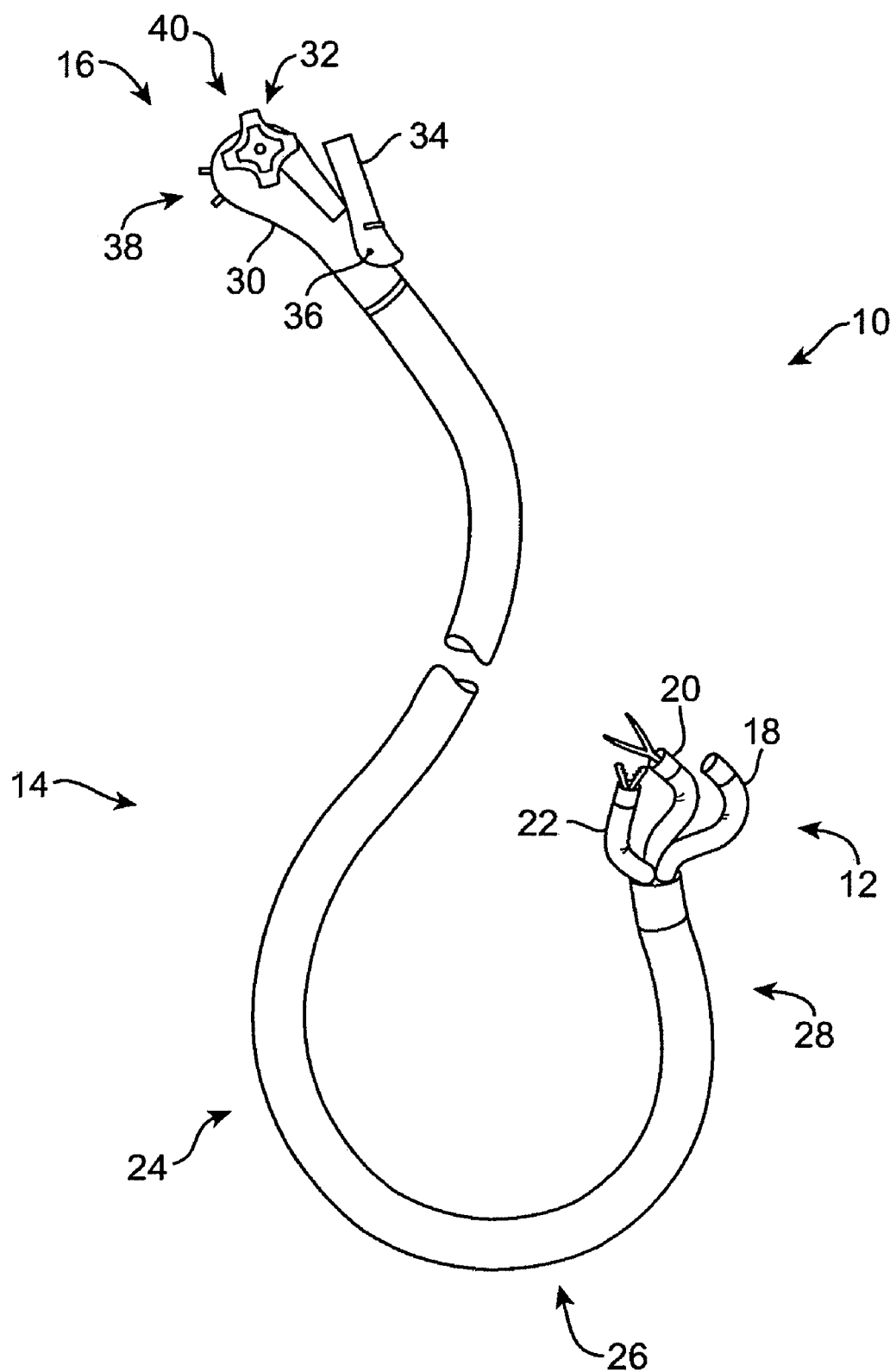
FIG. 1 shows an illustrative view of one variation of an endoluminal tissue treatment assembly having a handle, an optionally rigidizable elongate body, and an end effector assembly with articulatable off-axis tool arms and articulatable off-axis visualization.

With reference to FIG. 1, the endoluminal tissue manipulation 10 assembly as described herein may comprise, at least in part, a distal end effector assembly 12 disposed or positionable at a distal end of a flexible and elongate body 14. A handle assembly 16 may be connected to a proximal end of the elongate body 14 and include a number of features or controls for articulating and/or manipulating both the elongate body 14 and/or the distal end effector assembly 12.

The elongate body 14 may optionally utilize a plurality of locking or lockable links nested in series along the length of the elongate body 14 which enable the elongate body 14 to transition between a flexible state and a rigidized or shape-locked configuration. Details of such a shape-lockable body may be seen in further detail in U.S. Pat. Nos. 6,783,491; 6,790,173; and 6,837,847, each of which is incorporated herein by reference in its entirety. Alternatively, elongate body 14 may comprise a flexible body which is not rigidizable or shape-lockable but is flexible in the same manner as a conventional endoscopic body, if so desired. Additionally, elongate body 14 may also incorporate additional features that enable any number of therapeutic procedures to be performed endoluminally. Elongate body 14 may be accordingly sized to be introduced per-orally. However, elongate body 14 may also be configured in any number of sizes, for instance, for advancement within and for procedures in the lower gastrointestinal tract, such as the colon.

Elongate body 14, in one variation, may comprise several controllable bending sections along its length to enable any number of configurations for the elongate body 14. Each of these bending sections may be configured to be controllable separately by a user or they may all be configured to be controlled simultaneously via a single controller. Moreover, each of the control sections may be disposed along the length of elongate body 14 in series or they may optionally be separated by non-controllable sections. Moreover, one, several, or all the controllable sections (optionally including the remainder of elongate body 14) may be rigidizable or shape-lockable by the user.

In the example of endoluminal tissue manipulation assembly 10, elongate body may include a first articulatable section 24 located along elongate body 14. This first section 24 may be configured via handle assembly 16 to bend in a controlled manner within a first and/or second plane relative to elongate body 14. In yet another variation, elongate body 14 may further comprise a second articulatable section 26 located distal of first section 24. Second section 26 may be configured to bend or articulate in multiple planes relative to elongate body 14 and first section 24. In yet another variation, elongate body 14 may further comprise a third articulatable section 28 located distal of second section 26 and third section 28 may be configured to articulate in multiple planes as well, e.g., 4-way articulation, relative to first and second sections 24, 26.

As mentioned above, one or each of the articulatable sections 24, 26, 28 and the rest of elongate body 14 may be configured to lock or shape-lock its configuration into a rigid set shape once the articulation has been desirably configured. Detailed examples of such an apparatus having one or multiple articulatable bending sections which may be selectively rigidized between a flexible configuration and a shape-locked configuration may be seen, e.g., in U.S. Pat. Pub. Nos. 2004/0138525 A1, 2004/0138529 A1, 2004/0249367 A1, and 2005/0065397 A1, each of which is incorporated herein by reference in its entirety. Although three articulatable sections are shown and described, this is not intended to be limiting as any number of articulatable sections may be incorporated into elongate body 14 as practicable and as desired.

Handle assembly 16 may be attached to the proximal end of elongate body 14 via a permanent or releasable connection. Handle assembly 16 may generally include a handle grip 30 configured to be grasped comfortably by the user and an optional rigidizing control 34 if the elongate body 14 and if one or more of the articulatable sections are to be rigidizable or shape-lockable. Rigidizing control 34 in this variation is shown as a levered mechanism rotatable about a pivot 36. Depressing control 34 relative to handle 30 may compress the internal links within elongate body 14 to thus rigidize or shape-lock a configuration of the body while releasing control 34 relative to handle 30 may in turn release the internal links to allow the elongate body 14 to be in a flexible state. Further examples of rigidizing the elongate body 14 and/or articulatable sections may again be seen in further detail in U.S. Pat. Pub. Nos. 2004/0138525 A1, 2004/0138529 A1, 2004/0249367 A1, and 2005/0065397 A1, incorporated above by reference. Although the rigidizing control 34 is shown as a lever mechanism, this is merely illustrative and is not intended to be limiting as other mechanisms for rigidizing an elongate body, as generally known, may also be utilized and are intended to be within the scope of this disclosure.

Handle assembly 16 may further include a number of articulation controls 32, as described in further detail below, to control the articulation of one or more articulatable sections 24, 26, 28. Handle 16 may also include one or more ports 38 for use as insufflation and/or irrigation ports, as so desired.

At the distal end of elongate body 14, end effector assembly 12 may be positioned thereupon. In this variation, end effector assembly 12 may include first tissue manipulation arm 20 and second tissue manipulation arm 22, each being independently or simultaneously articulatable and each defining a lumen for the advancement of tools or instruments therethrough. Each of the tools or instruments may be advanced through tool ports 40 located in handle assembly 16 to project from articulatable arms 20, 22 and controlled from handle assembly 16 or proximal to handle assembly 16. Alternatively, various tools or instruments may be attached or connected directly to the distal ends of arms 20, 22 and articulatable from handle assembly 16. At least one of the articulatable arms 20, 22 may be articulatable to reconfigure from a low-profile straightened configuration to a deployed configuration where at least one of the arms 20, 22 is off-axis relative to a longitudinal axis of elongate body 14. Various articulation and off-axis configurations for articulatable arms 20, 22 may be seen in further detail in U.S. Pat. Pub. Nos. 2004/0138525 A1, 2004/0138529 A1, 2004/0249367 A1, and 2005/0065397 A1, incorporated above by reference.

End effector assembly 12 may further include a visualization lumen or platform 18 which may be articulatable into a deployed configuration such that a lumen opening or distal end of visualization lumen or platform 18 is off-axis relative to the longitudinal axis of elongate body 14, as described in further detail below.

Figure 2A:
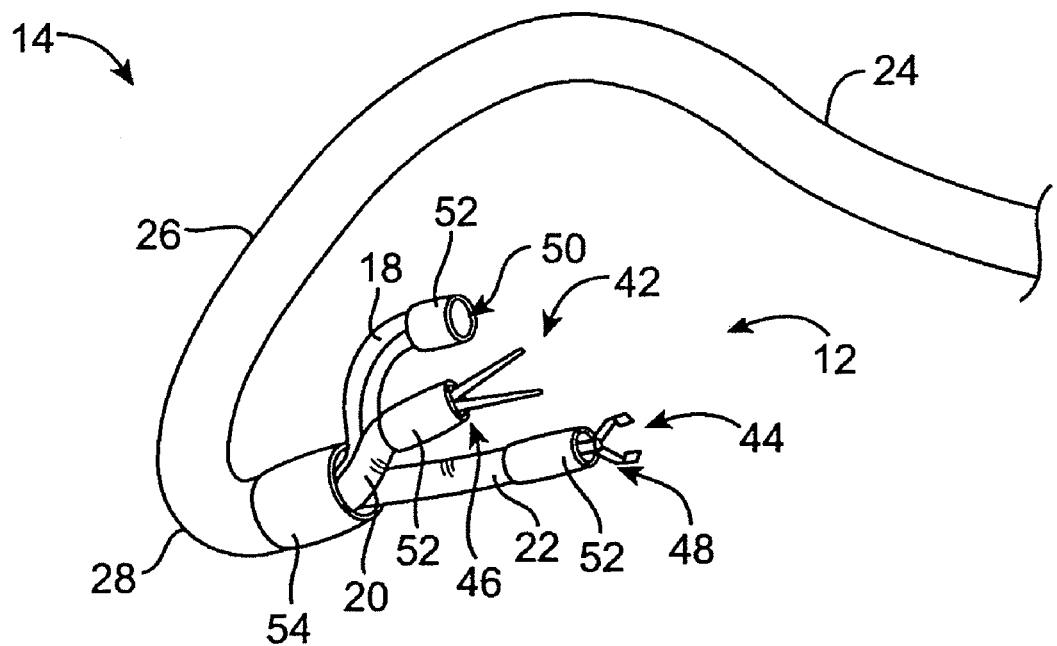
FIGS. 2A and 2B show illustrative perspective views of a variation of the end effector assembly in a deployed configuration and a low-profile delivery configuration, respectively.
Figure 2B:
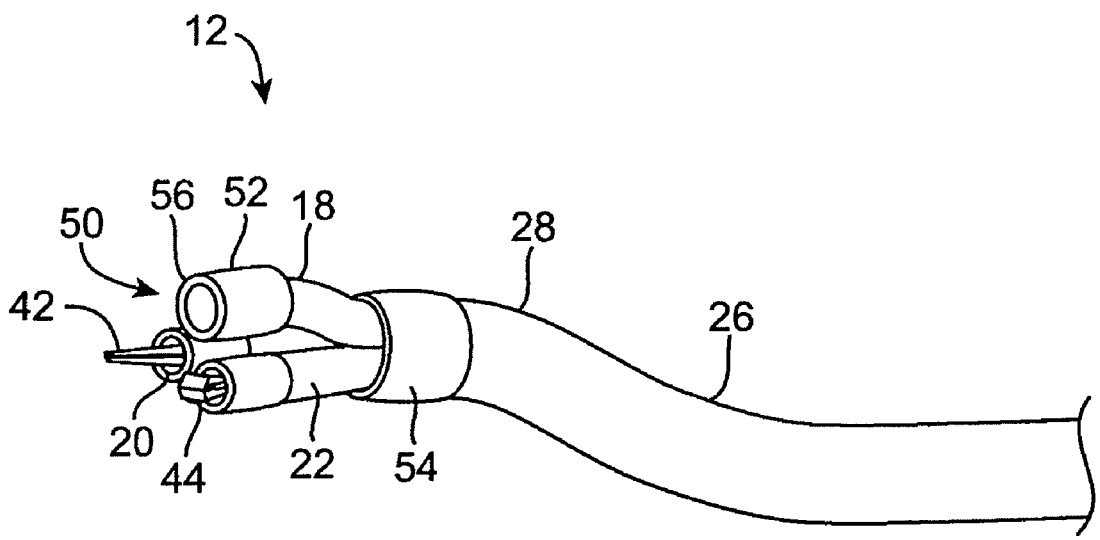

FIGS. 2A and 2B show illustrative perspective views of a variation of the end effector assembly 12 in a deployed configuration and a low-profile delivery configuration, respectively. As seen in FIG. 2A, first and second articulatable arms 20, 22, respectively, may be seen in an off-axis configuration with a first tool 42, e.g., any conventional tool such as a Maryland dissector, Babcock graspers, etc., advanced through first tool lumen 46 within first articulatable arm 20. Likewise, second articulatable arm 22 may have a second tool 44, e.g., any conventional tool such as claw graspers, needle knife, etc., advanced through second tool lumen 48 within second articulatable arm 22. First and second tools 42, 44 may be articulated separately or simultaneously for tissue manipulation and advanced freely distally and proximally through their respective tool lumens 46, 48.

Visualization lumen or platform 18 may also be seen in FIG. 2A articulated into its off-axis configuration relative to elongate body 14. Visualization lumen opening 50 defined at the distal end of visualization platform 18 may be seen articulated into an off-axis configuration which directs visualization opening 50 such that the field-of-view provided therefrom is directly over or upon an area occupied by the articulated tool arms 20, 22 and respective tools 46, 48. Visualization from platform 18 may be provided by any number of different methods and devices. In a first example, visualization may be provided by an endoscope 56 having imaging capabilities advanced through elongate body 14 and through visualization platform 18. Imaging endoscope 56 may be advanced distally to project from lumen opening 50 or it may be positioned within visualization platform 18 such that its distal end is proximal of or flush with lumen opening 50. Alternatively, imaging electronics such as CCD imaging chips or any other number of imaging chips may be positioned within visualization platform 18 to provide images of the field-of-view. These electronic images may be transmitted through wires proximally through elongate body 14 or they may alternatively be transmitted wirelessly to a receiver located externally of the patient body, as described below in further detail.

FIG. 2B shows the end effector assembly 12 in a low-profile configuration for endoluminal advancement through a patient body. An atraumatic distal tip 54 may be provided over the distal end of elongate body 14 and separate atraumatic distal tips 52 may also be provided as well over the distal ends of first and second articulatable tool arms 20, 22.

Figure 3:
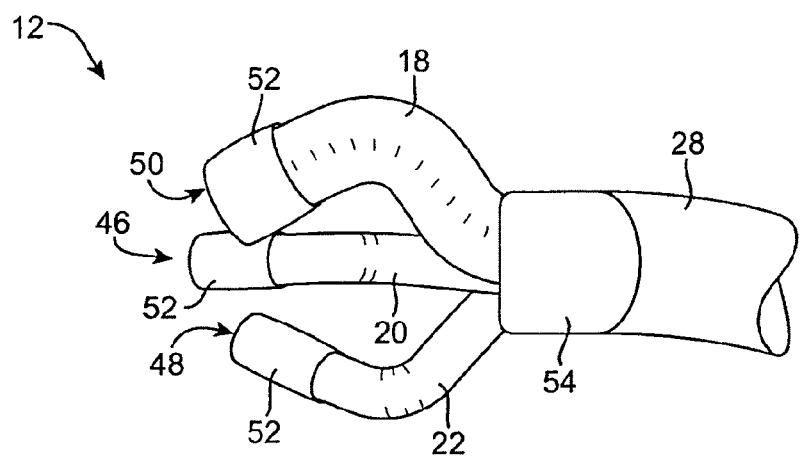
FIG. 3 shows a side view of the end effector assembly of FIGS. 2A and 2B.

FIG. 3 shows a side view of the end effector assembly 12 of the apparatus of FIG. 2A. As illustrated, first and second tools 42, 44 may be withdrawn into their respective tool lumens 46, 48 during endoluminal advancement of elongate body 14 through the patient and advanced through tool lumens 46, 48 prior to or after articulation of arms 20, 22. Likewise with visualization platform 18, if a visualization endoscope is advanced therethrough, endoscope 56 may be positioned within platform 18 during endoluminal advancement of elongate body 14 or after platform 18 has been articulated.

Figures 4A, 4B:
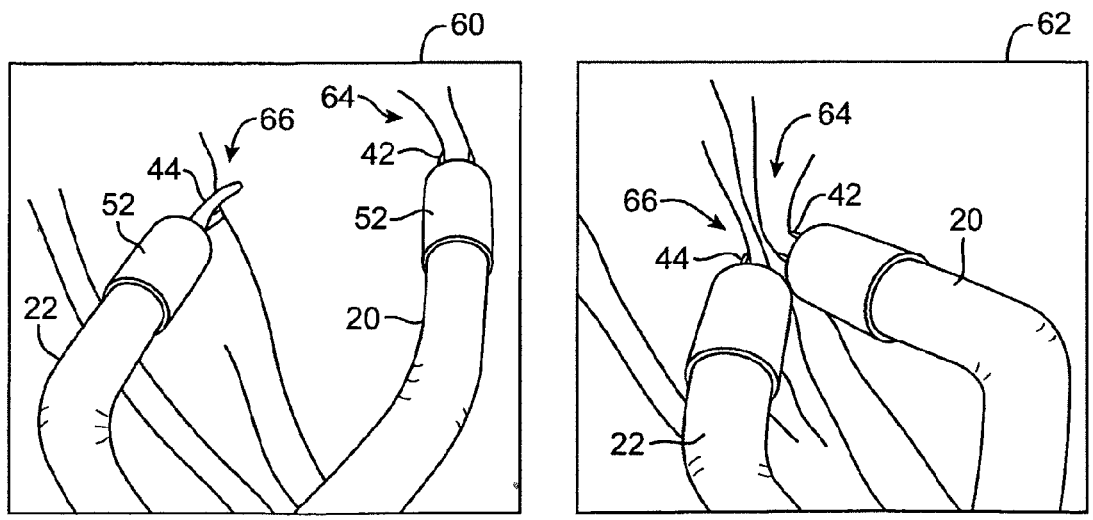
FIGS. 4A and 4B illustrate a typical view of the articulatable off-axis tool arms performing a procedure on a tissue region of interest from the perspective of the off-axis visualization lumen.

FIGS. 4A and 4B show an example of the image which an off-axis visualization platform 18 may provide during a tissue manipulation procedure. As seen in FIG. 4A, the visualization image 60 as may be seen on a monitor by the physician during a procedure provides for an off-axis view of the tissue region of interest as well as first and second tools 42, 44 and articulatable arms 20, 22. Such an "overhead" perspective enables the physician to gain an overview of the tissue region of interest during a procedure and facilitates the procedure by further enabling the physician to triangulate the location of the tools 42, 44 with respect to the tissue. Accordingly, manipulation of first tissue region 64 and second tissue region 66 may be readily accomplished by the physician while viewing the tissue region from off-axis platform 18. As seen in the visualization image 62 in FIG. 4B, the tissue regions 64, 66 may be manipulated by articulatable tool arms 20, 22, even when the tissue regions are approximated towards one another; such tissue manipulation and visualization would generally be extremely difficult, if not impossible, using conventional endoscopic devices and tools which are typically limited to straight-line tools and obstructed views typically afforded conventional endoscopes. The utilization of off-axis visualization and off-axis tool articulation may thereby enable the effective triangulation of various instruments to permit complex, two-handed tissue manipulations.

The end effector assembly 12 may accordingly be utilized to facilitate any number of advanced endoluminal procedures, e.g., extended mucosal resection, full-thickness resection of gastric and colonic lesions, and gastric remodeling, among other procedures. Moreover, assembly 10 may be utilized in procedures, e.g., trans-luminal interventions to perform organ resection, anastomosis, gastric bypass or other surgical indications within the peritoneal cavity, etc.

Figure 5:
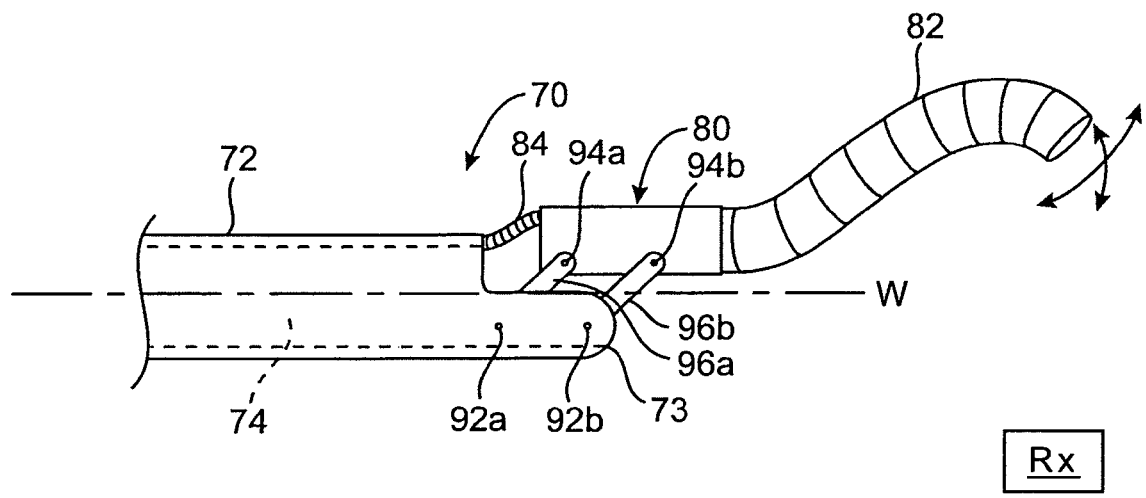
FIG. 5 illustrates another variation of the off-axis visualization lumen in one deployed configuration.

Referring now to FIG. 5, another variation is described wherein the articulating element comprises a steerable shaft. Visualization assembly 70 may generally comprise elongate body 72 having longitudinal axis W, distal region 73 and lumen 74. As mentioned above, elongate body 72 may comprise a rigidizable and/or articulatable body or it may comprise a passively flexible body. Assembly 70 further may further comprise articulating element or platform 80 disposed near distal region 73 of elongate body 72. Platform 80 may be coupled to the elongate body by linkages 96a, 96b rotatably disposed between hinges 92a, 94a and 92b, 94b, respectively. Articulating platform 80 via hinges 92a, 94a and 92b, 94b may allow for lumens or lumen 74 to be unobstructed with the platform 80 articulated away from the openings. Visualization assembly 70 may be seen in further detail in U.S. patent application Ser. No. 10/824,936, which has been incorporated herein above by reference.

Articulating platform 80 may further comprise articulatable visualization lumen 82. Visualization lumen 82 may be passively articulatable or, alternatively, may be actively controllable. Any number of conventional methods may be utilized to articulate the shape and configuration of lumen 82. In FIG. 5, lumen 82 illustratively may, for example, be steerable in any number of directions. In this variation, lumen 82 may be steerable in at least four directions, e.g., via four control wires routed through or along cable 84 and elongate body 72 to a proximal region of assembly 70 for manipulation by a medical practitioner. Cable 84 may also be used to articulate platform 80. The control wires for steerable lumen 82 may be routed through or along body 72 in spaces that would not be usable as working lumens or for tool insertion.

During delivery, articulating platform 80 and steerable lumen 82 are typically aligned with axis W of elongate body 72. Advantageously, the ability to articulate platform 80 off-axis post-delivery allows assembly 70 to have both a large working lumen 74 and a small collapsed delivery profile. Furthermore, steerable platform 82 gives the assembly an off-axis platform with added functionality for performing complex procedures. The steering capability of lumen 82 may be used to steer therapeutic or diagnostic tools, and/or for illumination, visualization, fluid flushing, suction, etc., into better position for conducting such procedures.

Various methods and apparatus for controlling elements used in conjunction with lumen 82 may be routed through cable 84 along with the control wires for lumen 82. For example, when a visualization element is coupled to steerable shaft 82, electrical wires may run through cable 84 for sending and/or receiving signals, power, etc., to/from the visualization element. In such a variation, the visualization element would allow direct visualization during insertion within a body lumen, while providing off-axis visualization and steering, as well as facilitating tool introduction, post-articulation.

Alternatively or additionally, when a working lumen is disposed through steerable lumen 82, cable 84 may comprise a lumen for connecting the shaft lumen to a lumen extending through elongate body 72 of assembly 70 through which any number of visualization instruments may be advanced through.

Alternatively or additionally, various imaging modalities, such as CCD chips and LED lighting may also be positioned within or upon lumen 82. In yet another alternative, an imaging chip may be disposed or positioned upon or near the distal end of lumen 82 to provide for wireless transmission of images during advancement of assembly 70 into a patient and during a procedure. The wireless imager may wirelessly transmit images to a receiving unit RX located externally to a patient for visualization.

Figure 6:
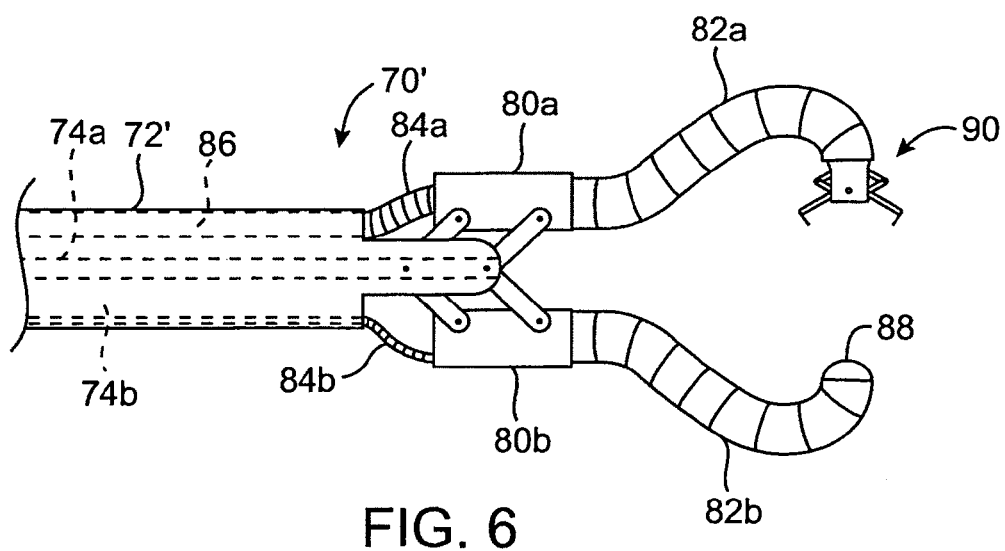
FIG. 6 shows another variation of the end effector assembly in which the off-axis visualization assembly may be utilized with at least one articulatable off-axis tool arm.

Referring now to FIG. 6, an alternative variation of assembly 70 is shown comprising multiple articulating elements having steerable shafts. Assembly 70' may comprise first articulating platform 80a and second articulating platform 80b. Platform 80 may comprise first steerable lumen 82a and second steerable lumen 82b, respectively. Lumens 74a and 74b extend through elongate body 72' and are exposed upon articulation of platform 80a and 80b, respectively. As will be apparent, a single lumen or more than two lumens alternatively may be provided. Likewise, more than two articulating elements and/or steerable shafts optionally may be provided.

First steerable lumen 82a illustratively is shown with working lumen 86 that extends through the lumen, as well as through cable 84a and elongate body 72'. Exemplary grasper tool 90 is shown advanced through lumen 86. Second steerable lumen 82b illustratively is shown with visualization element 88, as previously described, coupled to an end thereof. Electrical wires, e.g., for powering and transmitting signals to/from the visualization element, may be disposed within cable 84b. As will be apparent, steerable lumens 82 may be provided with additional or alternative capabilities. In the case of visualization element 88 being a wireless imager, electrical wires may be omitted altogether.

Figure 7:
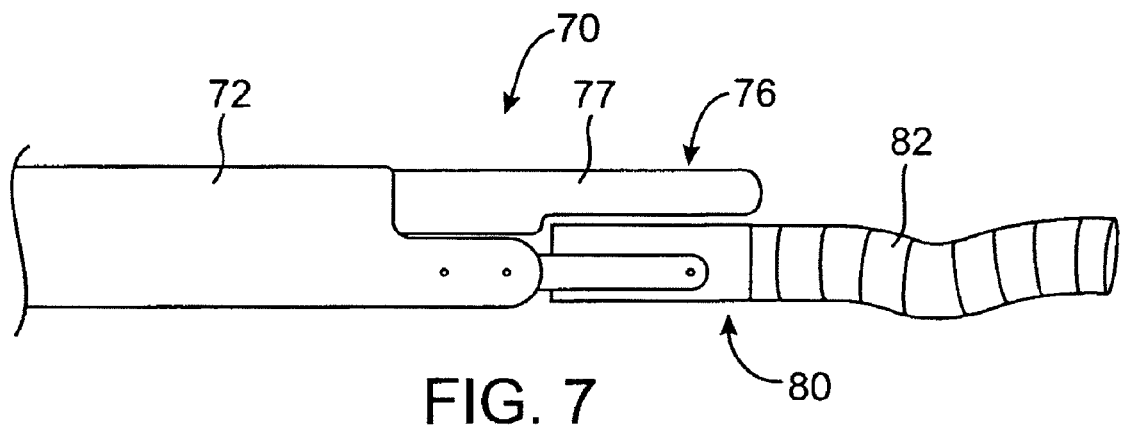
FIG. 7 shows another variation of the end effector assembly in which an inflatable balloon may be utilized for providing an atraumatic surface during low-profile advancement of the end effector.
Figure 8:
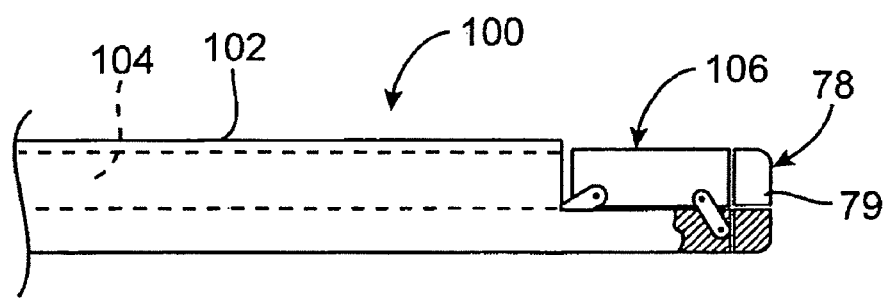
FIG. 8 shows another variation in which a cap may be utilized at the distal end of the assembly to provide an atraumatic surface for low-profile advancement.

With reference to FIGS. 7 and 8, illustrative embodiments of atraumatic tips for use with the assembly 70 are described. As shown in FIG. 7, assembly 70 is shown with atraumatic tip 76. Tip 76 provides a smooth transition between elongate body 72 and articulating platform 80 with steerable lumen 82. Tip 76 may, for example, comprise an inflatable balloon 77 that may be inflated as shown during insertion and delivery of assembly 70, then deflated prior to articulation of platform 80 and off-axis steering of lumen 82, so as not to block or impede articulation or the distal opening of the lumen 74 post-articulation.

In FIG. 8, assembly 100 may comprise an alternative atraumatic tip 78 having cap 79, which optionally may be fabricated from rubber. Cap 79 may be U-shaped to both provide a smooth transition between elongate body 102 and articulating platform 106 in the delivery configuration, as well as to ensure that the cap does not block or impede lumen 104 post-articulation.

Figure 9:
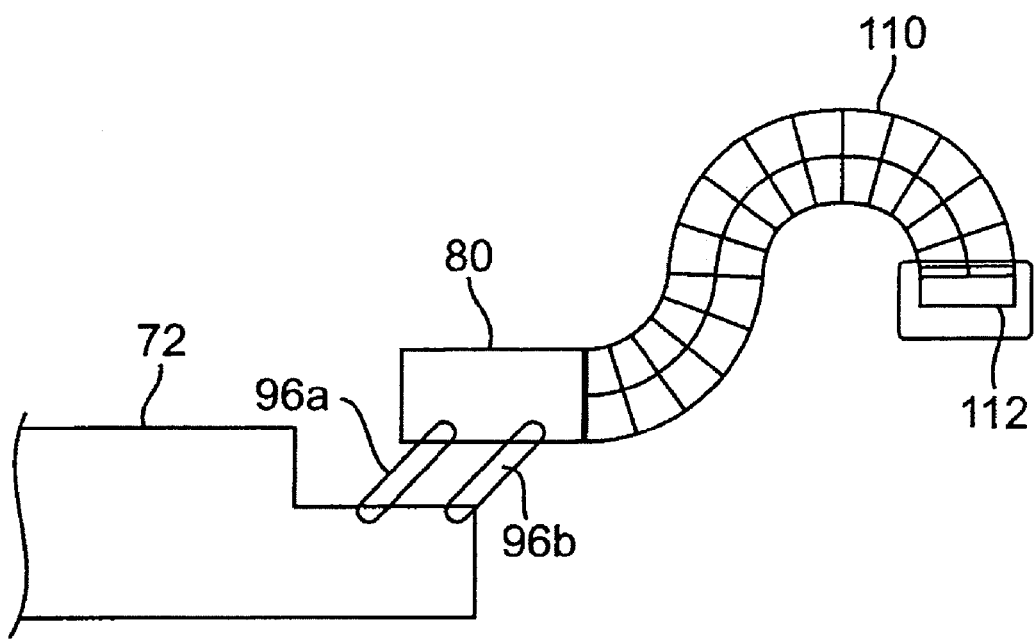
FIG. 9 shows yet another variation of the off-axis visualization lumen in which an articulatable lumen disposed upon a reconfigurable platform may be configured such that visualization of the tissue region of interest directly beneath the imager may be provided.
Figure 10:
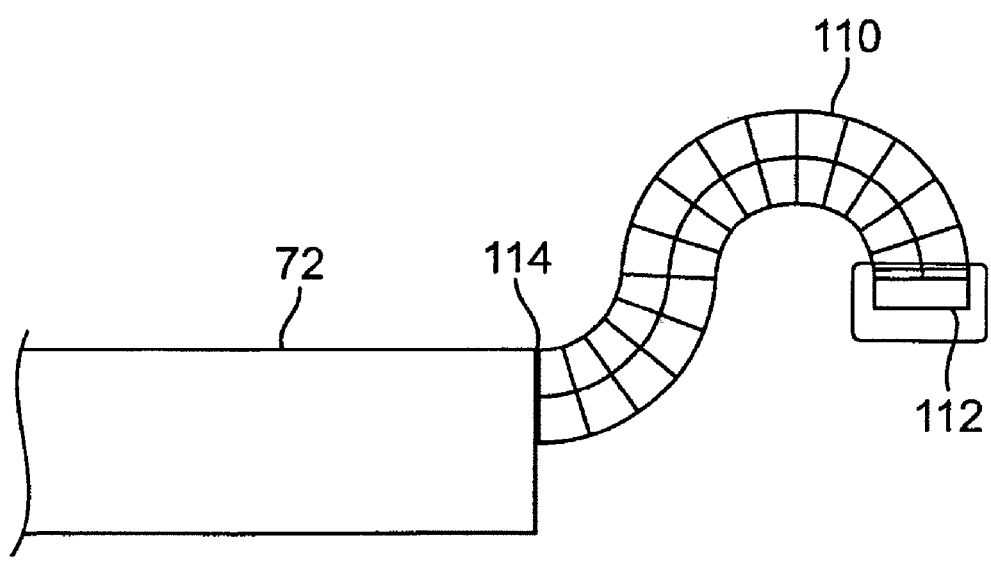
FIG. 10 shows yet another variation of the off-axis visualization lumen attached to the distal end of the elongate body.

FIGS. 9 and 10 show additional alternative configurations of the articulatable platform and visualization lumen. Articulatable visualization lumen 110 may be manipulated to articulate in an off-axis configuration such that visualization lumen opening 112 is directed to face in a direction which is off-axis relative to a longitudinal axis of elongate body 72 and which is also perpendicular relative to the longitudinal axis. Although visualization lumen 110 may be articulated to face any number of directions, such a configuration may allow for a visualization element positioned within opening 112 to directly face over or upon the tissue region of interest, if so desired.

As shown in FIG. 9, visualization lumen 110 may be positioned upon platform 80 and articulated via linkages 96a, 96b, as described above. Alternatively, visualization lumen 110 may also be directly attached via interface 114 to elongate body 72 and articulated therefrom, also as described above.

Figure 11:
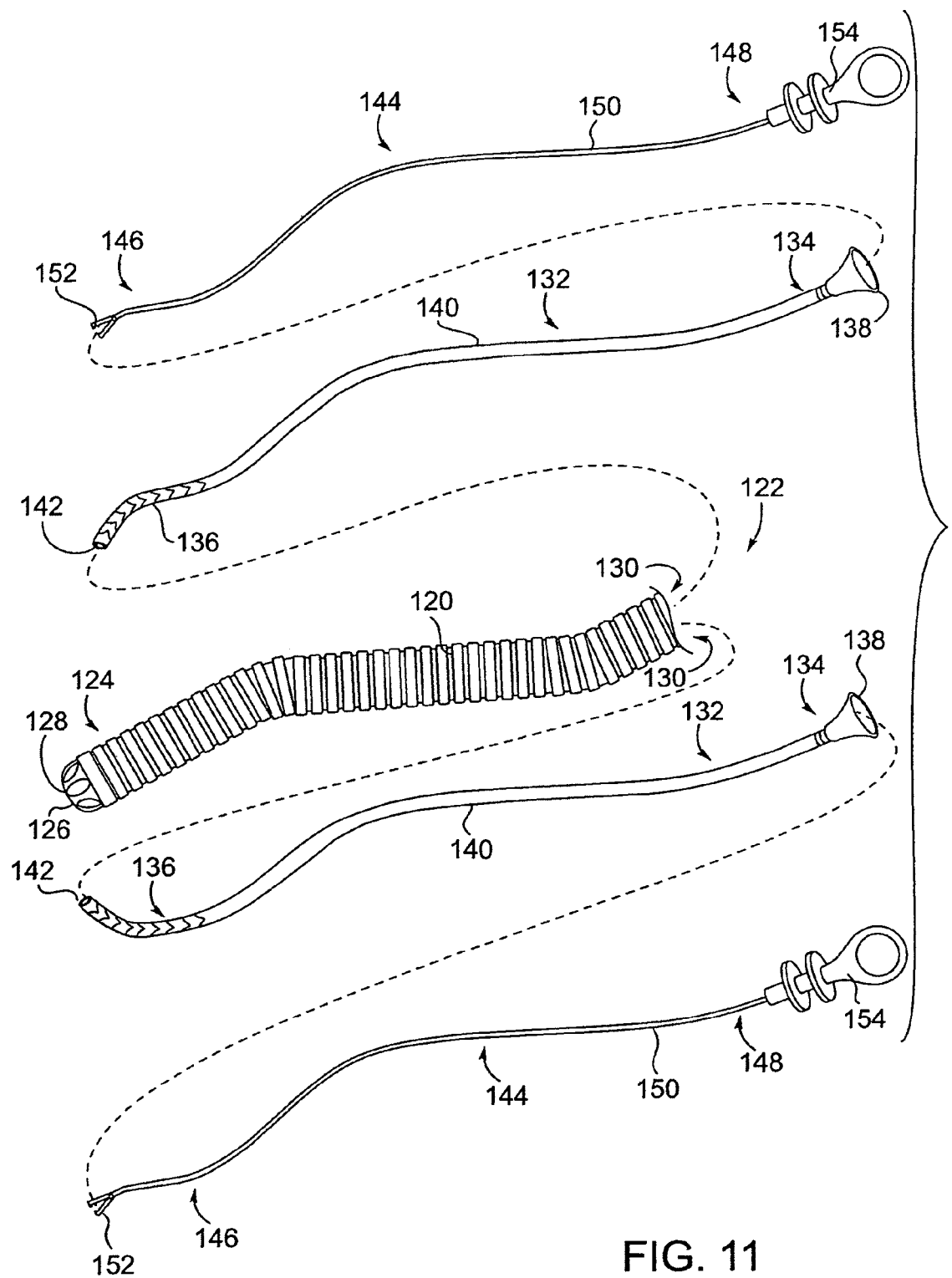
FIG. 11 illustrates an exploded assembly view of one variation for the tool arms.

Turning now to the elongate body, FIG. 11 illustrates one variation for assembly of the elongate body 120. Distal end effector assembly 12 has been omitted merely for the sake of clarity from FIG. 11 and following figures. The elongate body 120 may have a single lumen therethrough for a variety of uses, such as for passage of one or more instruments or for the passage of air or fluid, such as for aspiration or suction. Similarly, the elongate body 120 may have more than one lumen passing therethrough, each lumen used for a different function.

Further details of the elongate body construction may be seen in any of the following U.S. Pat. Pubs. 2004/0138525 A1; 2004/0138529 A1; 2004/0249367 A1; and 2005/0065397 A1, each of which is incorporated herein by reference in its entirety.

In some variations, elongate body 120 may include at least one instrument or tool lumen 130, e.g. an arm guide lumen, which extends over or through at least a distal section of the elongate body 120, typically along the majority of the length of the body 120 as shown. Here in FIG. 11, two arm guide lumens 130 are shown, each extending from a position along the shaft 120 near the proximal end 122 to the distal tip 126. In addition, the elongate body 120 includes a visualization lumen 128, which extends through the shaft 120 to the distal tip 126.

In some variations, the assembly also includes at least one tool arm 132, two are shown in FIG. 11, each arm 132 of which is insertable through a separate arm guide lumen 130 as indicated by the dashed lines. Each tool arm 132 has a proximal end 134, a distal end 136 and a shaft 140 therebetween. The distal end 136 optionally is steerable, such as by manipulation of adjacent links as schematically indicated. Such steerability may be controlled by any number of methods, e.g., a steering cuff 138, which is part of the proximal end 134. The shaft 140 is typically flexible or deflectable to allow deflection of the surrounding elongate body shaft 120. Each tool arm 132 may additionally include a tool deployment lumen 142 therethrough.

Elongate body 120 includes at least one tool 144 with two tools 144 shown in FIG. 11. Each tool 144 includes a distal end 146, a proximal end 148 and an elongate shaft 150 therebetween to allow passage through the tool deployment lumen 142 of the tool arm 132, or through lumen 130 of elongate body 120. Each tool 144 has an end effector 152 disposed at the distal end 146 and optionally a handle 154 at the proximal end 148 for manipulation of the end effector 152 from outside the body. The tool 144 is advanced so that the end effector 152 emerges from the distal end 136 of the arm 132, or from distal tip 126 of elongate body 120. As will be apparent, tool 144 optionally may be formed integrally with tool arm 132. Accordingly, rather than utilizing one or more tool arm shafts 140 insertable through elongate body 120, articulatable distal ends 136 may alternatively be connected directly near or at the distal tip 126 of elongate body 120. Additionally, the distal ends of tools 144 may also be connected directly to articulatable distal ends 136.

Figure 12:
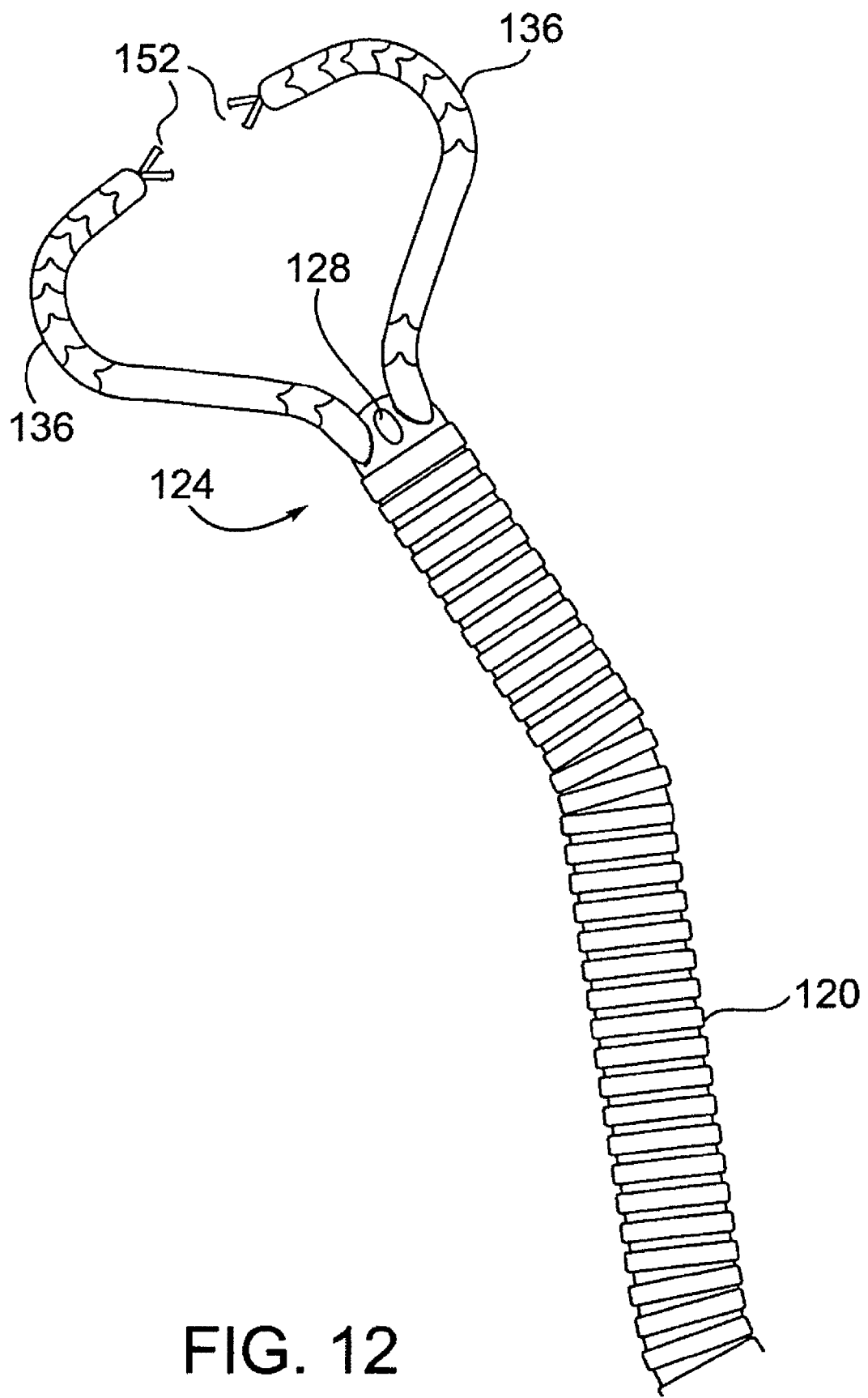
FIG. 12 illustrates a side view of the tool arms in a deployed configuration.

FIG. 12 illustrates the assembly of FIG. 11 in an exemplary assembled arrangement. Here, the tool arms 132 are shown inserted through the arm guide lumens 130 of the elongate body shaft 120. The steerable distal ends 136 of the arms 132 protrude from the distal end 124 of the elongate body 120 and the proximal ends 134 of the arms 132 protrude from the proximal end 122 of the elongate body 120. Additionally, the tools 144 are shown inserted through the tool deployment lumens 142 so that the end effectors 152 extend beyond the steerable distal ends 136 of the arms. Likewise, the proximal ends 148 of the tools 144 with handles 154 may protrude proximally from the assembly. As described above, the articulatable visualization lumen 18 or 110 (omitted from the figure for clarity) may be connected to the distal end of 124 of elongate body 120 at the location of lumen 128. Alternatively, an endoscope used for visualization may be routed directly through lumen 128.

FIGS. 13A to 13D illustrate a series of movements of the steerable distal ends 136 of the tool arms 132. This series serves only as an example, as a multitude of movements may be achieved by the distal ends 136 independently or together. Moreover, articulatable visualization lumen or platform 18 or 110 has been omitted from the illustrations merely for the sake of clarity. FIG. 13A illustrates the distal tip 126 of the elongate body 120. The visualization lumen 128 is shown along with two arm guide lumens 130. FIG. 13B illustrates the advancement of the distal ends 136 of the tool arms 132 through the arm guide lumens 130 so that the arms 132 extend beyond the distal tip 126.

FIGS. 13C and 13D illustrate deflection of the arms 132 to an exemplary arrangement. FIG. 13C illustrates deflection of the arms 132 laterally outward. This may be achieved by curvature in the outward direction near the base 156 of the steerable distal end 136. FIG. 13D illustrates deflection of the tip section 158 of the distal end 136 laterally inward achieved by curvature in the inward direction. When an imager 162 is positioned within the lumen 128, the tip sections 158 of the tool arms 132 and any tools 144 advanced therethrough, will be visible through the imager 162. Additionally, when articulatable visualization lumen 18 or 110 is positioned within or connected to lumen 128, articulation of the visualization lumen into its off-axis configuration will bring tools 132, and in particular the distal ends 136 of tool arms 132 into the field-of-view, as described above. In FIGS. 13C and 13D, deflection of the arms 132 may be achieved with the use of adjacent links 160 in the areas of desired curvature.

Variations of such links 160 and other mechanisms of deflection are described in further detail in U.S. Pat. Pubs. 2004/0138525 A1; 2004/0138529 A1; 2004/0249367 A1; and 2005/0065397 A1, each of which has been incorporated above herein by reference. Further, the deflection shown in FIGS. 13A to 13D are shown to be within a single plane. However, variations include deflection in multiple planes. Likewise, the arms 132 are shown to be deflected simultaneously in FIGS. 13A to 13D, however the arms 132 may be deflected selectively or independently.

Figure 14:
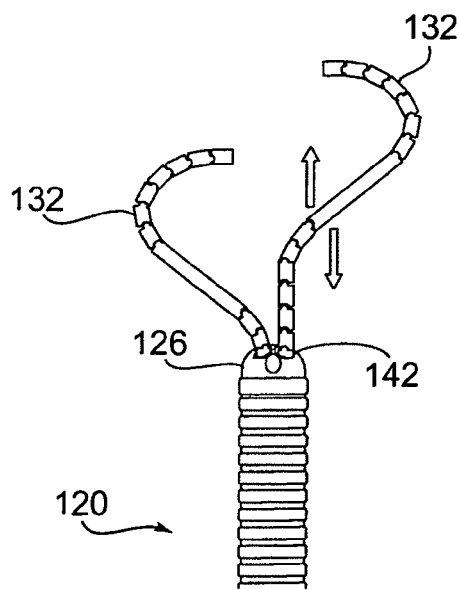
FIG. 14 illustrates the possible longitudinal advancement of at least one tool arm relative to the elongate body.
Figure 15:
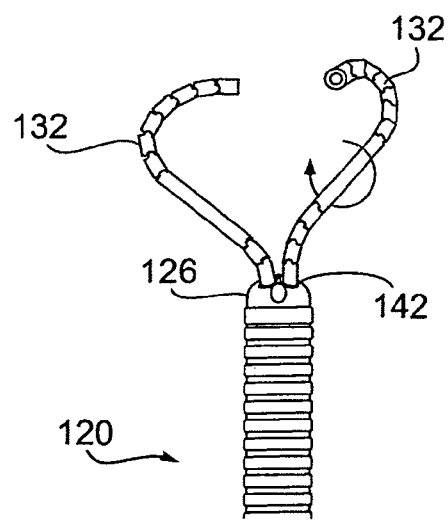
FIG. 15 illustrates the possible rotational motion of at least one tool arm about its longitudinal axis relative to the elongate body.
Figure 16:
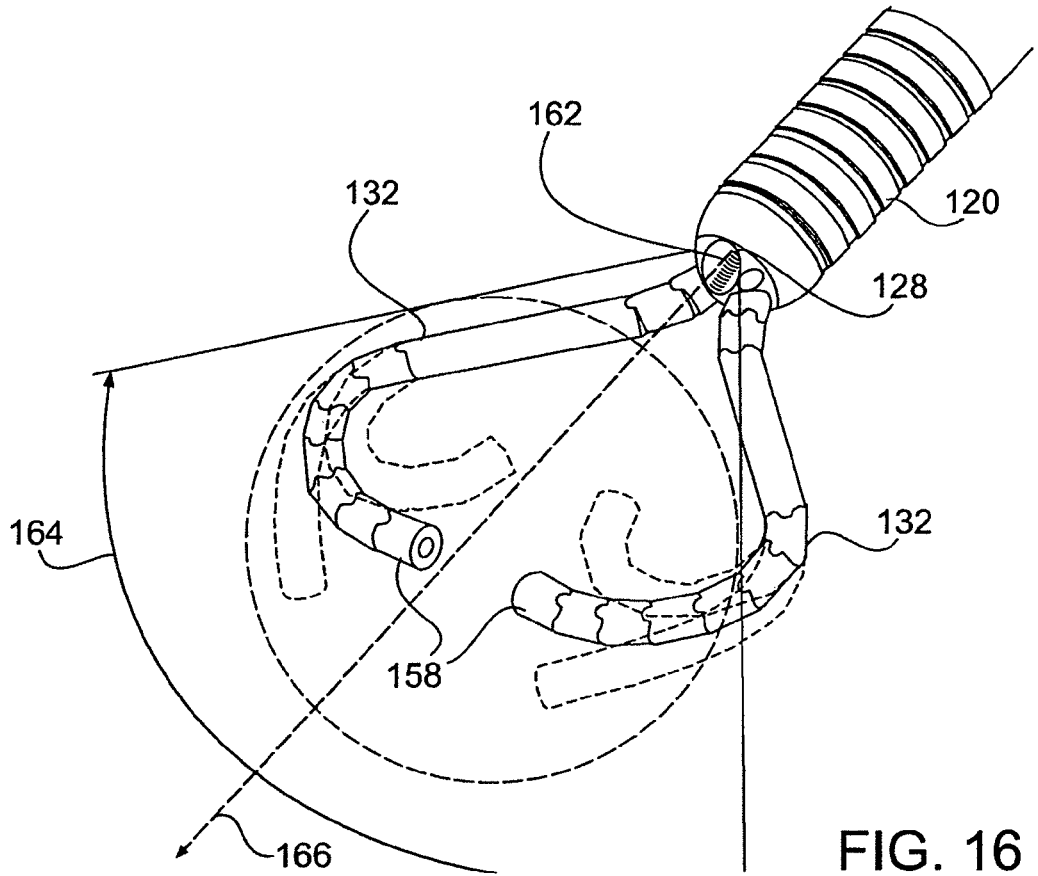
FIG. 16 illustrates some of the possible articulation of the tool arms relative to one another.

FIGS. 14 to 16 illustrate additional possible movements of the tool arms 132. For example, FIG. 14 illustrates possible axial movement of the tool arms 132. Each tool arm 132 can independently move distally or proximally, such as by sliding within the tool deployment lumen 142, as indicated by the arrows. Such movement may maintain the arms 132 within the same plane, yet allows more diversity of movement and therefore surgical manipulations. FIG. 15 illustrates rotational movement of the tool arms 132. Each tool arm 132 can independently rotate, such as by rotation of the arm 132 within the tool deployment lumen 142, as indicated by circular arrow. Such rotation may move the arm or arms 132 through a variety of planes. By combining axial, lateral and rotational movement, the arms 132, and therefore the tools 144 positioned therethrough (or formed integrally therewith), may be manipulated through a wide variety of positions in one or more planes.

FIG. 16 illustrates further articulation of the tool arms 132. In some variations, the arms 132 may be deflectable to form a predetermined arrangement. Typically, when forming a predetermined arrangement, the arms 132 are steerable up until the formation of the predetermined arrangement wherein the arms 132 are then restricted from further deflection. In other variations, the arms 132 may be deflectable to a variety of positions and are not limited by a predetermined arrangement. Such an example is illustrated in FIG. 16 wherein the arms 132 articulate so that the tip sections 158 curl inwardly. The tip sections 158 may be positioned in front of the lumen 128 and imager 162 for viewing or within the field-of-view provided by the off-axis articulation of visualization lumen 18 or 110 (omitted for clarity). Typically, the tip sections 158 may be positioned on opposite sides of a longitudinal axis 166 of the elongate body 120, wherein for an imager 166 positioned within lumen 128, in one variation, the field-of-view (indicated by arrow 164) may span up to, e.g., approximately 140 degrees.

Figure 17A:
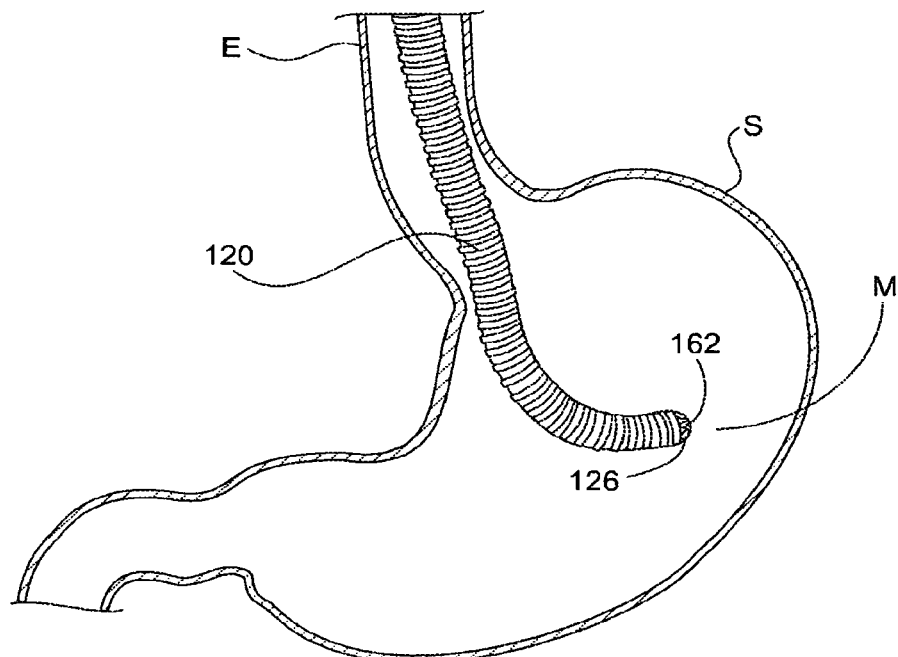
FIGS. 17A and 17B illustrate one example for advancing an elongate body transesophageally into the stomach for performing a procedure.
Figure 17B:
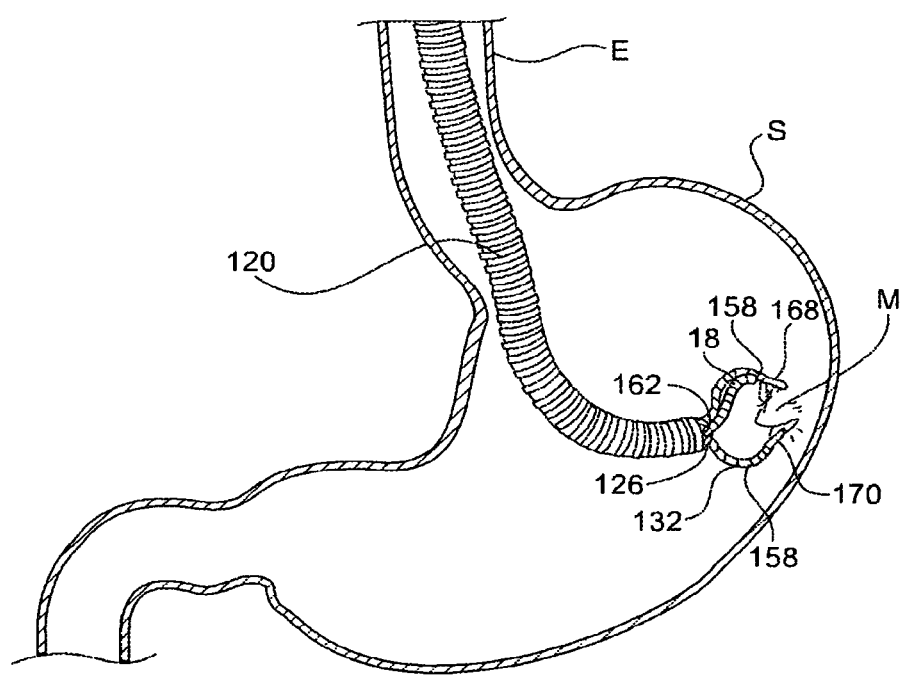

FIGS. 17A and 17B illustrate one example for use of the endoluminal assembly 10. FIG. 17A illustrates advancement of the elongate body 120 through the esophagus E to the stomach S, as shown in FIG. 17A. The elongate body 120 may then be steered to a desired position within the stomach S, and a tissue region of interest M may be visualized by visualization lumen or platform 18, which may be articulated into its off-axis configuration, as shown in FIG. 17B. Tool arms 132 may also be advanced, if not already attached directly to the distal end of elongate body 120, through the elongate body 120 and articulated. As previously described, one or several tools 144 may be advanced through the tool arms 132, or an end effector 152 may be disposed at the distal end of each arm 132. In this example, a grasper 168 is disposed at the distal end of one arm 132 and a cutter 81 is disposed at the distal end of the other arm 132, although any number of tools, e.g., graspers, biopsy graspers, needle knives, snares, etc., may be utilized depending upon the desired procedure to be performed. Moreover, the tools 144 may alternatively be affixed upon the distal ends of tool arms 132 and atraumatic tips may be provided thereupon to prevent trauma to contacted tissue during endoluminal advancement.

It may be appreciated that the systems, methods and devices of the present invention are applicable to diagnostic and surgical procedures in any location within a body, particularly any natural or artificially created body cavity. Such locations may be disposed within the gastrointestinal tract, urology tract, peritoneal cavity, cardiovascular system, respiratory system, trachea, sinus cavity, female reproductive system and spinal canal, to name a few. Access to these locations may be achieved through any body lumen or through solid tissue. For example, the stomach may be accessed through an esophageal or a port access approach, the heart through a port access approach, the rectum through a rectal approach, the uterus through a vaginal approach, the spinal column through a port access approach and the abdomen through a port access approach.

A variety of procedures may be performed with the systems and devices of the present invention. The following procedures are intended to provide suggestions for use and are by no means considered to limit such usage: laryngoscopy, rhinoscopy, pharyngoscopy, bronchoscopy, sigmoidoscopy, colonoscopy, esophagogastroduodenoscopy (EGD) which enables the physician to look inside the esophagus, stomach, and duodenum.

In addition, endoscopic retrograde cholangiopancreatography (ERCP) may be achieved which enables the surgeon to diagnose disease in the liver, gallbladder, bile ducts, and pancreas. In combination with this process endoscopic sphincterotomy can be done for facilitating ductal stone removal. ERCP may be important for identification of abnormalities in the pancreatic and biliary ductal system. Other treatments include cholecystectomy (removal of diseased gallbladder), CBD exploration (for common bile duct stones), appendicectomy (removal of diseased appendix), hernia repair TAP, TEPP and other (all kinds of hernia), fundoplication and HISS procedures (for gastro esophageal reflux disease), repair of duodenal perforation, gastrostomy for palliative management of late stage upper G.I.T. carcinoma), selective vagotomy (for peptic ulcer disease), splenectomy (removal of diseased spleen), upper and lower G.I. endoscopies (diagnostic as well as therapeutic endoscopies), pyloroplastic procedures (for children's congenital deformities), colostomy, colectomy, adrenalectomy (removal of adrenal gland for pheochromocytoma), liver biopsy, gastrojejunostomy, subtotal liver resection, gastrectomy, small intestine partial resections (for infarction or stenosis or obstruction), adhesions removal, treatment of rectum prolaps, Heller's Myotomy, devascularization in portal hypertension, attaching a device to a tissue wall and local drug delivery to name a few.

As mentioned previously, elongate body 120 has a proximal end 122 and a distal end 124 terminating in a distal tip 126. Elongate body 120 may include one or more sections or portions of elongate body 120 in which each section may be configured to bend or articulate in a controlled manner. A first section along elongate body 120 may be adapted to be deflectable and/or steerable, shape-lockable, etc. A second section, which may be located distally of and optionally adjacent to the first section along elongate body 120, may be adapted to retroflex independent of in conjunction with the first section. In one variation, this second section may be laterally stabilized and deflectable in a single plane. An optional third section, which may be located distally of and optionally adjacent to the second section, may be adapted to be a steerable portion, e.g., steerable within any axial plane in a 360-degree circumference around the shaft.

When a third section is utilized as the most distal section along elongate body 120, such steerability may allow for movement of the distal tip of elongate body 120 in a variety of directions. Such sections will be further described below. It may be appreciated that the elongate body 120 may be comprised of any combination of sections and may include such sections in any arrangement. Likewise, the elongate body 120 may be comprised of any subset of the three sections, e.g., first section and third section, or simply a third section. Further, additional sections may be present other than the three sections described above. Furthermore, multiple sections of a given variety, e.g. multiple sections adapted to be articulated as second section above, may be provided. Finally, one or all three sections may be independently lockable, as will be described below.

Figure 18A:
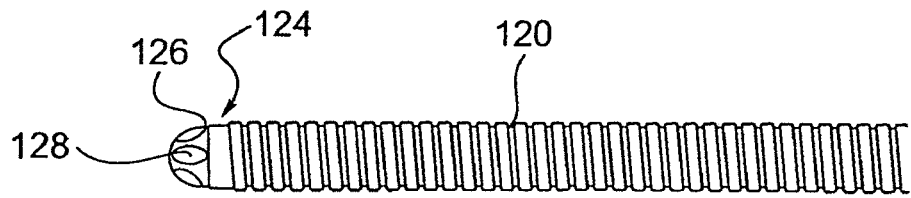
FIGS. 18A to 18C illustrate another variation of the elongate body having two adjacent sections which are articulatable relative to each other and which are also optionally rigidizable to retain a desired configuration.
Figure 18B:
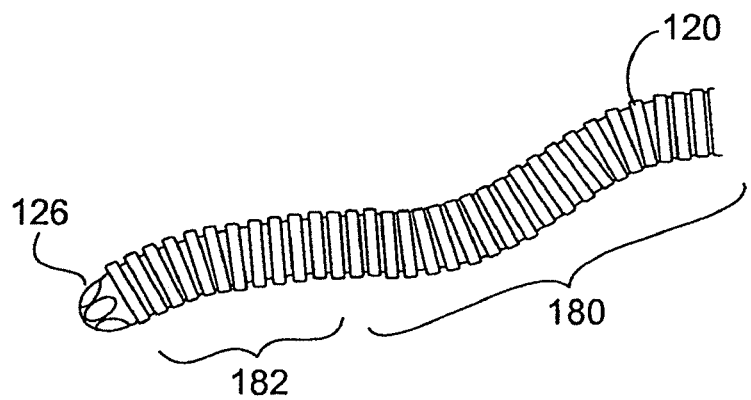
Figure 18C:
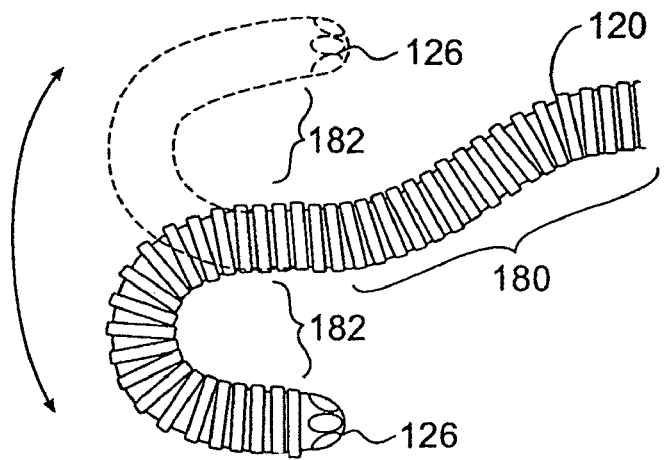

One variation of the elongate body 120 is illustrated in FIG. 18A in a straightened configuration. Only elongate body 120 is shown in these illustrations and the end effector assembly with off-axis tool arms and off-axis visualization has been omitted merely for the sake of clarity. Because the elongate body 120 is used to access an internal target location within a patient's body, elongate body 120 may include a deflectable and/or steerable shaft 120. Thus, FIG. 18B illustrates the elongate body 120 having various curvatures in its deflected or steered state. The elongate body 120 may be steerable so that the elongate body 120 may be advanced through unsupported anatomy and directed to desired locations within hollow body cavities. In this example, the elongate body 120 includes a first section 180 which is proximal to a second section 182, as indicated in FIG. 18B. Although both sections 180, 182 may be steerable, first section 180 may be adapted to lock its configuration while the second section 182 is further articulatable, as illustrated in FIG. 18C where first section 180 is shown in a locked position and the second section 182 is shown in various retroflexed positions.

When retroflexed, second section 182 may be curved or curled laterally outwardly so that the distal tip 126 is directable toward the proximal end 122 of the elongate body 120. Moreover, the second section 182 may be configured to form an arc which traverses approximately 270 degrees, if so desired. Optionally, the second section 182 also may be locked, either when retroflexed or in any other position. As should be understood, first section 180 optionally may not be steerable or lockable. For example, section 180 may comprise a passive tube extrusion.

Figure 18D:
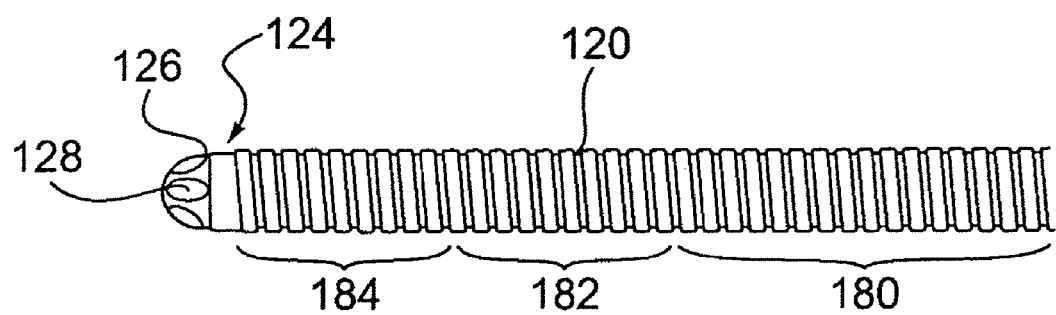
FIGS. 18D and 18E illustrate yet another variation of the elongate body having three adjacent sections which are all articulatable relative to each other and which are also optionally rigidizable to retain a desired configuration.
Figure 18E:
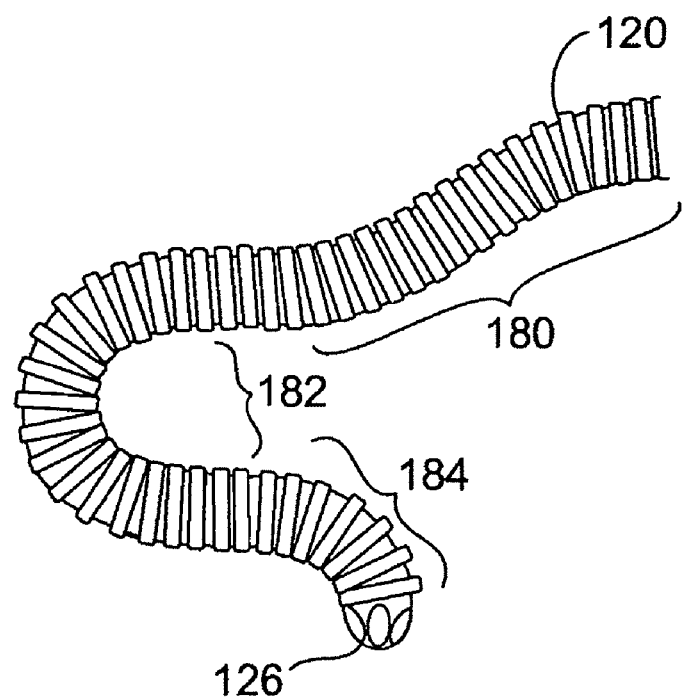

A further variation of elongate body 120 is illustrated in FIG. 18D, in a straight configuration, and in FIG. 18E, in a deflected or steered state having various curvatures. In this variation, elongate body 120 may include a first section 180 proximal to a second section 182, which is proximal to a third section 184. First section 180 may be flexible or semi-flexible, e.g. such that the section 180 is primarily moveable through supported anatomy, or is moveable through unsupported anatomy via one or more stiffening members disposed within or about the section. The first section 180 may be comprised of links or nestable elements which may enable the first section 180 to alternate between a flexible state and a rigidized stated.

Optionally, first section 180 may comprise locking features for locking the section in place while the second section 182 is further articulated. Typically, the second section 182 may be configured to be adapted for retroflexion. In retroflexion, as illustrated in FIG. 18E, second section 182 may be curved or curled laterally and outwardly so that a portion of second section 182 is directed toward the proximal end 122 of the elongate body 120. It may be appreciated that second section 182 may be retroflexed in any desired direction. Optionally, second section 182 may also be locked, either in retroflexion or in any other position.

Further, first section 180 and second section 182 may be locked in place while third section 184 is further articulated. Such articulation is typically achieved by steering, such as with the use of pullwires. The distal tip 126 preferably may be steered in any direction relative to second section 182. For example, with second section 182 defining an axis, third section 184 may move within an axial plane, such as in a wagging motion. The third section 184 may move through any axial plane in a 360 degree circumference around the axis; thus, third section 184 may be articulated to wag in any direction. Further, third section 184 may be further steerable to direct the distal tip 126 within any plane perpendicular to any of the axial planes. Thus, rather than wagging, the distal tip 126 may be moved in a radial manner, such as to form a circle around the axis. FIG. 18E illustrates third section 184 steered into an articulated position within an axial plane.

Figure 18F:
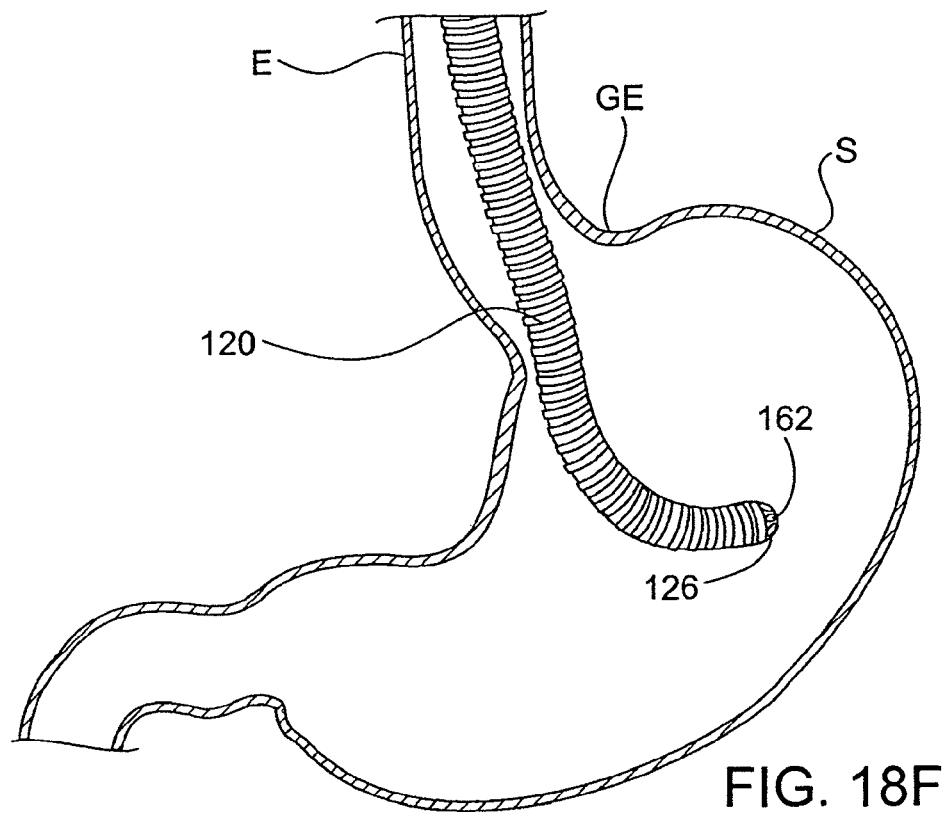
FIGS. 18F to 18H illustrate an example of a three-sectioned variation of the elongate body being advanced transesophageally into the stomach and articulated to position its distal end near or adjacent to the gastroesophageal junction.
Figure 18G:
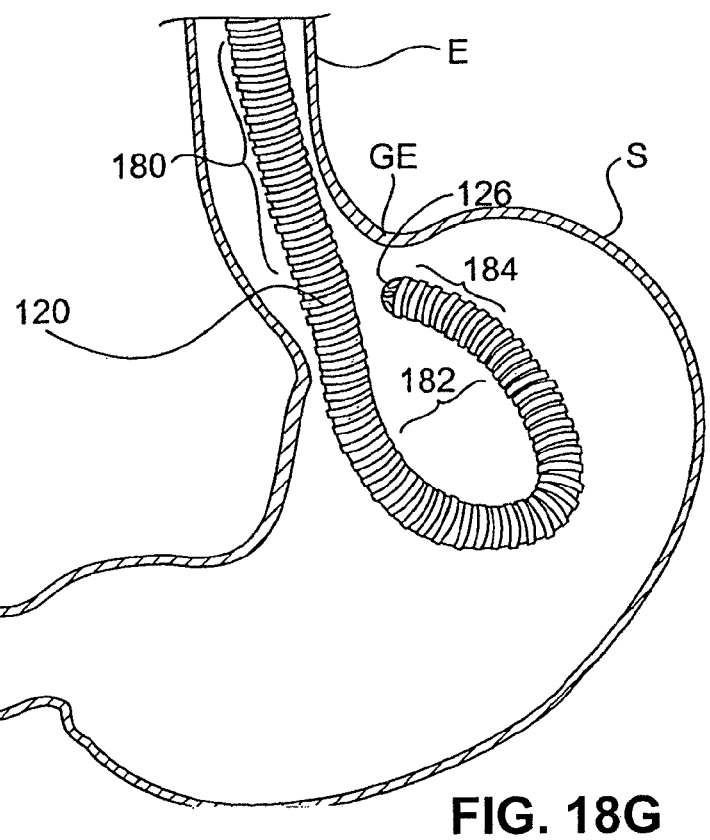
Figure 18H:
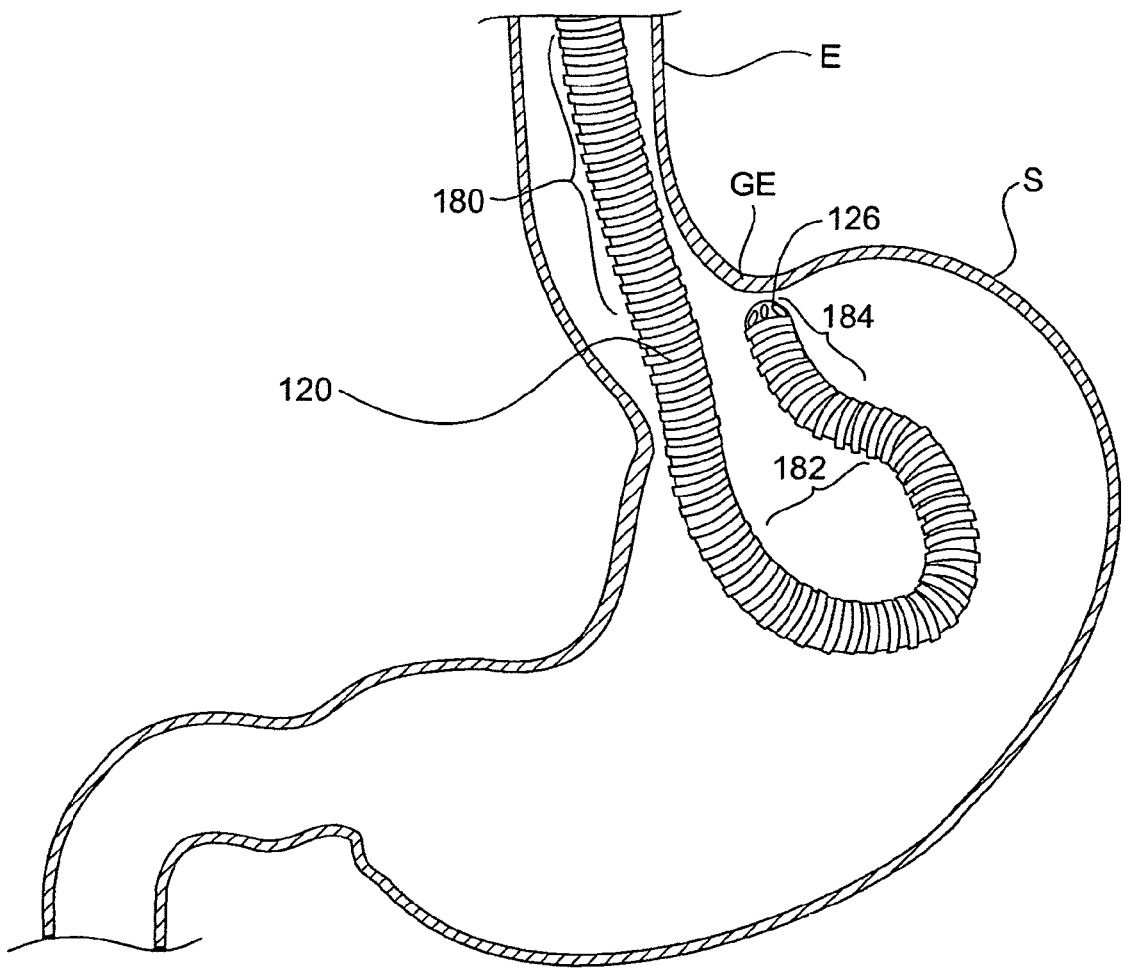

The variation of elongate body 120 illustrated in FIGS. 18D and 18E having three sections 180, 182, 184 with varying movement capabilities are shown in FIGS. 18F and 18H in an example of positioning elongate body 120 within a stomach S through an esophagus E. Since elongate body 120 may be deflectable and at least some of the sections 180, 182, 184 may be steerable, elongate body 120 may be advanced through the tortuous or unpredictably supported anatomy of the esophagus and into the stomach S while reducing a risk of distending or injuring the organs, as shown in FIG. 18F. Once the distal tip 126 has entered the stomach, second section 182 may be retroflexed as illustrated in FIG. 18G. During retroflexion, distal tip 126 may traverse an arc having a continuous radius of curvature, e.g., approximately 270 degrees with a radius of curvature between about 5 to 10 cm. By retroflexing, distal tip 126 may be directed back towards first section 180 near and inferior to gastroesophageal junction GE. Second section 182 may be actively retroflexed, e.g. via pullwires, or it may be passively retroflexed by deflecting the section off a wall of stomach S while advancing elongate body 120.

Second section 182 may be configured to be shape-lockable in the retroflexed configuration. The distal tip 126 may then be further articulated and directed to a specific target location within the stomach. For example, as shown in FIG. 18H, the distal tip 126 may be steered toward a particular portion of the gastroesophageal junction GE. Third section 184 may optionally be shape-locked in this configuration. Off-axis tools and off-axis visualization may then be deployed through or from elongate body 120, as described above, to perform any number of procedures.

Figure 18I:
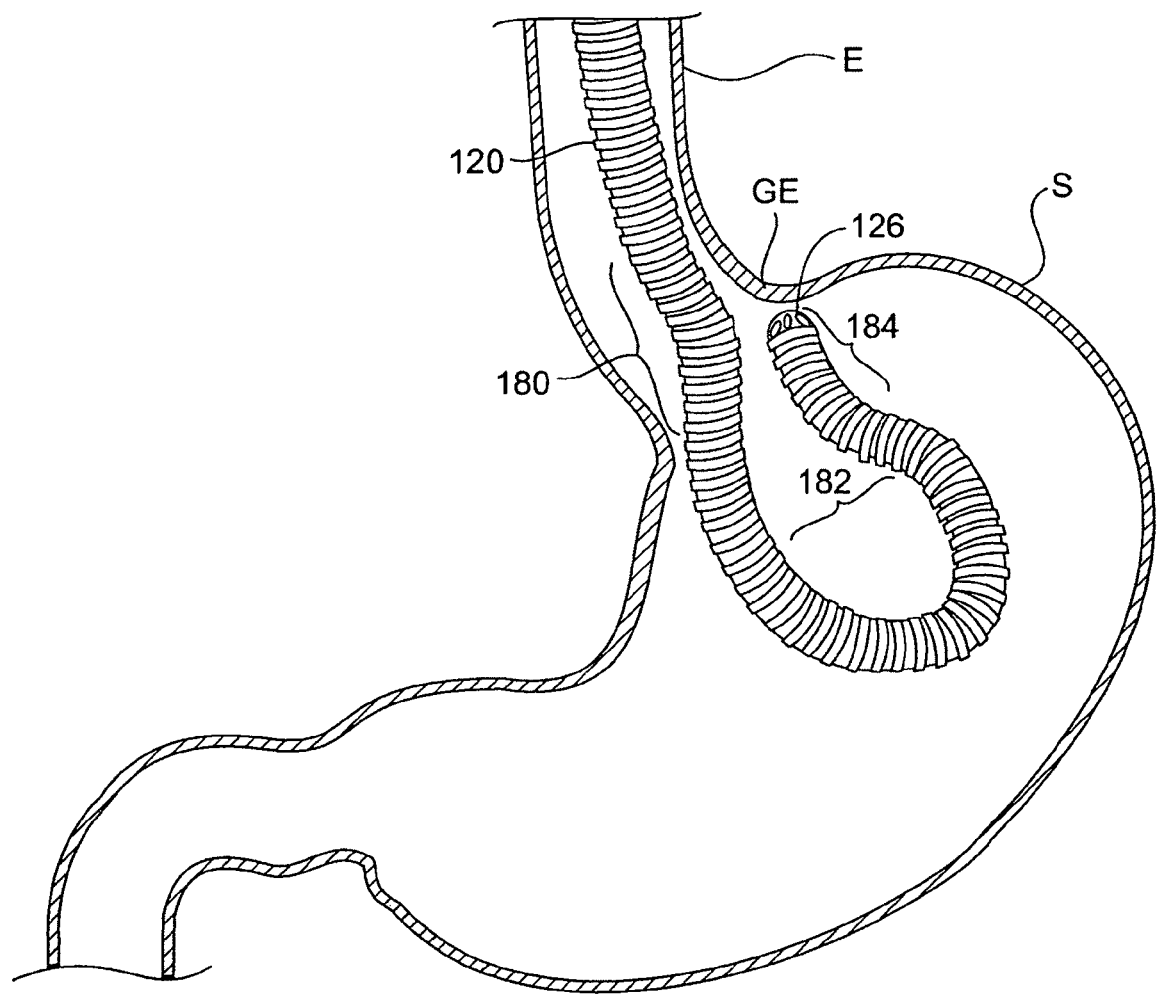
FIG. 18I illustrates another example of FIGS. 18F to 18H in which at least one the bendable sections may be articulated in an opposing direction relative to the remaining two bendable sections to further articulate the elongate body within the stomach.

FIG. 18I shows yet another example in which elongate body 120 may be articulated in a manner similar as shown above in FIG. 18H. In this variation, elongate body may comprise a first section 180 which is configured to bend or curve in any number of directions. One particular variation may configure first section 180 to articulate in a direction opposite to a direction in which second section 182 bends. This opposed articulation may result in an elongate body 120 which conforms into a question-mark shape to facilitate positioning of third section 184 within stomach S, particularly for procedures which may be performed near or at the gastroesophageal junction GE. First section 180 may be configured to automatically conform into its opposed configuration upon rigidizing elongate body 120 or it may alternatively be articulated into its configuration by the physician.

Figure 19:
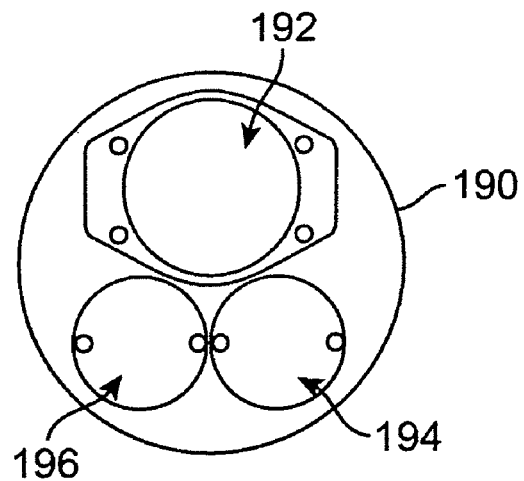
FIG. 19 shows an end view of one variation of the cross-section of the elongate body providing two lumens for their respective tool arms and a single lumen for the visualization apparatus or endoscope.
Figure 20A:
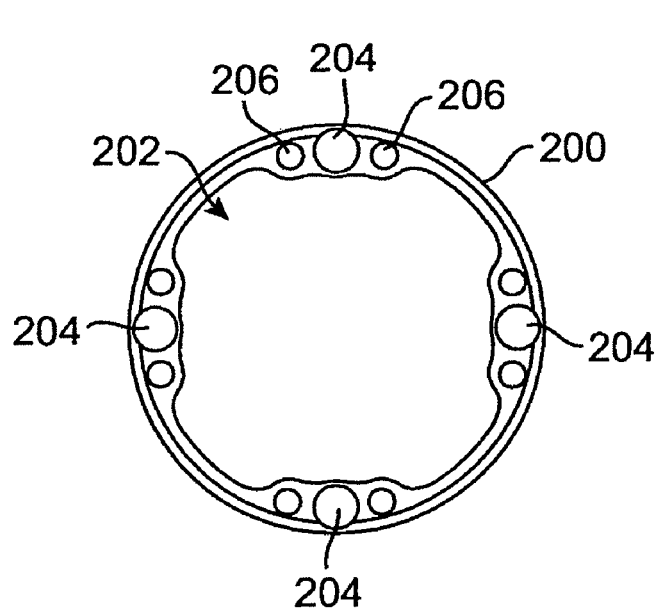
FIGS. 20A and 20B show end and side views of an example of an individual link through which the working lumens may be positioned.
Figure 20B:
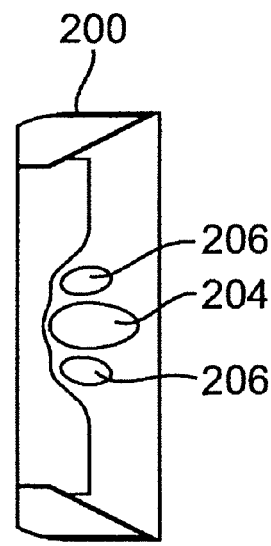

Turning now to the construction of the individual links which may form elongate body, FIGS. 19, 20A, and 20B show examples of link variations which may be utilized. FIGS. 20A and 20B show end and side views, respectively, of one variation of a link which may be utilized for construction of elongate body 120. An exemplary elongate body link 200 may be comprised generally of an open lumen 202 through any number of separate lumens, e.g., tool arm lumens, visualization lumens, etc., may be routed through.

The periphery defining open lumen 202 may define a number of openings for passage of various control wires, cables, optical fibers, etc. For instance, control wire lumens 204 may be formed at uniform intervals around the link 200, e.g., in this example, there are four control wire lumens 204 shown uniformly positioned about the link 200, although any number of lumens may be utilized as practicable and depending upon the desired articulation of elongate body 120. Elongate body link 200 may also comprise a number of auxiliary control lumens 206 spaced around body link 200 and adjacent to control wire lumens 204. Any number of biocompatible materials may be utilized in the construction of links 200, e.g., titanium, stainless steel, etc.

Aside from the elongate body links 200, one variation for a terminal link 190 may be seen in FIG. 19. Terminal link 190 may be utilized as an interface link between elongate body 120 and the distal end effector assembly 12. In the variation shown in FIG. 19, three lumens are utilized in terminal link 190 for a visualization lumen 192 and two tool arm channels 194, 196. In other variations for the terminal link, additional lumens may be defined through the link. In the case of an end effector having tools and a visualization lumen attached or coupled directly to the distal end of elongate body 120, the off-axis tools arms and off-axis articulatable lumen may be connected directly to terminal link 190.

Further examples and details of link construction may be seen in further detail in U.S. Pat. Pubs. 2004/0138525 A1; 2004/0138529 A1; 2004/0249367 A1; and 2005/0065397 A1, each of which has been incorporated above herein by reference.

Figure 21A:
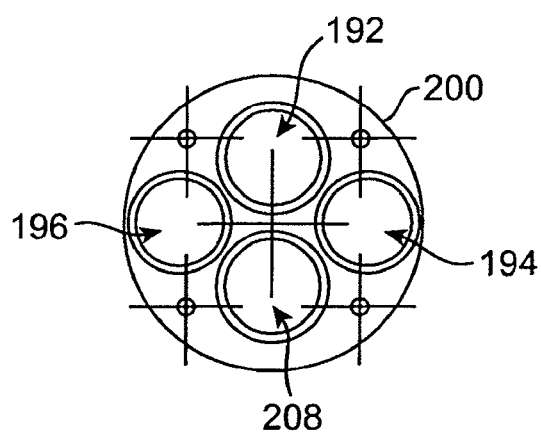
FIGS. 21A and 21B show other variations of the cross-section of the elongate body providing two lumens for their respective tool arms, a lumen for visualization, and an auxiliary lumen for an additional instrument to be passed therethrough.
Figure 21B:
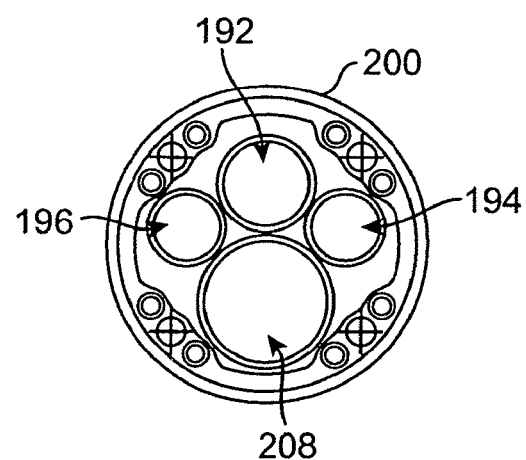

Arrangement of the individual lumens routed through elongate body 120 may be accomplished in any number of ways. For example, FIGS. 21A and 21B show end views of possible lumen arrangements where four lumens are utilized through elongate body 120. The variation in FIG. 21A shows elongate body link 200 where visualization lumen 192 and auxiliary instrument lumen 208 may be of a similar size diameter. Lumens 192, 208 may be positioned adjacently to one another with tool arm channels 194, 196 positioned on either side of lumens 192, 208.

Figure 21C:
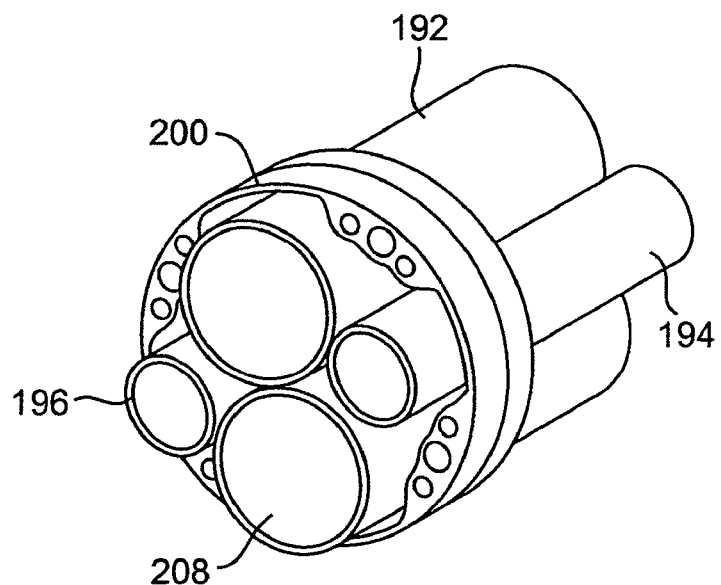
FIG. 21C shows a perspective view of an example for lumen positioning relative to one another for the configuration of FIG. 21A.

In another variation, auxiliary instrument lumen 208 may be adjacently positioned and larger than visualization lumen 192, in which case tool arm channels 194, 196 may be positioned on either side of visualization lumen 192. In the spaces or interstices through link 200 between the visualization lumen 192, auxiliary instrument lumen 208, or either tool arm channels 194, 196, multiple smaller diameter lumens may be routed through for any number of additional features, e.g., insufflation, suction, fluid delivery, etc. FIG. 21C shows a perspective view of a single elongate body link 200 with visualization lumen 192, auxiliary instrument lumen 200, and tool arm channels 194, 196 routed therethrough.

Figure 22A:
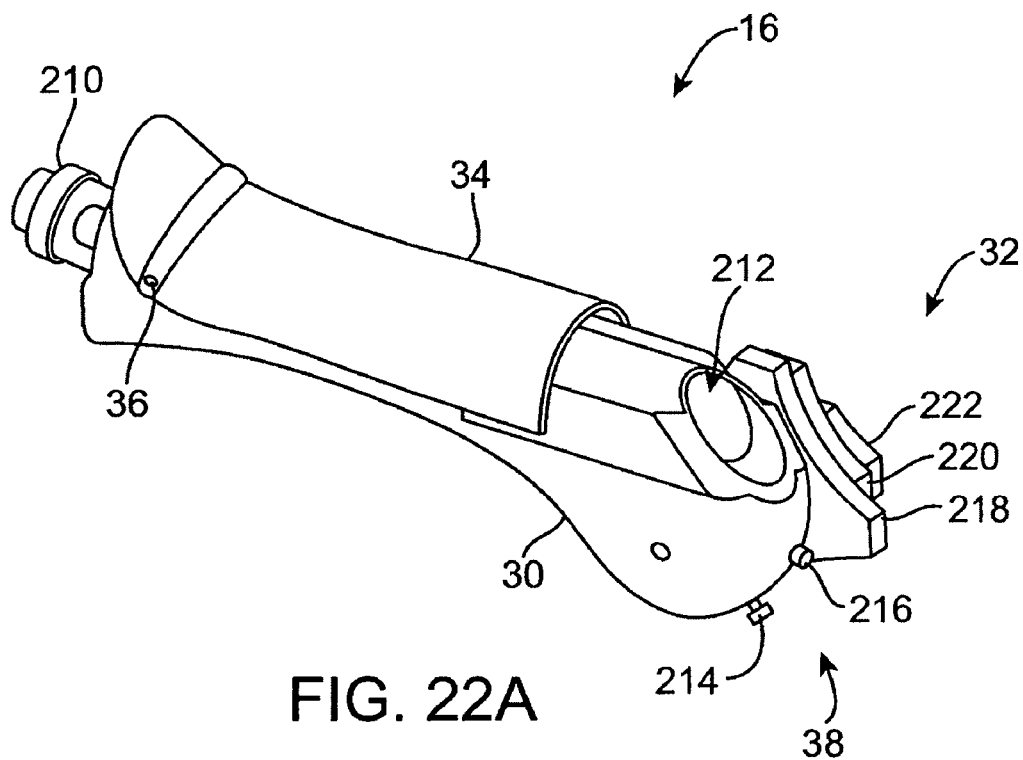
FIGS. 22A and 22B show perspective detail views of an example of the handle assembly optionally having a rigidizable elongate body; in a first configuration in FIG. 22A, rigidizing control is actuated or depressed to rigidize or shapelock the elongate body and in a second configuration in FIG. 22B where rigidizing control may be released to place the elongate body in a flexible state.
Figure 22B:
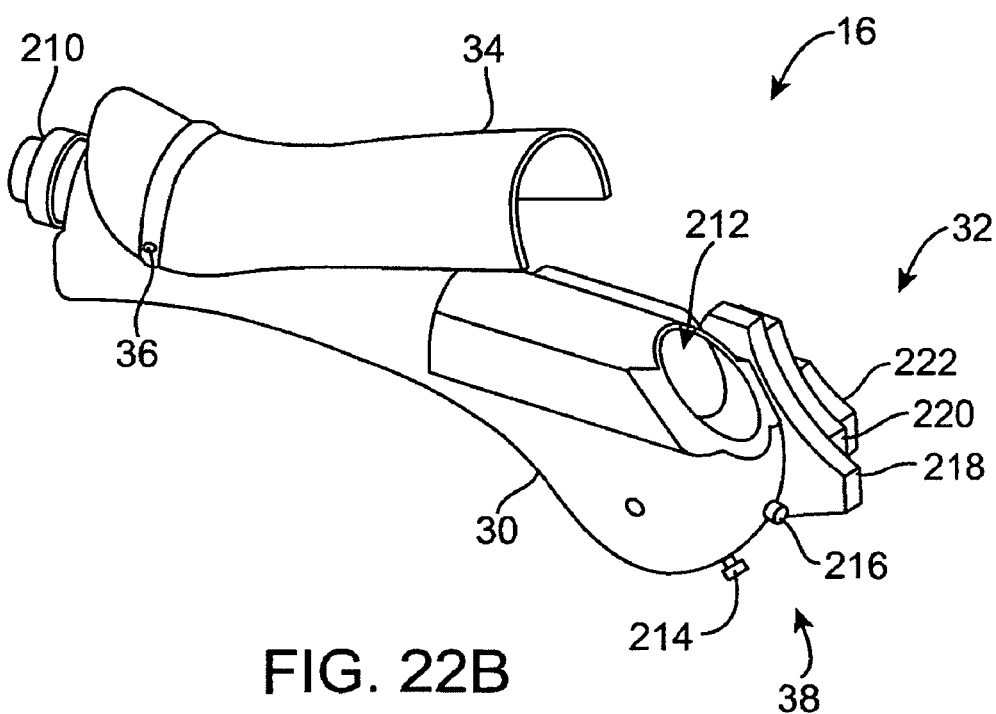

Turning now to the handle for endoluminal assembly 10, one variation of handle assembly may be seen in the perspective views of FIGS. 22A and 22B. Handle assembly 16 may generally comprise, in one variation, handle 30 which is connectable to the proximal end of elongate body 120 via elongate body interface 210. Coupling between the elongate body 120 and interface 210 may be accomplished in a number of different ways, e.g., interference fit, detents, etc., or the proximal link of elongate body 120 and interface 210 may be held adjacently to one another by routing control wires from handle 30 through interface 210 and into elongate body 120.

Interface 210 may also be adapted to travel proximally or distally relative to handle 30 when rigidizing control 34 is actuated about pivot 36 to actuate a rigidized or shape-locked configuration in elongate body 120. An example is shown in FIG. 22A where control 34 is depressed against handle 30 to advance interface 210 distally from handle 30. This distal movement of interface 210 compresses the links throughout elongate body 120 to rigidize its configuration. Likewise, as shown in FIG. 22B, when control 34 is released or pivoted away from handle 30, interface 210 may be configured to travel proximally relative to handle 30 such that a connected elongate body 120 is released into a flexible state by decompression of its links. Further details of mechanisms and methods for link compression for actuating a rigid shape of elongate body 120 may be seen further detail in U.S. Pat. Nos. 6,783,491; 6,790,173; and 6,837,847, each of which has been incorporated by reference above.

Handle 30 may also define an elongate body entry lumen 212 which may be defined near or at a proximal end of handle 30. Entry lumen 212 may define one or more openings for the passage of any of the tools and instruments, as described herein, through handle 30 and into elongate body 120. One or more ports, e.g., ports 214, 216, which are in fluid communication with one or more lumens routed through elongate body 120, as described above, may also be positioned on handle 30 and used for various purposes, e.g., insufflation, suction, irrigation, etc.

Figure 22C:
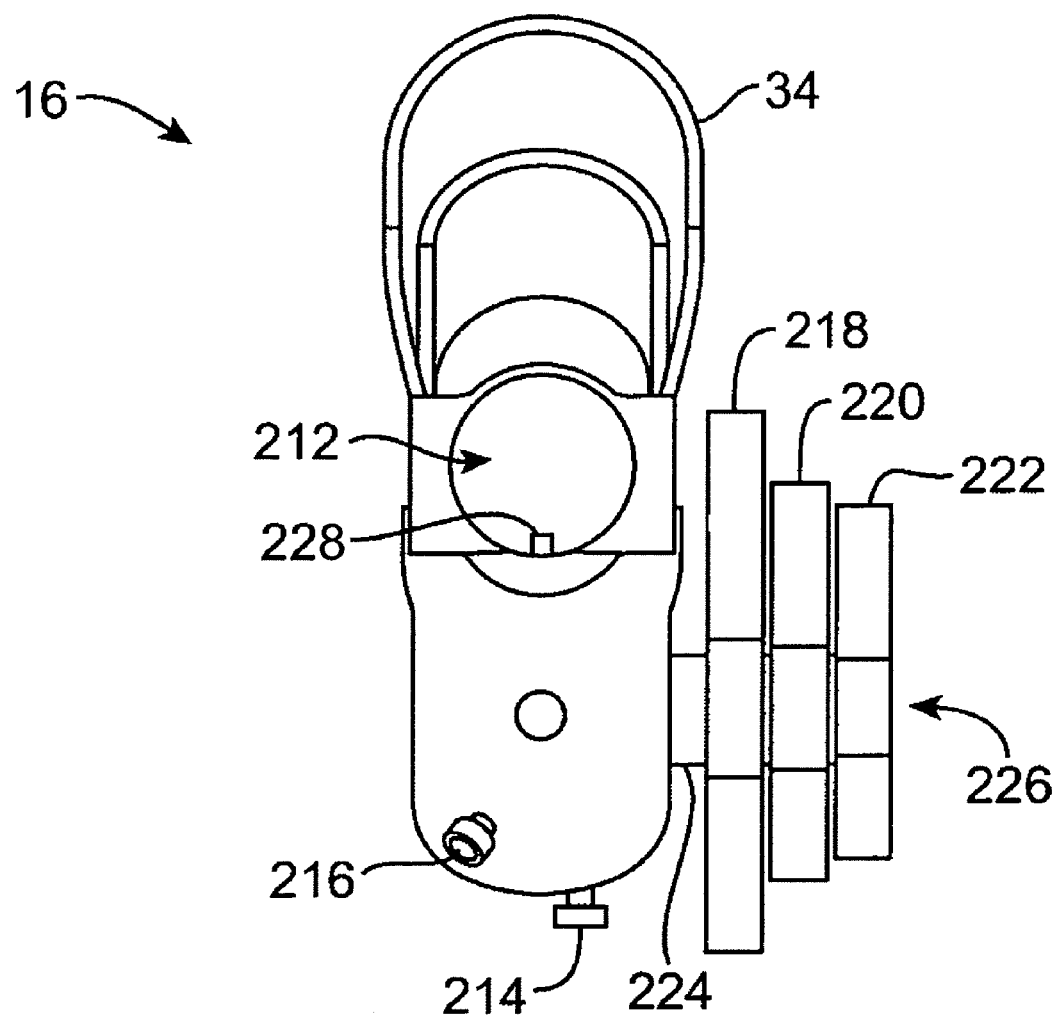
FIG. 22C shows an end view of the handle of FIG. 22B revealing the open lumen for the passage of tools, instruments, and/or visualization fibers, etc., therethrough.

Additionally, handle 30 may further include a number of articulation or manipulation controls 32 for controlling elongate body 120 and/or end effector assembly 12. As shown in FIGS. 22A and 22B, control assembly 32 in this variation may include a first control 218 for manipulating or articulating first section 180; a second control 220 for manipulating or articulating second section 182 in a first plane; and a third control 222 for manipulating or articulating second section 182 in a second plane. In this variation of handle assembly 16, control assembly 32 is configured to have several control wheels which are adjacently positioned relative to one another over a common control axis 224, as shown in the end view of handle assembly 16 in FIG. 22C. Control assembly 32 may also include a locking mechanism 226 which may be configured to lock each of the controls 218, 220, 222 individually or simultaneously to lock a configuration of each section.

Moreover, each of the controls 218, 220, 222 may be configured to articulate their respective sections along elongate body 120 even when rigidizing control 34 has been articulated to rigidize a shape of the elongate body 120. In alternative variations, handle assembly 16 may include additional controls for additional sections of elongate body 120. Moreover, alternative configurations for the control assembly 32 may also include articulating levers or sliding mechanisms along handle 30 as control wheels are intended to be merely illustrative of the type of control mechanisms which may be utilized.

Figure 23:
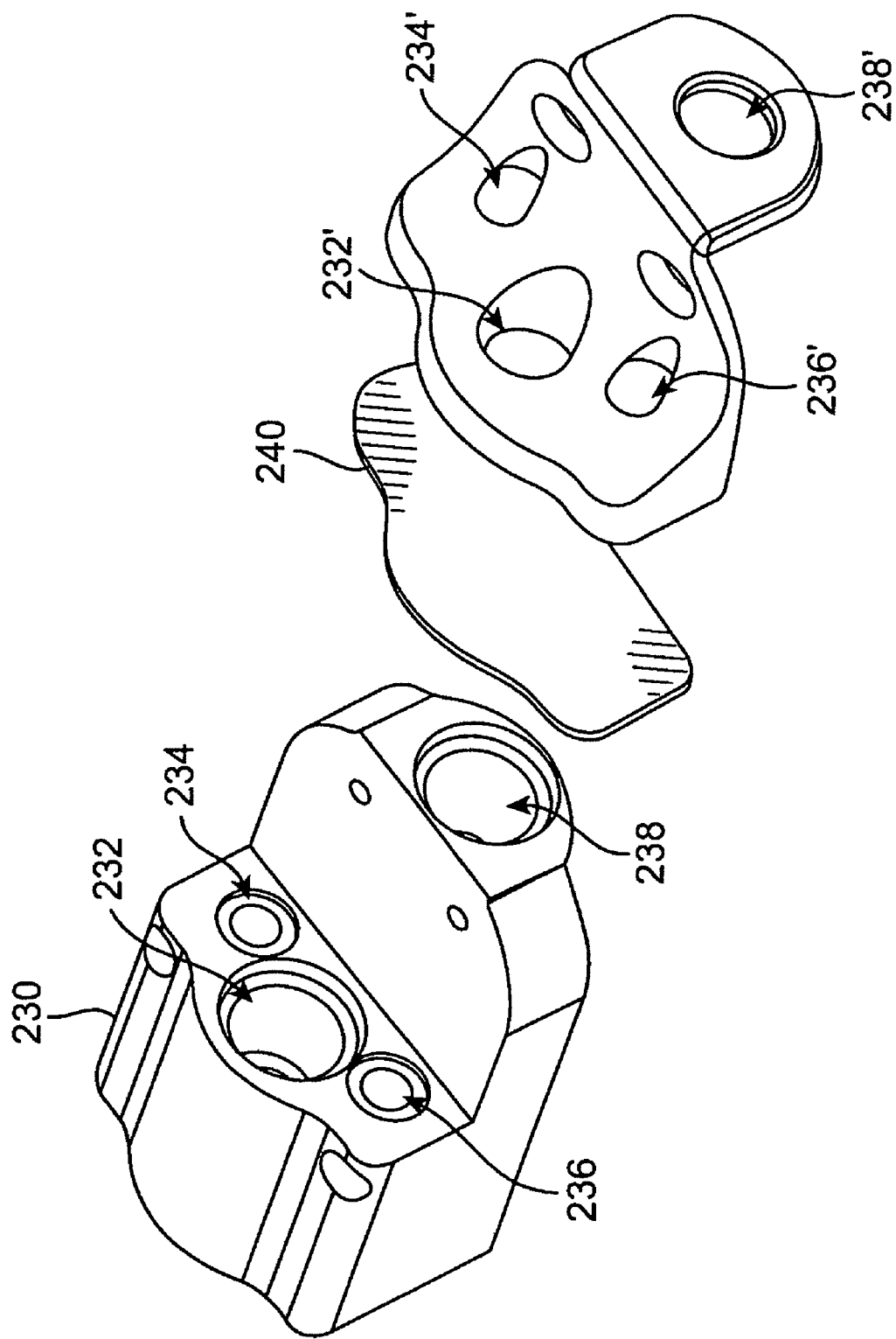
FIG. 23 shows an exploded perspective view of a sealable or gasketed port assembly which may be attached to the handle for passing tools and/or instruments therethrough while maintaining a seal.

As mentioned above, entry lumen 212 may define one or more openings for the passage of any of the tools and instruments, as described herein, through handle 30 and into elongate body 120. To manage the insertion and sealing of multiple lumens routed through handle assembly 16 and elongate body 120, a port assembly may be connected or attached to handle 30 proximally of entry lumen 212 in a fluid-tight seal. A port assembly alignment post 228 for aligning such a port assembly may be seen in the end view of FIG. 22C. An example of such a port assembly 230 is shown in the perspective view of FIG. 23. Port assembly 230 may be seen having a visualization port lumen 232 for the insertion and passage of a visualization tool, as well as tool ports 234, 236 on either side of visualization port lumen 232 for the insertion of tools, as described above. Auxiliary instrument port 238 may also be seen on port assembly 230.

To maintain a fluid-tight seal through handle assembly 16 and elongate body 120 during instrument insertion, movement, and withdrawal in the patient body, a removable gasket 240 made from a compliant material, e.g., polyurethane, rubber, silicon, etc., may be positioned between ports 232, 234, 236, 238 of port assembly 230 and a retainer for securely retaining the gasket against assembly 230. The retainer may also have ports 232', 234', 236', 238' defined therethrough for alignment with their respective ports in assembly 230 for passage of the tools or instruments.

Figure 24A:
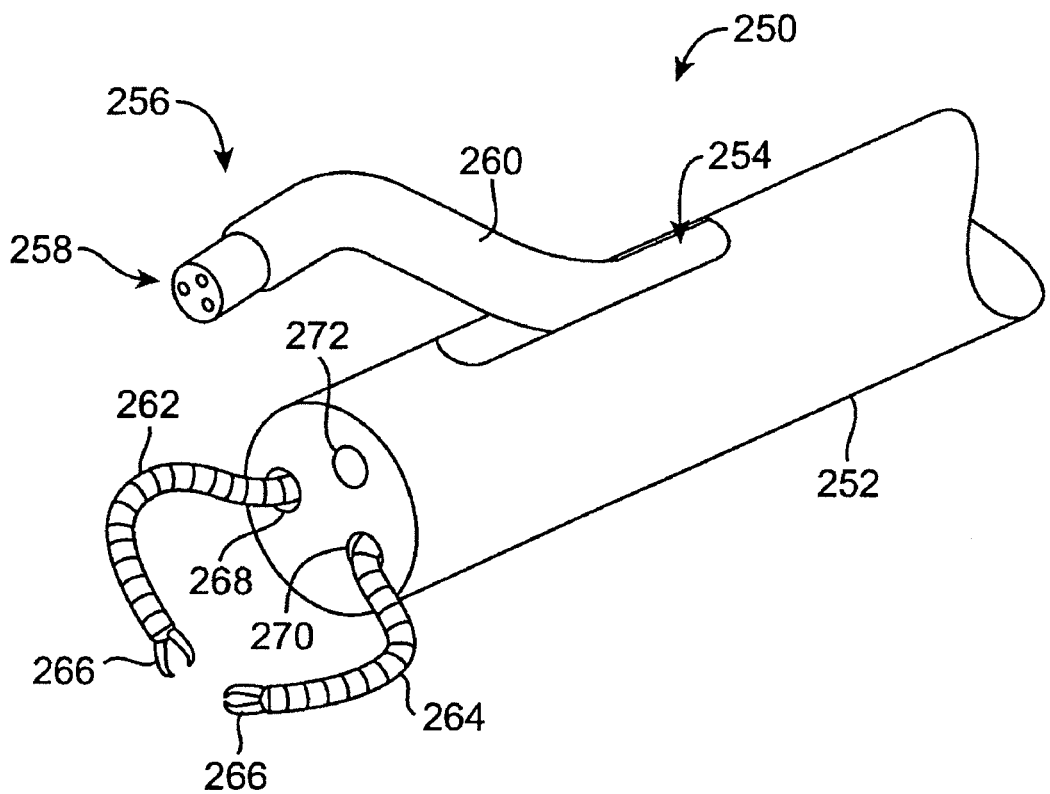
FIGS. 24A and 24B illustrate perspective and partial cross-sectional side views, respectively, of yet another variation of the endoluminal tissue treatment assembly having an endoscope which may be passed through an opening in the elongate body, which is optionally rigidizable, for providing off-axis visualization.
Figure 24B:
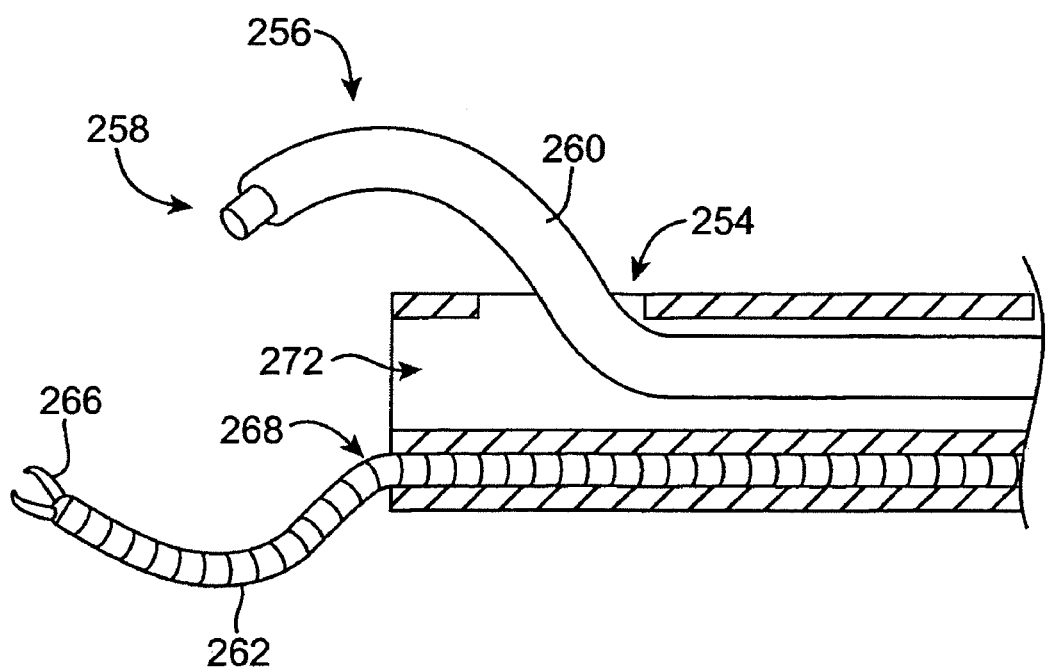

Other configurations for the end effector assembly may also be made utilizing a number of variations. FIGS. 24A and 24B show perspective and partial cross-sectional views, respectively, of a variation of end effector assembly 250. As illustrated, elongate body 252 may be a shape-lockable or rigidizable body which may be steerable or non-steerable, as described above, or it may generally be a passively flexible body which may be steerable or non-steerable as well. In either case, an opening 254 may be defined through an outer surface near or at a distal end of elongate body 252.

A visualization assembly 256, which may generally comprise an endoscope 258 having a bendable or flexible section 260 near or at its distal end, may be advanced through an endoscope or auxiliary instrument lumen 272 defined through elongate body 252 and advanced through opening 254. Endoscope 258 may be advanced through opening 254 such that its flexible section 260 enables the end of endoscope 258 to be positioned in an off-axis configuration distal of elongate body 252. Alternatively, endoscope 258 may be advanced entirely through lumen 272 such that it is disposed at the distal end of lumen 272 or projects distally therefrom to provide visualization of the tissue region of interest. First and second articulatable tool arms 262, 264 having one or more tools 266 upon their respective distal ends, as described above, may also be advanced through respective first and second tool lumens 268, 270. Tool arms 262, 264 may be disposed distally of elongate body 252 such that they are within the visualization field provided by the off-axis endoscope 258.

Figure 25A:
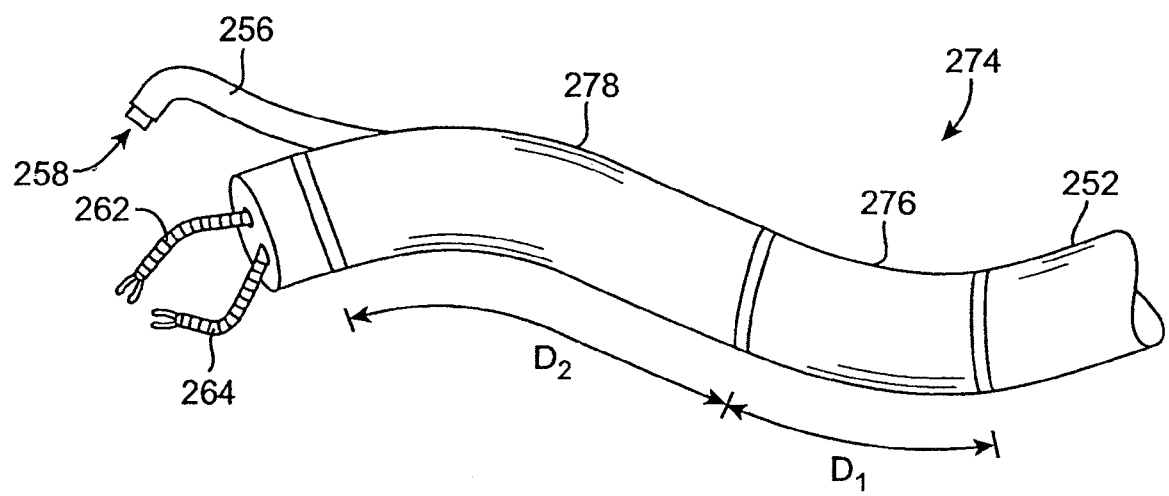
FIGS. 25A and 25B illustrate yet another variation where the articulatable sections of the elongate body may be configured to have different lengths.
Figure 25B:
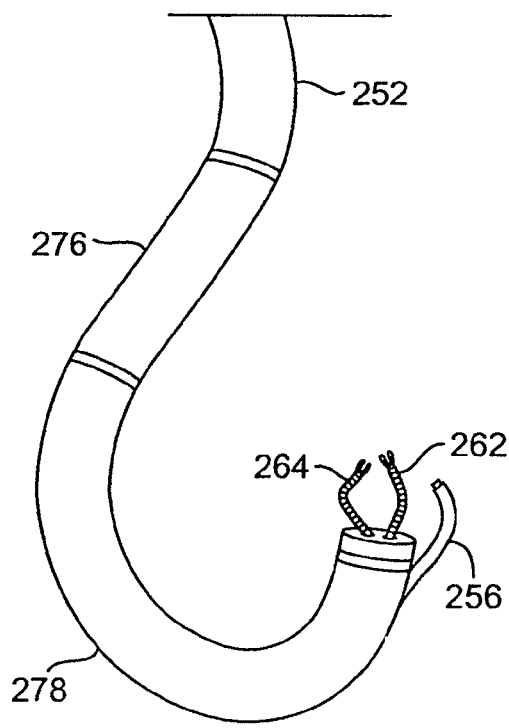

In another variation as shown in FIGS. 25A and 25B, elongate body 274 may comprise bendable or articulatable sections of varying lengths. Elongate body 274 in this variation may be shape-lockable or rigidizable along its length, as above, or it may have a passively flexible length. For example, elongate body 252 may have a first section 276 having a length D1 and a second section 278 having a length D2 located distally of first section 276. In the example shown, the length D1 of first section 276 may be shorter than the length D2 of second section 278, although the length of D1 may be longer than D2 in another alternative. Moreover, in yet another alternative, the lengths D1 and D2 may be equal. In the variation shown, having a length of D1 shorter than length D2 may allow for the end effector assembly to be articulated into a variety of configurations, especially if first section 276 is articulated in a direction opposite to a direction in which second section 278 is articulated, as shown in FIG. 25B. Any of the end effector assemblies described herein may be utilized with elongate body 252 having various lengths of sections 276, 278.

Figure 26:
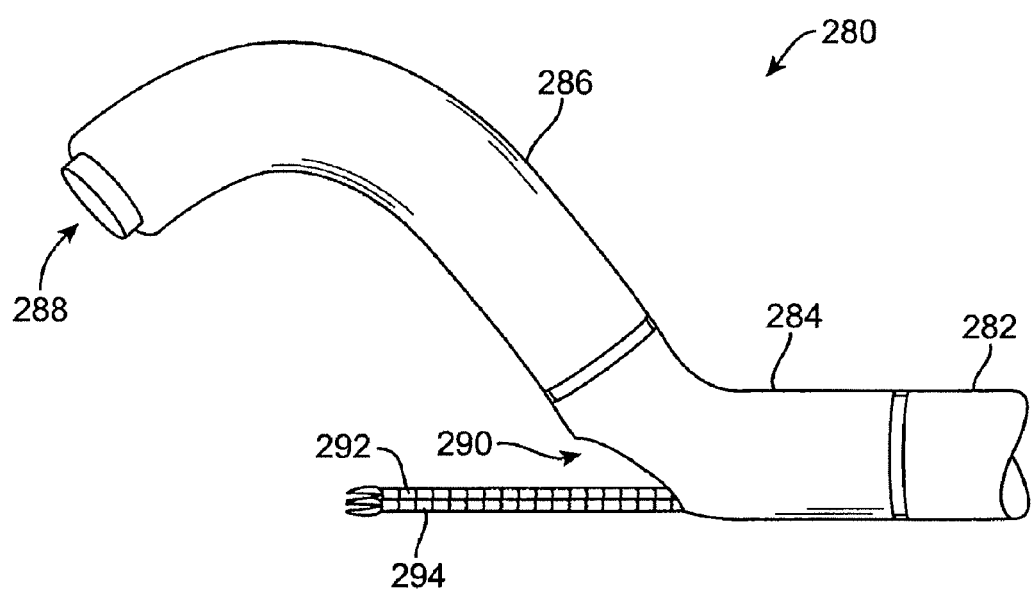
FIG. 26 shows another variation in which the articulatable tools may be passed through an opening defined along the elongate body which also has an articulatable distal portion to provide for off-axis visualization.

FIG. 26 shows a side profile of end effector assembly 280 in yet another variation. As shown, end effector assembly 280 may have an optionally shape-lockable elongate body 282 with articulatable first section 284 and second section 286. Second section 286 may be articulatable into an off-axis configuration such that an imager 288 positioned at its distal end may become positioned to view a region of interest accessible by first and second tool arms 292, 294, which may be passed through elongate body 282 and through opening 290 defined in first section 284 into the field-of-view provided by off-axis imager 288. Tool arms 292, 294 may be articulatable tool arms, as described above, or they may comprise any manner of conventional in-line tools.

Figure 27A:
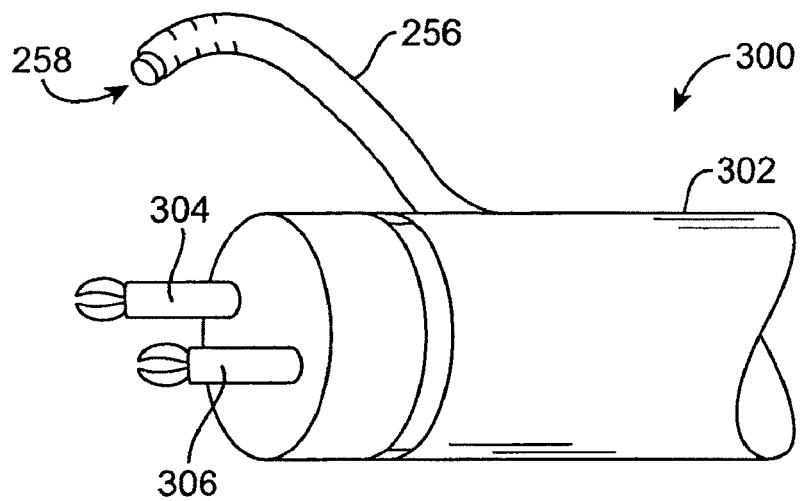
FIGS. 27A to 27C show yet another variation in which the tool arms may be configured to have predetermined configurations once advanced distally of the elongate body.
Figure 27B:
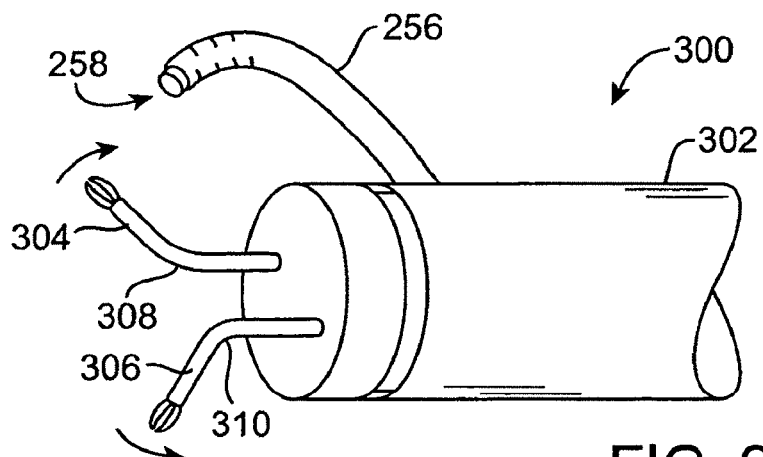
Figure 27C:
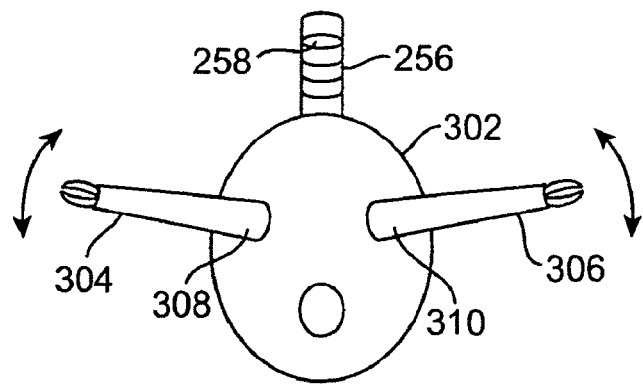

In yet another variation, FIGS. 27A and 27B show perspective views of end effector assembly 300 which may optionally comprise a shape-lockable elongate body 302 with off-axis visualization assembly 256, as above. In this variation, first and second tool arms 304, 306, respectively, may comprise arm members each having a first and second preset bending portion 308, 310, respectively, each configured to bend at a preset angle once free from the constraints of the tool lumens, as shown in FIG. 27B. Once unconstrained, tools arms 304, 306 may be rotated about its longitudinal axis, as shown in FIG. 27C, to accomplish any number of procedures on the tissue while visualized via off-axis endoscope 258. Tool arms 304, 306 may be fabricated from shape memory alloys, such as a Nickel-Titanium alloy, or from spring stainless steels, or any other suitable material which may allow for the tools arms 304, 306 to reconfigure itself from a first low-profile configuration to an off-axis deployment configuration.

Figure 27D:
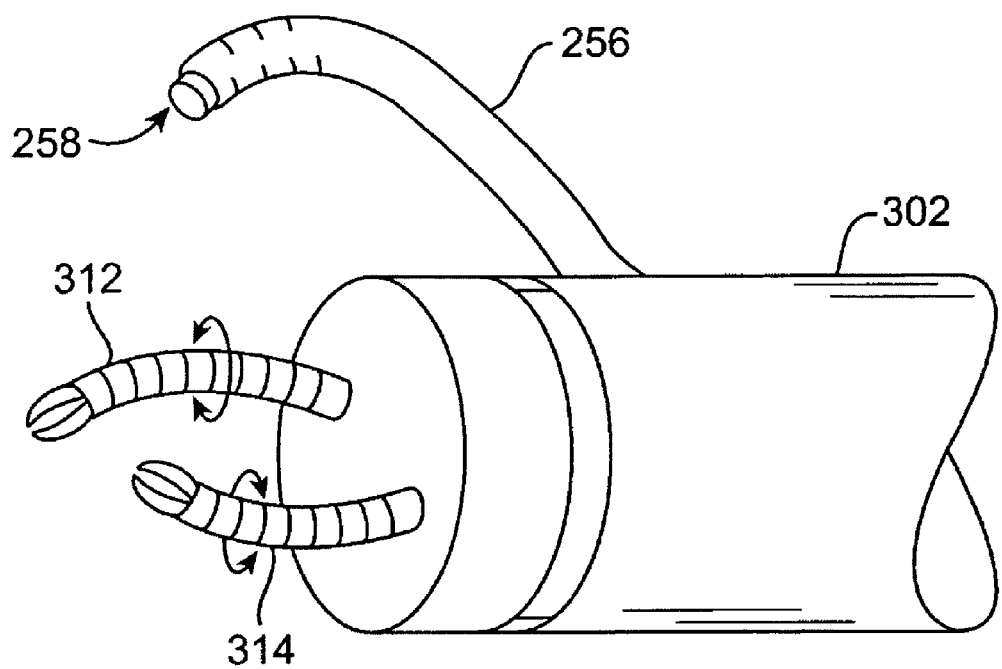
FIG. 27D shows yet another variation in which the articulatable tool arms may be freely rotated relative to the elongate body.

FIG. 27D shows a perspective view of yet another variation in which elongate body 302 may have first and second articulatable tool arms 312, 314 which are freely rotatable about their respective longitudinal axes. Visualization assembly 256 may comprise any of the variations described above, particularly the variation as described for FIGS. 24A and 24B.

Figure 28:
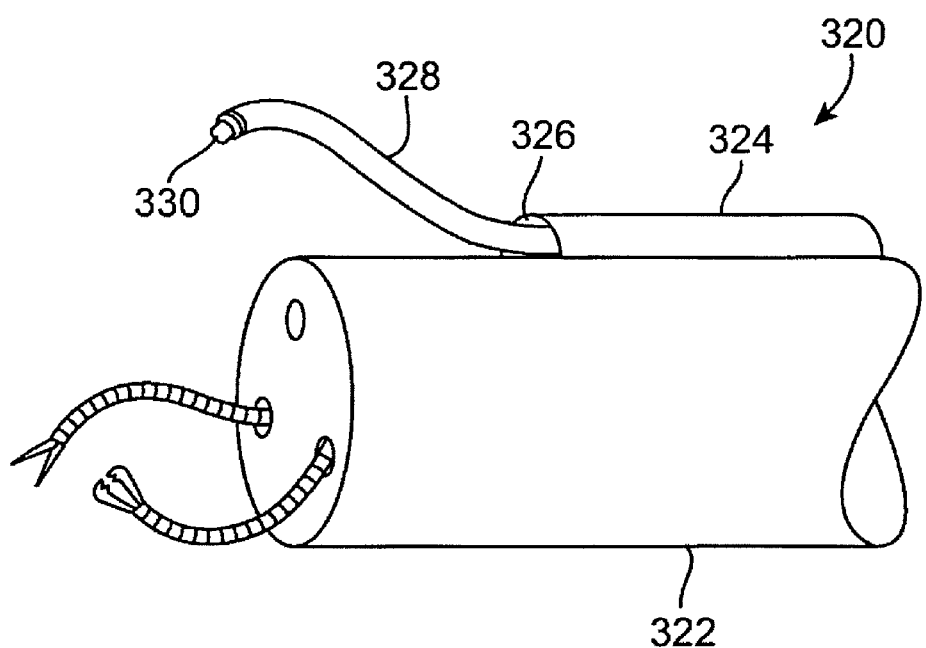
FIG. 28 shows yet another variation in which an imaging chip, e.g., a CCD chip, may be disposed upon the end of a guidewire having a predetermined configuration to provide for visualization of the tissue region; the imaging chip may transmit its images via wire through the guidewire or wirelessly to a receiver located externally of a patient body.

FIG. 28 shows a perspective view of another variation of end effector assembly 320 in which optionally shape-lockable elongate body 322 may comprise a separate visualization lumen 324 having a lumen opening 326 through which a guidewire 328 having a preset configuration may be advanced. Visualization lumen 324 may be integrated with elongate body 322 or separately attached to an outer surface of elongate body 322. Guidewire 328 may be comprised of a shape memory alloy, as above, and carry an imaging chip 330, e.g., a CCD imager, on a distal end of the guidewire 328. Guidewire 328 may be preset to reconfigure itself into an off-axis configuration to provide the off-axis visualization distally of elongate body 322, as shown. Furthermore, imaging chip 330 may be connected via wires through guidewire 328 to a monitor at a location proximal to elongate body 322 or imaging chip 330 may be adapted to wirelessly transmit images to a receiving unit external to a patient body. Moreover, guidewire 328 may also be advanced through a working lumen of elongate body 322 if so desired.

Figure 29:
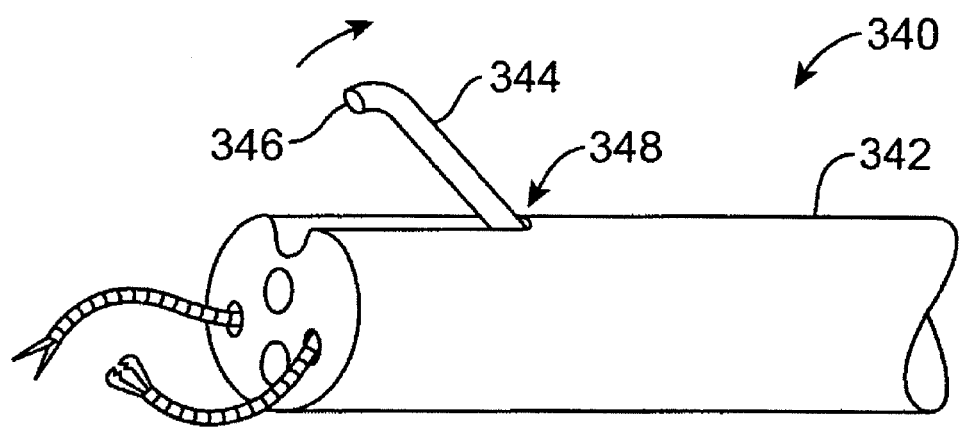
FIG. 29 shows yet another variation in which an imaging chip may be disposed upon a pivoting member.
Figure 30:
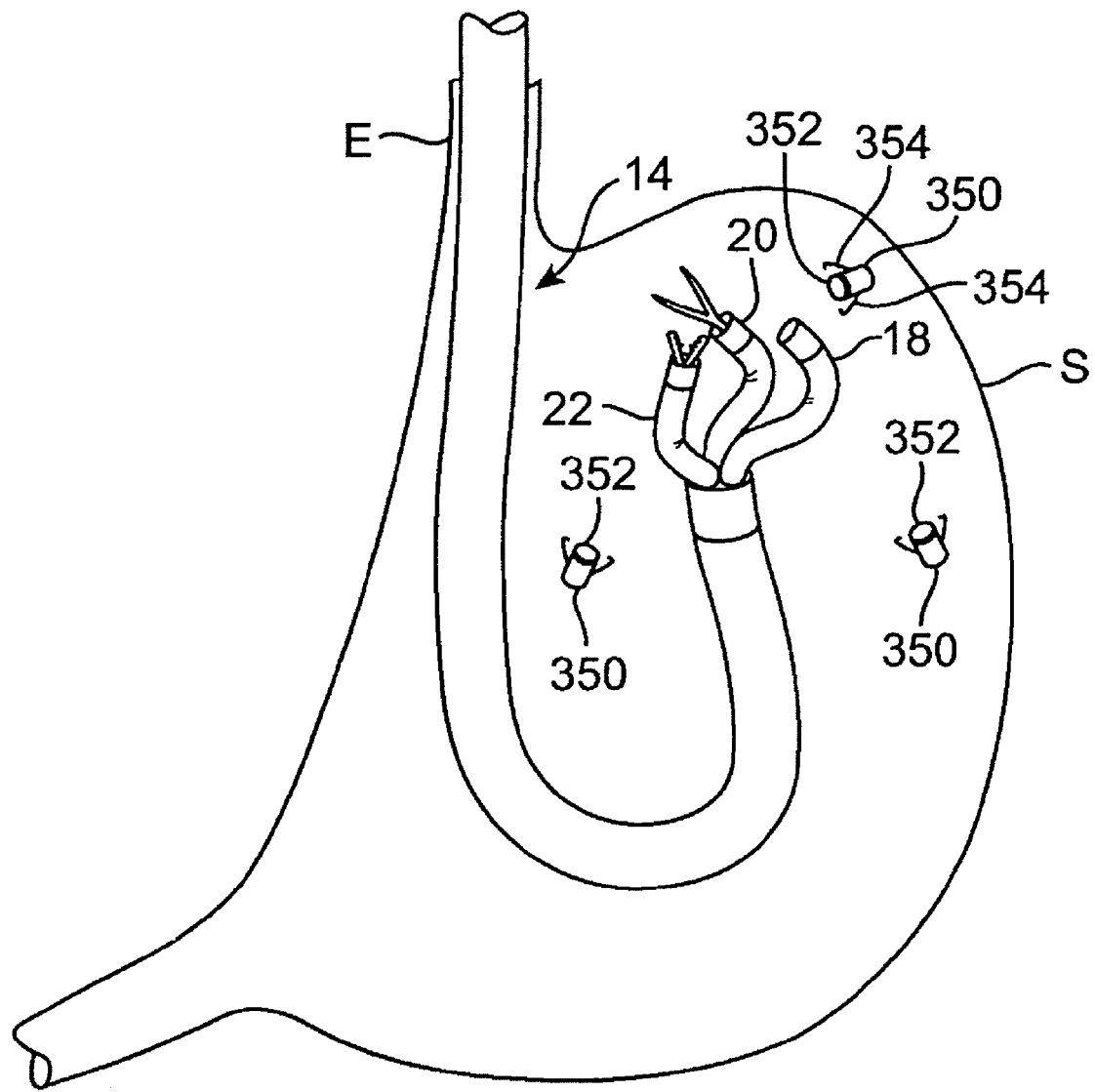
FIG. 30 shows another variation where imaging and/or lighting during a procedure may be provided via imaging capsules and/or LEDs temporarily attached within the patient body and which transmit their images wirelessly to a receiver outside the patient body.

In another alternative, end effector assembly 340 shown in FIG. 29 may comprise an optionally shape-lockable body 342 having visualization member 344 pivotably mounted near or at a distal end of body 342 via pivot 348. Visualization member 344 may have an imager 346, e.g., an imaging chip such as a CCD chip, positioned upon a distal end of member 344, which may be configured to articulate about pivot 348 such that imager 346 is provided an off-axis view of the region distal of elongate body 342.

In another variation, the off-axis visualization may be provided, e.g., within the stomach S, via one or more capsules 350 having integrated imagers 352 positioned within one or more regions of the stomach S. Rather than, or in combination with, off-axis visualization lumen or platform 18, a number of imaging capsules 350 may be temporarily adhered to the interior stomach wall, e.g., via clips 354 attached to the capsule body. The imaging portions 352 of the capsules 350 may be positioned against the stomach wall such that one or more capsules 350 are pointed towards a tissue region of interest. The endoluminal assembly 10 may then be articulated towards the tissue region of interest with either off-axis visualization platform 18 or one or more capsules 350 providing a number of off-axis views for any number of procedures to be accomplished. Imaging capsules such as the PillCam™ are generally used for capsule endoscopy and may be commercially obtained from companies like Given Imaging Ltd. (Israel).

Figure 31A:
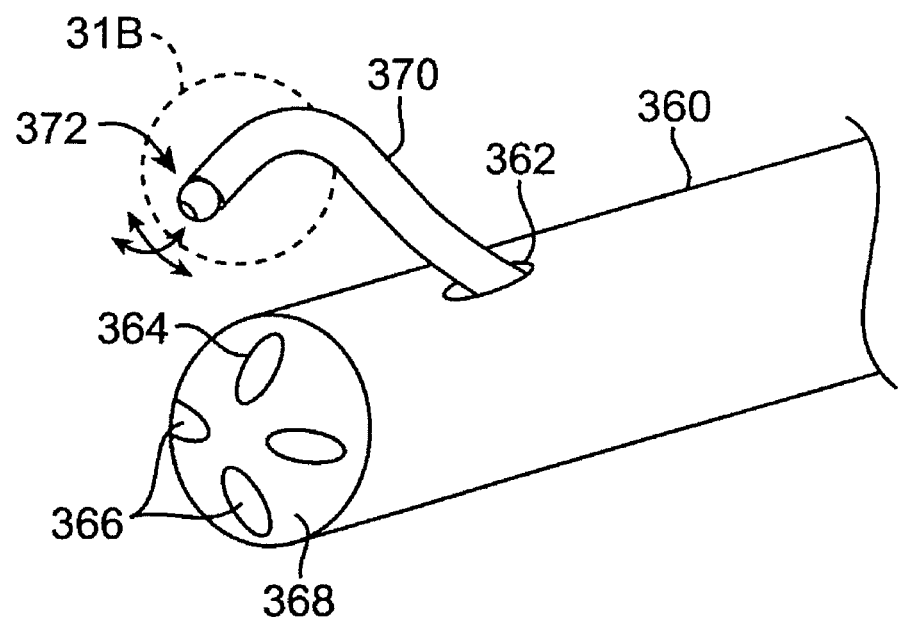
FIG. 31A shows an imaging assembly or endoscope passed through an opening or skive defined along the outer surface of an elongate body.
Figure 31B:
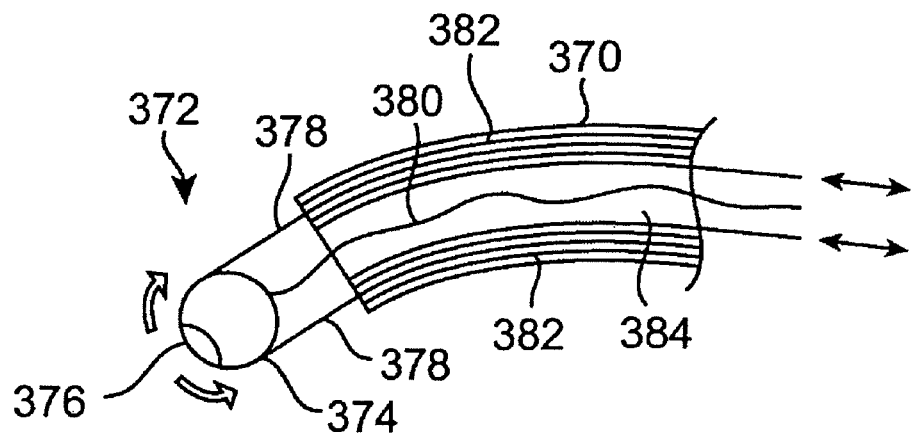
FIG. 31B shows a cross-sectional illustration of the articulatable imaging assembly having a rotatable housing contain an imager.

Turning now to FIGS. 31A and 31B, imaging assembly or endoscope 370 may be advanced through visualization lumen 364, which runs through optionally rigidizable elongate body 360, and passed through opening or skive 362 defined along the outer surface near the distal end of elongate body 360. Imaging assembly 370 may be alternatively passed distally through visualization lumen 364 to the opening defined through the atraumatic distal end 368. When positioned through skive 362, imaging assembly 370 may be articulated into an off-axis configuration relative to the longitudinal axis of elongate body 360 such that the imaging element at its distal end is directed to the area distal to the elongate body 360 along its longitudinal axis, as described above. Such a general configuration may allow for the viewing of various instruments passed through any of the instrument lumens 366 defined through elongate body 360.

In this example, imaging assembly 370 may have an articulatable imaging element 372 positioned at its distal end, which may be rotated in any number of directions. FIG. 31B shows a cross-sectional illustration of the articulatable imaging element 372 partially removed from imaging assembly 370. Imaging element 372 may generally have a rotatable housing 374 containing the imager 376, e.g., CCD or CMOS chip, connected via at least one electrical wire 380 routed through an imaging assembly lumen 384 defined through assembly 370 to a proximal end of the device. The electrical wire 380 may be connected to a processor to allow viewing of images from outside the patient body. The rotatable housing 374 may be rotated in any number of directions, as indicated by the arrows, by alternately tensioning any number of control wires 378 which may be routed through control wire lumens 382 defined through imaging assembly 370. The distal end of imaging assembly 370 may be configured to rotatingly receive and hold rotatable housing 374 in a secure manner while the housing 374 is articulated.

Although imaging assembly 370 may be articulated to direct its distal end to a desired tissue region for optimal imaging, the addition of an optional rotatable imaging element 372 may further facilitate the imaging of various tissue regions without having to reposition the entire assembly.

Figure 32A:
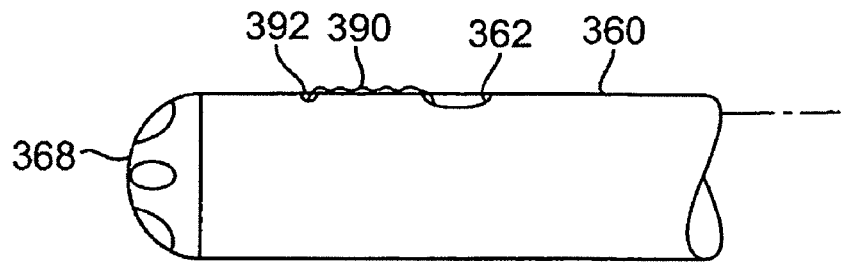
FIGS. 32A to 32C show an instrument utilizing a pull-wire to control the off-axis articulation of the imaging assembly.
Figure 32B:
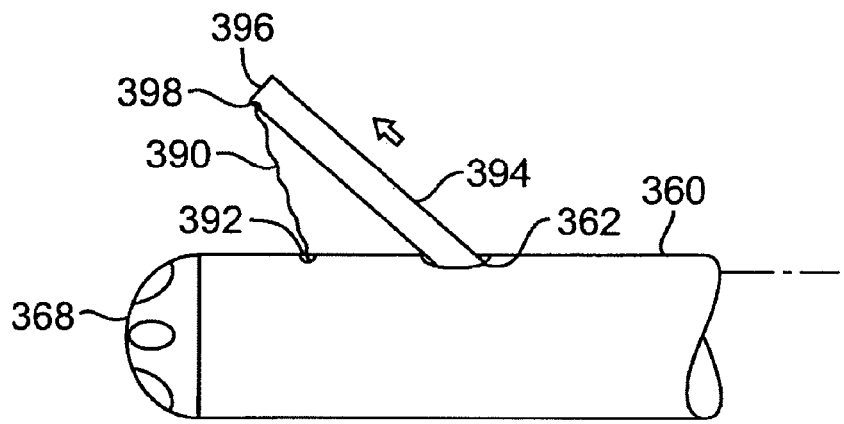
Figure 32C:
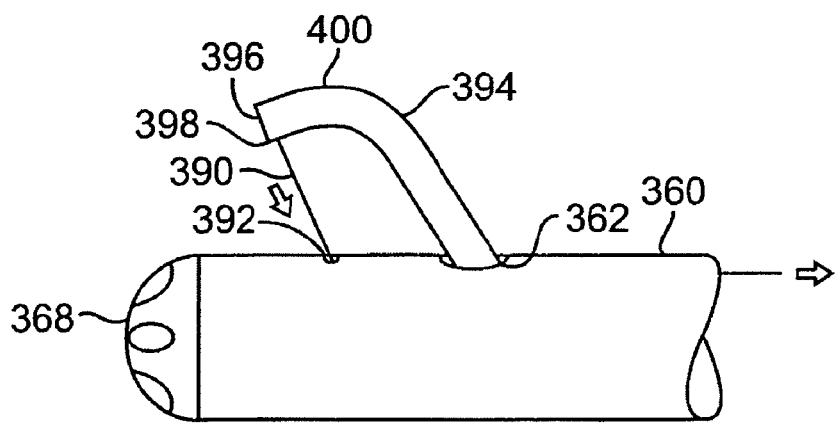

In yet another variation for off-axis imaging, FIGS. 32A to 32C show an instrument where the optionally rigidizable elongate body 360 may use a pull-wire 390 to control the off-axis articulation of the imaging assembly. As shown in FIG. 32A, pull-wire 390 may be routed through skive 362 and through a pull-wire opening 392 located distal of skive 362. Pull-wire 390 may be routed through pull-wire opening 392 proximally through the length of elongate body 360 where the pull-wire 390 may be controlled. The distal end of pull-wire 390 may be attached to a distal end of the imaging assembly 394 at attachment point 398 and as imaging assembly or endoscope 394 is advanced through skive 362, as shown in FIG. 32B, the pull-wire 390 may be tensioned from its proximal end outside the patient body. As shown in FIG. 32C, urging or pulling pull-wire 390 may redirect or bend a distal portion 400 of the imaging assembly 394 with the imager 396 such that the imager 396 is pointed to the region distal to the elongate body 360.

Figure 33A:
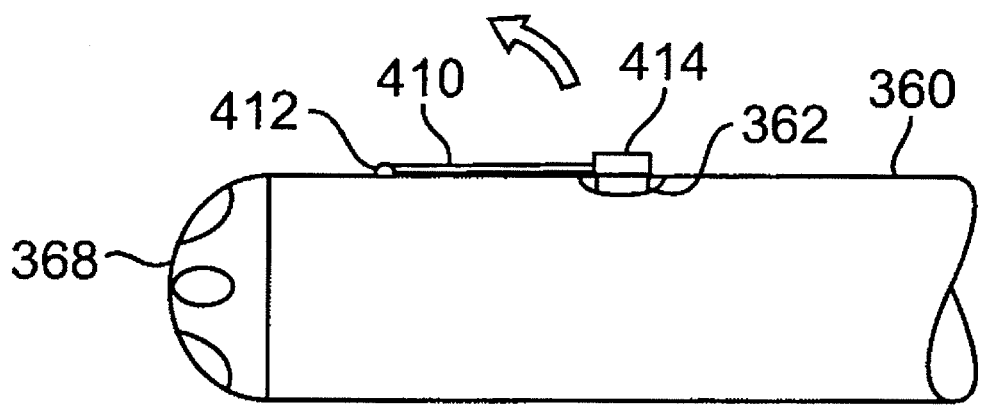
FIGS. 33A and 33B show an elongate body having a swing arm rotatably connected via a pivot to direct the positioning of the imaging assembly in an off-axis configuration.
Figure 33B:
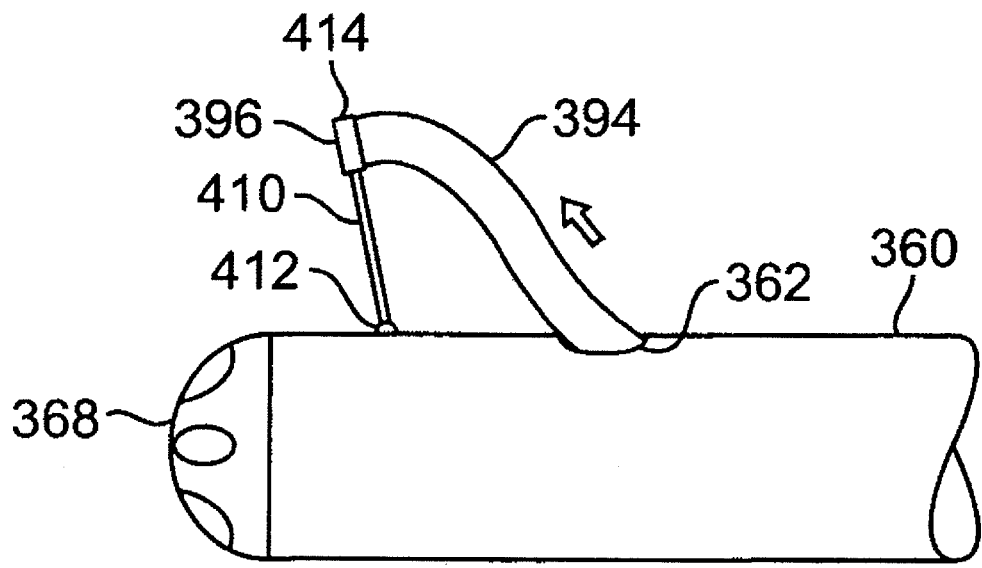

Another variation is illustrated in FIG. 33A which shows elongate body 360 having a swing arm or member 410 rotatably connected via pivot 412 to the elongate body 360 at a location distal to skive 362. A distal end of swing arm 410 may be attached to endoscope 394 via an attachment mechanism 414, e.g., collar, pinned connection, adhesive, etc., such that when endoscope 394 is urged distally through elongate body 360 and out of skive 362, the distal end of endoscope 394 is constrained to follow an arc by the swing arm 410 as the distal end of endoscope 394 pivots about pivot 412, as shown in FIG. 33B. The length of swing arm 410 may be varied depending upon the desired height and positioning of imager 396 in its off-axis configuration.

Moreover, swing arm 410 may be configured as a simple length or it may be configured into any number of structures provided that it is able to pivot relative to elongate body 360 and position imager 396 into its off-axis position. Additionally, a mechanical stop may be positioned adjacent to pivot 412 to prevent over-arcing of swing arm 410; alternatively, the imaging assembly or endoscope 394 may be limited from being advanced distally out of skive 362 beyond a pre-determined point to prevent over-arcing of the imager 396.

Figure 34A:
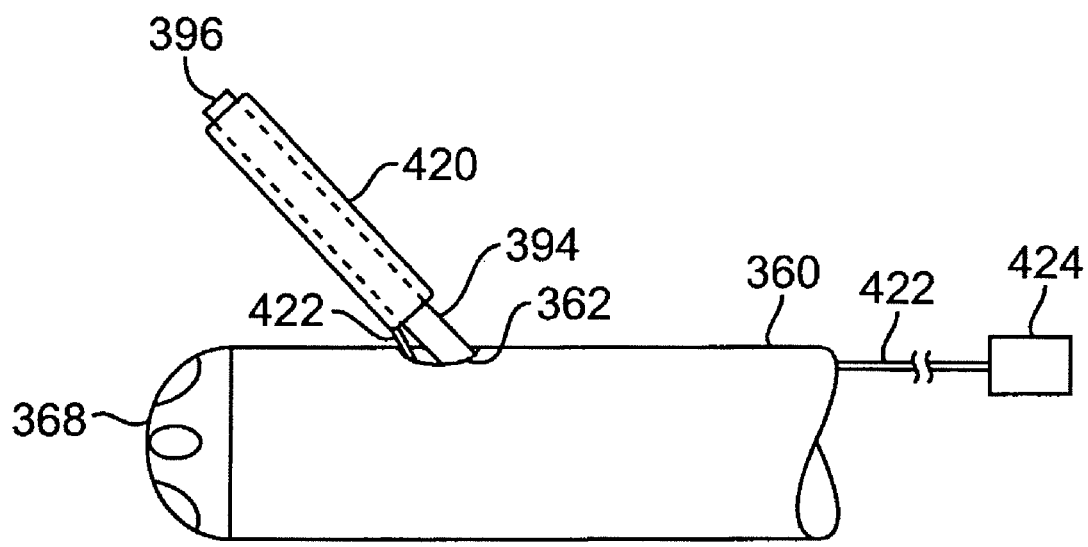
FIGS. 34A and 34B show a balloon assembly which may be configured to conform into a bent or curved configuration for positioning of the imaging assembly in an off-axis configuration.
Figure 34B:
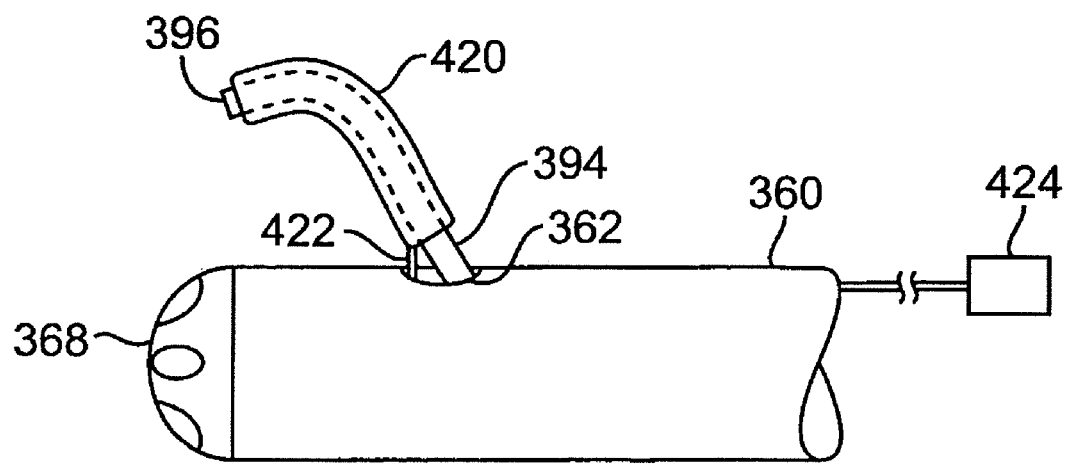

In yet another variation, a balloon 420 which is flexible in its deflated state may be positioned in close contact against a distal portion of the imaging assembly or endoscope 394. Balloon 420 may be in fluid communication through inflation lumen 422 through a length of elongate body 360 to an inflation pump 424 located outside the patient body, as shown in FIG. 34A. The balloon 420 may be configured such that when inflated with a fluid or gas, the inflated balloon 420 conforms to a bent configuration which may be predetermined. The balloon 420 may, for instance, be inflated only along a single side such that filling the balloon 420 results in an asymmetric shape. When the endoscope 394 with balloon 420 is advanced out of skive 362, the balloon 420 may be inflated via a fluid (such as saline, water, etc.) or gas (such as air, nitrogen, carbon dioxide, etc.) such that the balloon 420 conforms to its bent configuration and also urges the wrapped endoscope 394 to conform into a bent or curved off-axis configuration, as shown in FIG. 34B.

Alternatively, rather than utilizing an inflation balloon 420, a scaffold or tubular covering having a scaffold 420' embedded therein which is made from a super-elastic or shape-memory material may be conformed or wrapped around the distal portion of endoscope 394. Such a scaffold may be made from a super-elastic or shape-memory alloy such as Nitinol. If a super-elastic scaffold is used, the endoscope 394 may be automatically urged into a bent or curved configuration when advanced out of skive 362. Alternatively, a shape-memory alloy scaffold may be electrically connected via one or more wires 422' to a power supply 424', which may be activated to actuate the scaffold 420' into a bent or curved configuration.

Figure 35A:
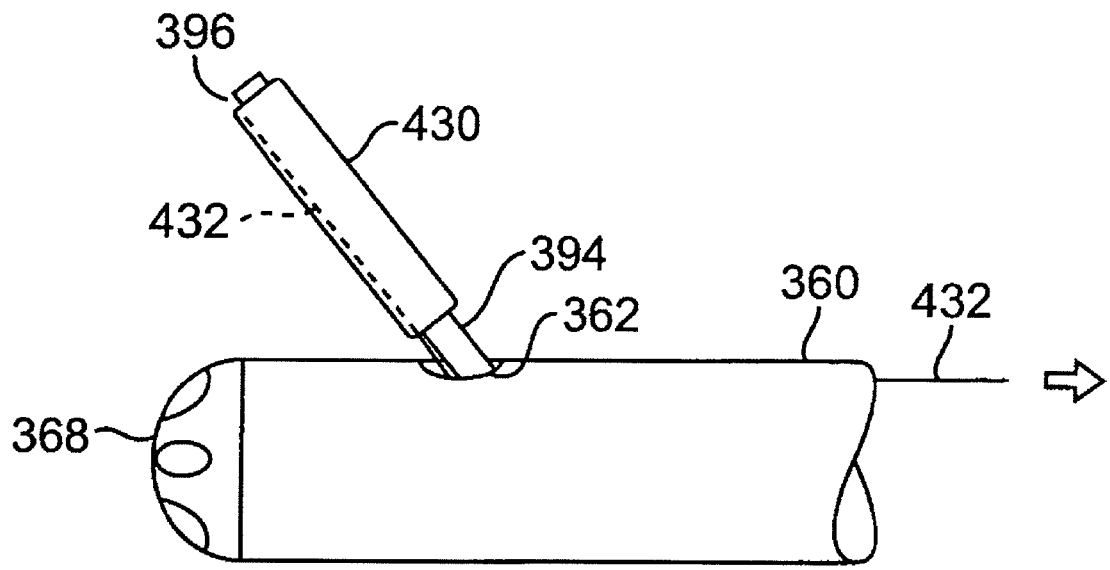
FIGS. 35A and 35B show a sleeve having a pre-formed bend or curve shape which may be wrapped or at least partially surrounded around an endoscope to position the imaging assembly in an off-axis configuration.
Figure 35B:
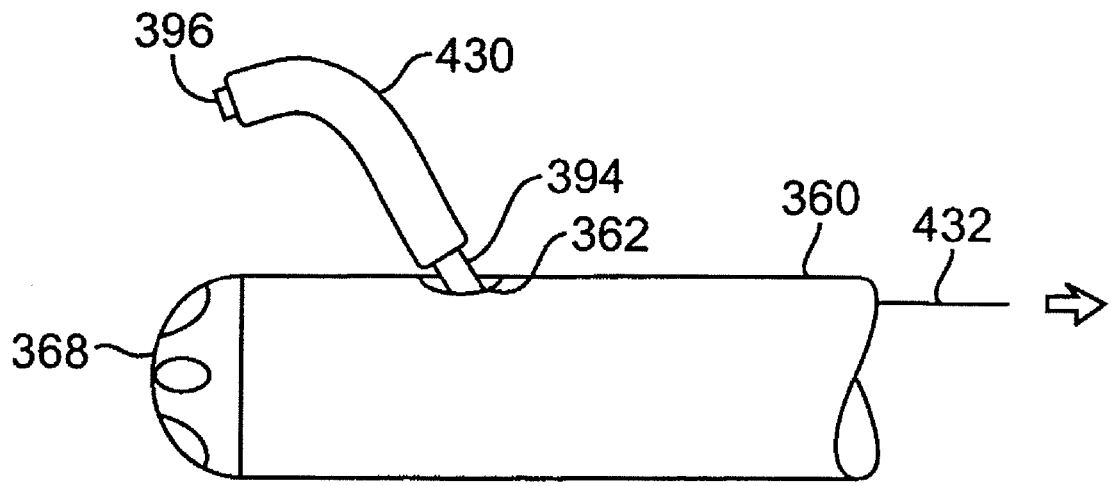

Yet another variation is shown in FIG. 35A in which endoscope 394 may be wrapped or at least partially surrounded by a sleeve 430 having a pre-formed bent or curved configuration. Sleeve 430 may be composed of a super-elastic or shape-memory material scaffold or covering, as described above, which is biased to form the bent or curved configuration when unconstrained. To maintain a straightened configuration when advanced through elongate body 360 and out of skive 362, a straightening wire or mandrel 432, made for example from stainless steel, Nitinol, a polymeric material, etc., may be disposed within sleeve 430. When sleeve 430 has been desirably positioned through skive 362, wire or mandrel 432 may be pulled or tensioned from its proximal end until it is withdrawn from sleeve 430, thereby allowing sleeve 430 to reconfigure itself into its relaxed configuration and to redirect imager 396 into its off-axis configuration, as shown in FIG. 35B. To withdraw sleeve 430 and endoscope 394 from the patient body, endoscope 394 may be simply pulled proximally through skive 362 while straightening sleeve 430 and back into elongate body 360.

Figure 36A:
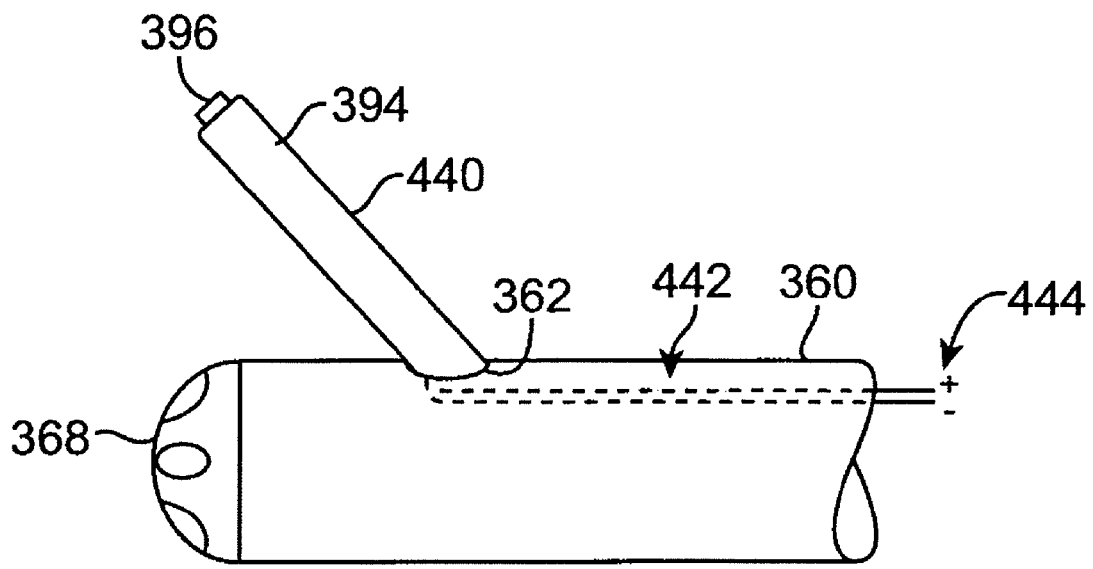
FIGS. 36A and 36B show a sleeve made from an electro-active polymer which may be actuated to reconfigure a position of the imaging assembly.
Figure 36B:
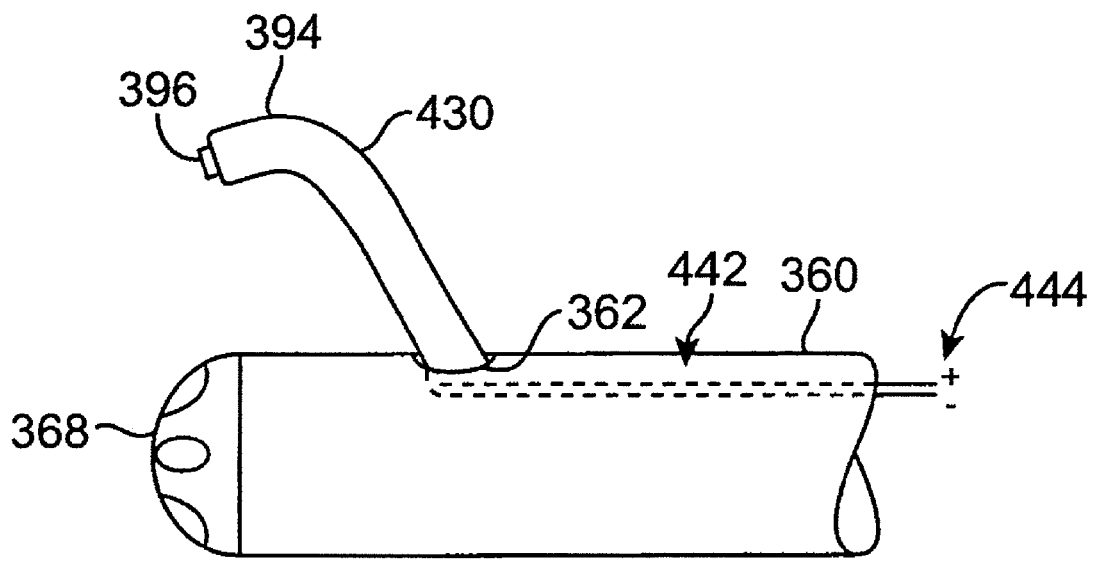

Another variation may utilize a sleeve 440 made from an electro-active polymer (EAP) material such as polymer-metal composites, conductive polymers, ferro-electric polymers, etc., as shown in FIG. 36A. EAP sleeve 440 may be wrapped completely or at least partially about endoscope 394 such that sleeve 440 remains flexibly compliant when passed through elongate body 360 and skive 362. EAP sleeve 440 may be electrically connected via electrical connection 442 to a power supply 444 located external to the patient body such that when power supply 444 is activated, EAP sleeve 440 may be stimulated to reconfigure itself into a bent or curved off-axis configuration, as seen in FIG. 36B, such that imager 396 is directed distal to the elongate body 360. Shutting power supply 444 off may allow EAP sleeve 440 to lose its curved configuration and transition back into its flexible state for withdrawal through skive 362 and from the patient body.

Figure 37A:
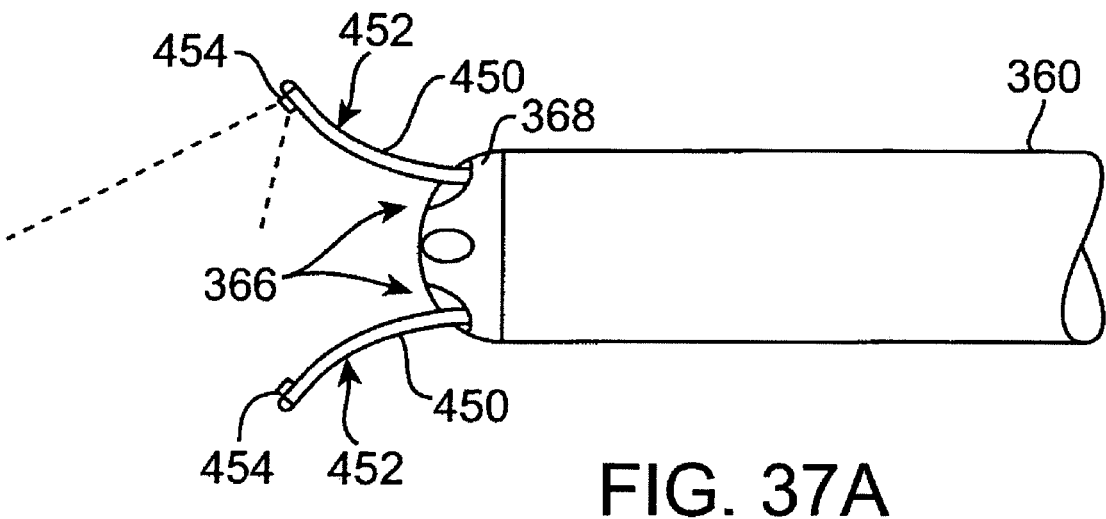
FIGS. 37A and 37B show side and end views, respectively, of a variation utilizing two or more off-axis visualization elements which are reconfigurable between a straightened and curved configuration.

Another variation for off-axis visualization may utilize multiple, e.g., two or more, off-axis visualization elements. Illustrated in the side view of FIG. 37A, two or more imaging assemblies 450 which are reconfigurable between a straightened and curved configuration may be each advanced through a corresponding lumen 366 defined through elongate body 360. Each imaging assembly 450 may be configured such that an imaging element 454, such as an optical fiber, CCD or CMOS chip, etc., may be mounted near or at the distal end of a curved or bendable section 452 such that when the curved section 452 is advanced from elongate body 360, the imaging element 454 is directed into an off-axis position relative to the longitudinal axis defined by the elongate body 360.

Figure 37B:
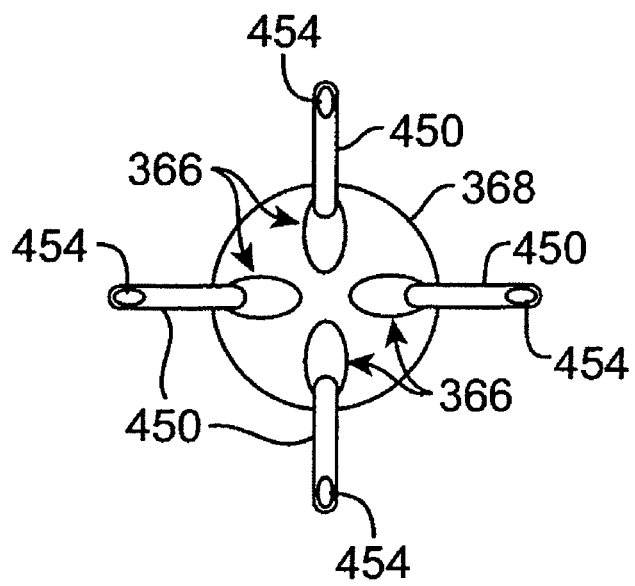

In one example, two imaging assemblies 450 may be advanced through their respective adjacent lumens 366 and rotated within their lumens 366 to align the respective imagers 454 to a common tissue region. In another example, four imaging assemblies 450 may be advanced through respective lumens 366, as shown in the end view of FIG. 37B, and advanced out of elongate body 360 such that each imaging assembly 450 is radially configured in an off-axis position with respect to the longitudinal axis of elongate body 360. Moreover, each imaging assembly 450 may be uniformly or arbitrarily positioned with respect to one another in its deployed configuration.

Figure 38A:
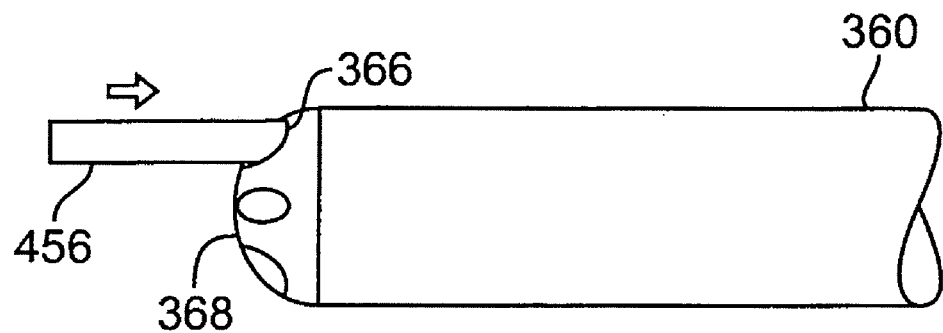
FIGS. 38A and 38B show another variation where two or more off-axis visualization elements may be constrained within a retractable retaining sleeve.
Figure 38B:
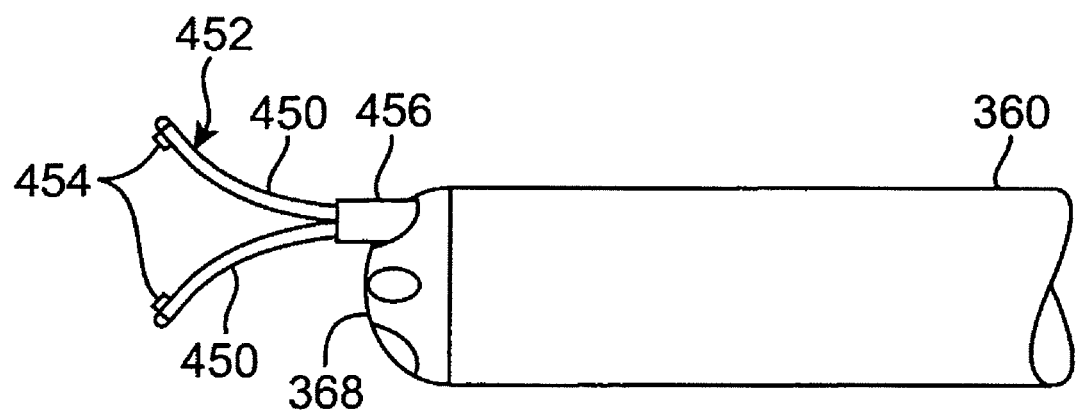

In a similar variation, one or more imaging assemblies 450 may be advanced through one or more lumens 366 while contained within a tubular retaining sleeve 456 which is retractable with respect to the imaging assembly 450, as shown in FIG. 38A. Retaining sleeve 456 may be advanced through lumen 366 from atraumatic distal end 368 prior to or simultaneously with imaging assemblies 450 and retaining sleeve 456 may be retracted relative to imaging assemblies 450 leaving the one or more assemblies 450 to reconfigure into its curved configuration, as shown in FIG. 38B.

Figure 39A:
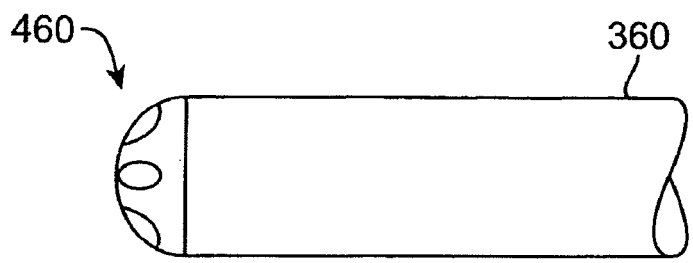
Figure 39B:
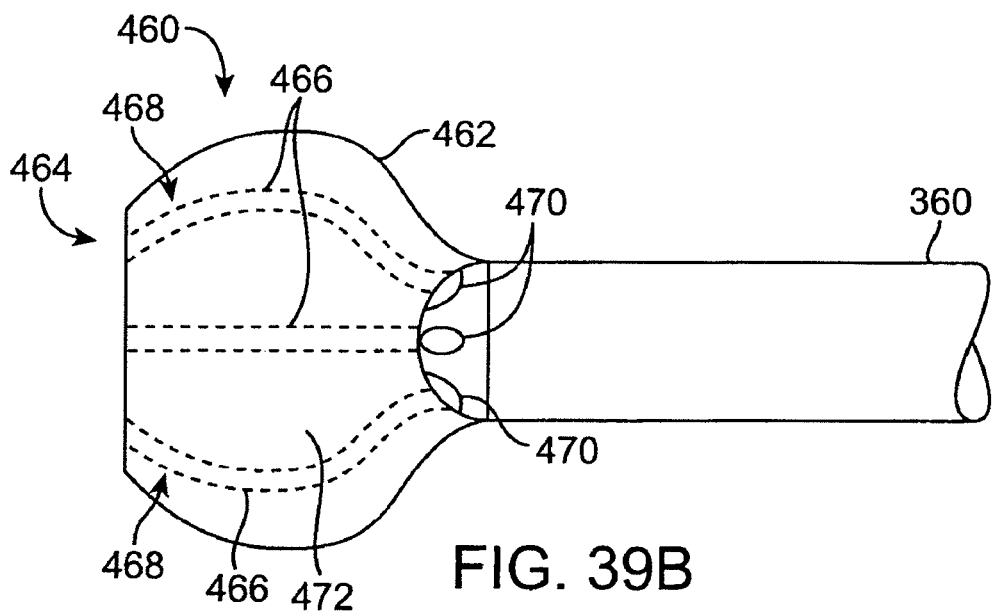
Figure 39C:
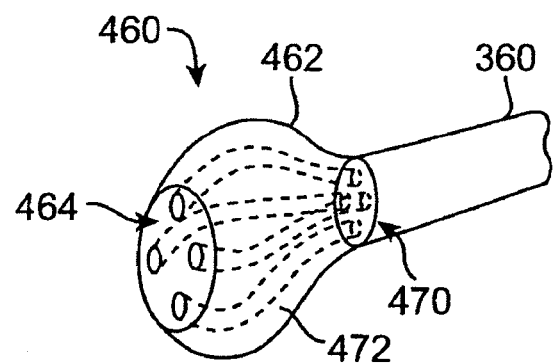
FIG. 39C shows a perspective view of the assembly of FIG. 39B with the balloon in its inflated configuration.

Another variation utilizing an inflatable balloon assembly 460 which defines one or more curved lumens therethrough may be utilized. As shown in FIG. 39A, an un-inflated balloon assembly 460 may lie in its collapsed shape in a low profile against elongate body 360. When the interior 472 of balloon 462 is inflated or expanded with a gas (such as nitrogen, carbon dioxide, air, etc.) or liquid (such as saline, water, etc.), balloon 462 which may be made from a distensible or expandable material may expand, as shown in FIG. 39B. In its expanded configuration, balloon 462 may define or more unobstructed lumens 466 extending through the balloon 462 from a working lumen opening 470 in elongate body 360 and terminating in a corresponding lumen opening 464 defined along a side or at the terminal end of the balloon 462, as shown in FIG. 39C.

Lumens 466 may curve radially outward within balloon 462 with respect to the longitudinal axis of elongate body 360 and then curve radially back inwards 468 with respect to the longitudinal axis. This curvature may be such that any tools or endoscopic instruments passed through lumen 466 are directed towards the longitudinal axis of elongate body 360 and to a tissue region of interest for any number of procedures to be performed.

Figure 40A:
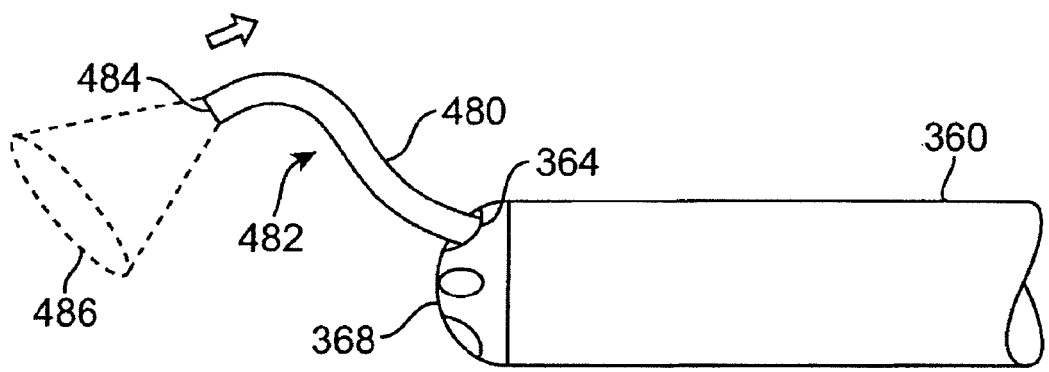
FIGS. 40A and 40B show an endoscope or imaging assembly which may be articulated from a first off-axis position to a second off-axis position to result in an expanded field-of-view.

In many endoscopic procedures, visualization of a tissue region of interest often requires repositioning of the imaging assembly or endoscope and re-visualizing the tissue region. Repositioning typically involves pulling or directing the endoscope away from the tissue region and then re-visualizing the tissue region from another position or from a more proximal location. One example for endoscopically simulating the repositioning and re-visualizing of a tissue region may be seen in FIGS. 40A and 40B. As illustrated in FIG. 40A, endoscope or imaging assembly 480 may be advanced through elongate body 360 and out of lumen 364, where imager 484 may be articulated into a first off-axis position relative to a longitudinal axis of elongate body 360, as described previously. In its first off-axis configuration, a target area distal to elongate body 360 may be visualized within a first field-of-view 486.

Figure 40B:
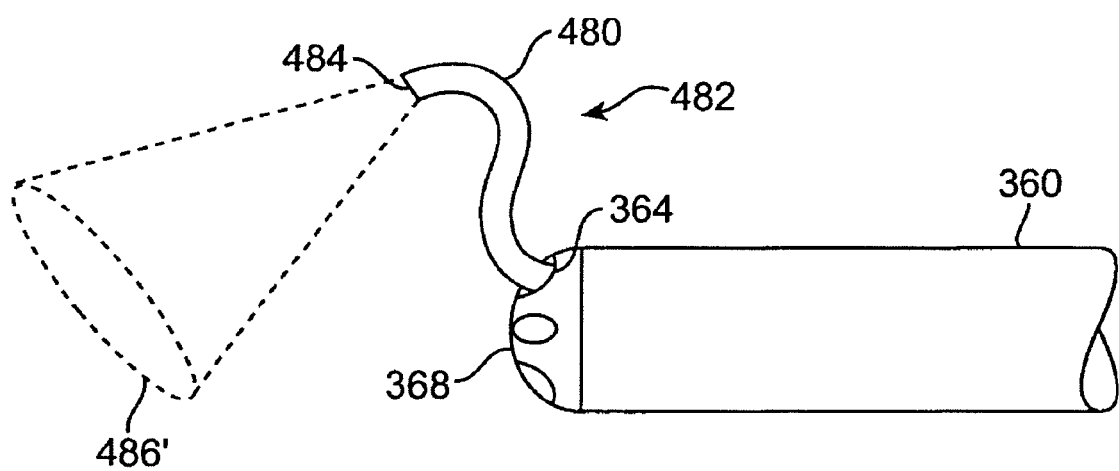

If a larger visual perspective is desired, an articulatable section 482 of endoscope 480 may be further urged or articulated from its proximal end outside the patient body into a second off-axis configuration, as shown in FIG. 40B, which is more proximal than the first off-axis configuration. The resulting expanded field-of-view 486' may thus provide for a larger visual perspective of the target area being visualized without having to reposition a length or the entire length of elongate body 360 relative to the visualized target area.

Figure 41A:
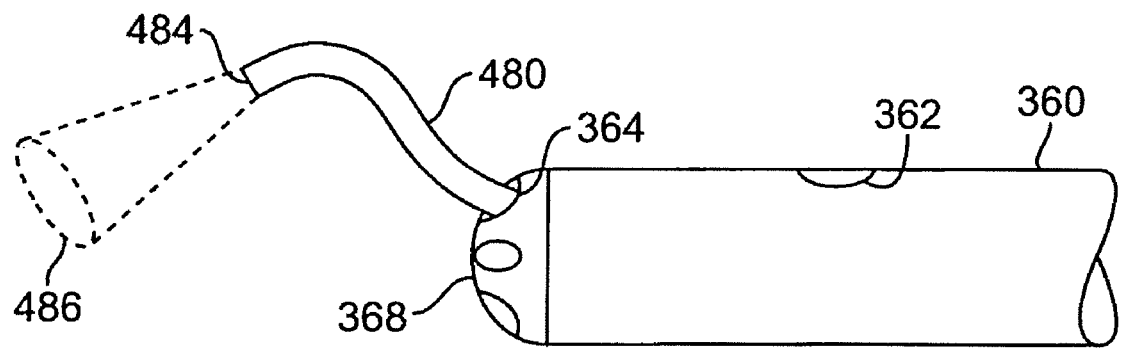
FIGS. 41A and 41B show another variation for articulating an endoscope or imaging assembly from a first off-axis position to a proximal second off-axis position through an opening or skive along the elongate body.
Figure 41B:
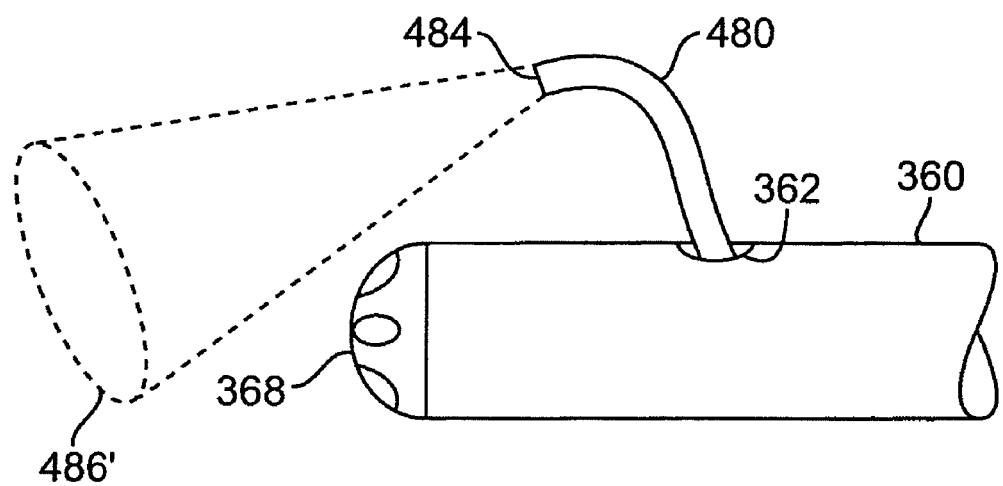

In another alternative, endoscope or imaging assembly 480 may be positioned into its first off-axis configuration, as above, to provide a first field-of-view 486, as shown in FIG. 41A. Endoscope 480 may then be withdrawn at least partially through elongate body 360 and then re-advanced through a skive 362 into a second off-axis configuration such that imager 484 is repositioned proximal of the first off-axis configuration to provide an expanded field-of-view 486', as shown in FIG. 41B. Skive 362, as described herein and also in U.S. patent application Ser. No. 10/797,485 filed Mar. 9, 2004 (U.S. Pat. Pub. No. 2004/0249367A1), which is incorporated herein by reference in its entirety, may be defined at any number of locations along the length of elongate body 360 proximal to the distal tip 368.

Aside from physically repositioning the endoscope or imaging assembly 480, another variation may incorporate an imaging system having a variable field-of-view which may be altered by repositioning the optics within the imager 484. One such example of an alterable field-of-view is shown and described in U.S. Pat. Pub. No. 2005/0267335 A1 filed May 18, 2005 to Okada et al., which is incorporated herein by reference in its entirety. Such a device may be optionally incorporated into any of the imaging assemblies described herein as practicable.

Figure 42:
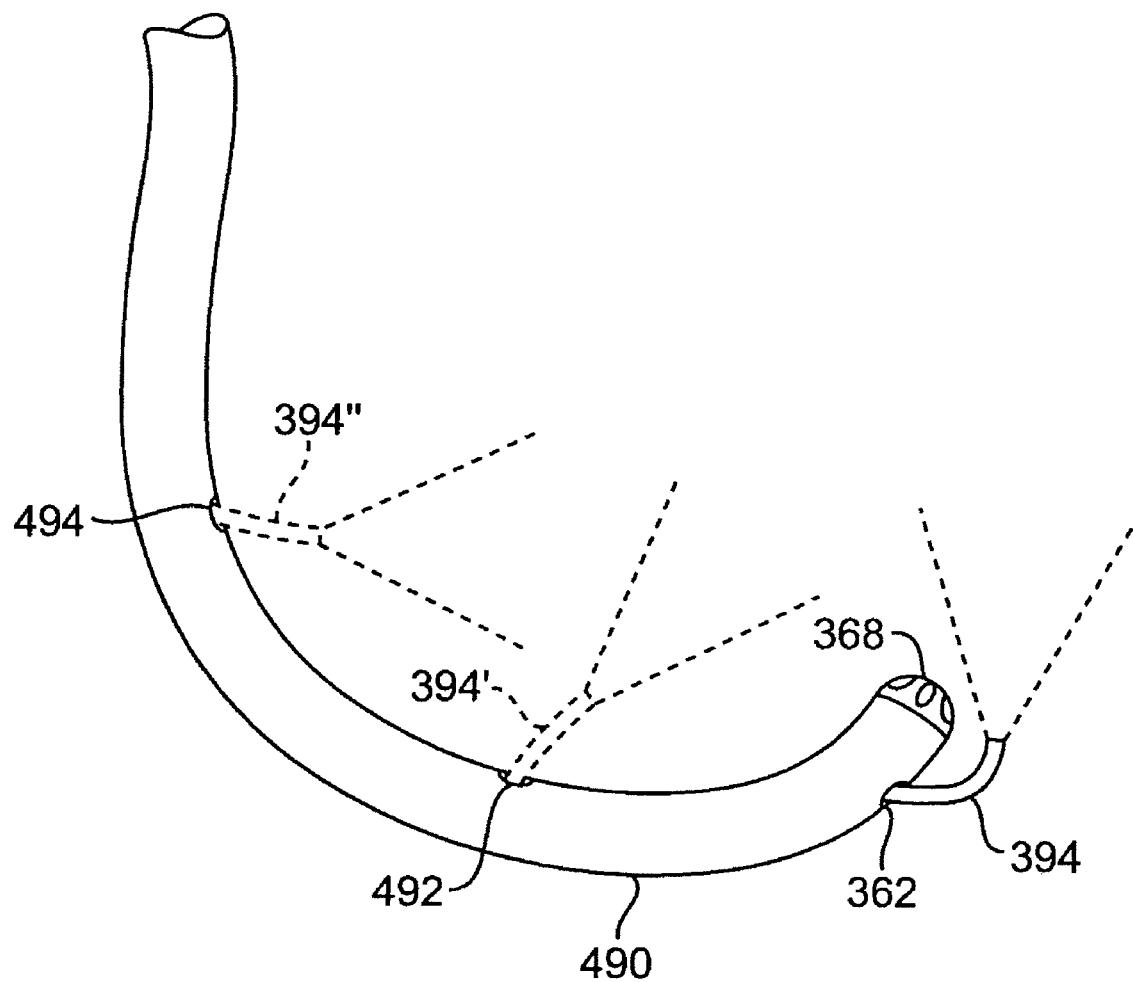
FIG. 42 shows an example of an elongate body which utilizes multiple skives along its length.

In another variation for utilizing one or more skives along the length of elongate body 490, FIG. 42 illustrates an example in which multiple skives may be defined along the body. In this example, endoscope 394 may be positioned into its off-axis configuration through a distally positioned skive 362 to provide a first field-of-view. An additional second skive 492 and a third skive 494 may be positioned proximally along the length 490 such that the endoscope 394 may be positioned in alternate proximal off-axis positions 394', 394" to provide alternate views of the target area being visualized. More than three skives may be utilized along the elongate body 490, as practicable, and the skives may be varied relative to its circumferential position, as desired. For instance, one or more skives may be aligned linearly along the length of elongate body 490 such that the skives are located along the same side of elongate body 490.

Alternatively, the one or more skives may be aligned in alternating or non-uniform patterns. Furthermore, if the one or more skives are located along different sides of the elongate body 490, multiple visualization instruments (or multiple other endoscopic instruments) may be passed simultaneously through elongate body 490 to exit each skive, if so desired.

Figure 43A:
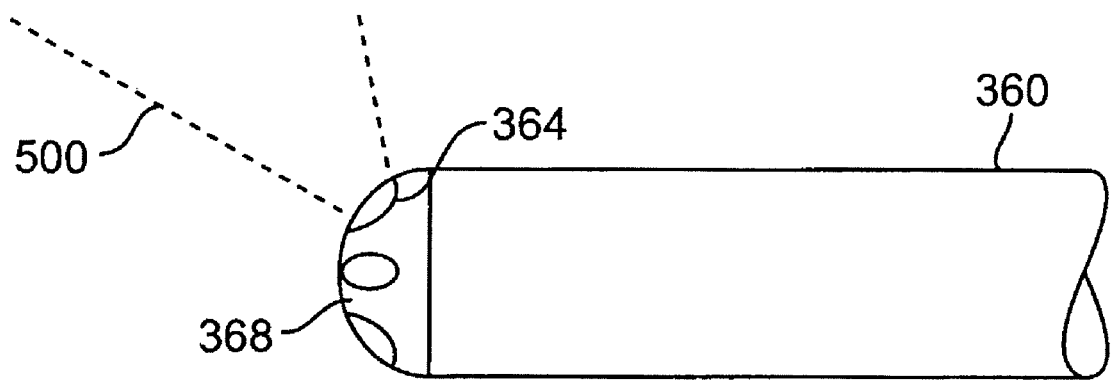
FIGS. 43A and 43B show side and partial cross-sectional side views, respectively, of an in-line imaging assembly for providing off-axis visualization utilizing a rotatable element.
Figure 43B:
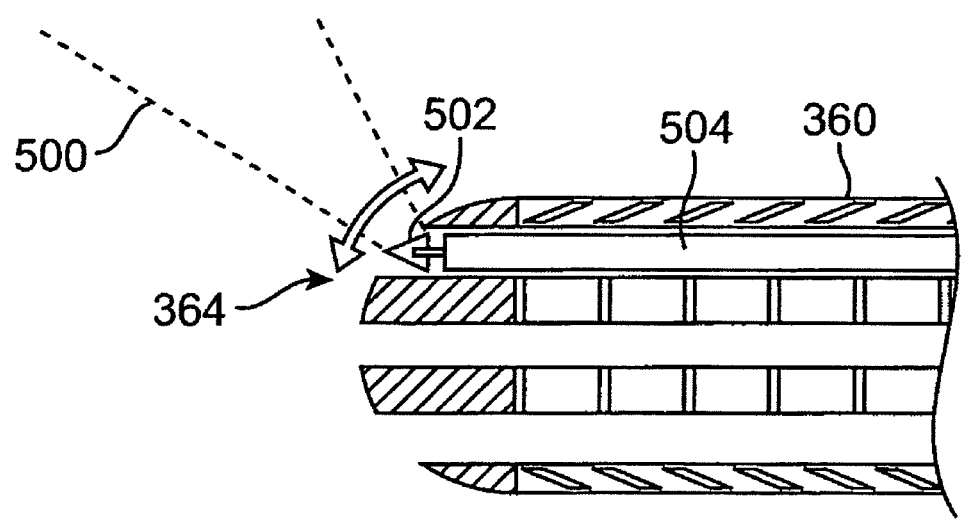

Aside from articulating visualization assemblies into off-axis configurations, off-axis imaging relative to the elongate body may be provided alternatively by utilizing various in-line angled configurations. One example is shown in FIG. 43A which illustrates elongate body 360 with a visualization element positioned near or at the distal end of elongate body 360 to provide an angled field-of-view 500 relative to the longitudinal axis of elongate body 360. FIG. 43B shows a partial cross-sectional view of elongate body 360, which illustrates an imaging assembly 504, e.g., optical fiber bundles, having a rotatable prism assembly 502 positioned distal of the imaging assembly 504. To alter the angle of the imaging field-of-view 500, prism 502 may be rotated relative to the imaging assembly 504 via pull-wires, motors, or any other number of mechanisms. In other variations, an imaging chip, such as a CCD or CMOS chip, may be utilized to rotate in an angled configuration to provide the off-axis imaging.

Figure 44A:
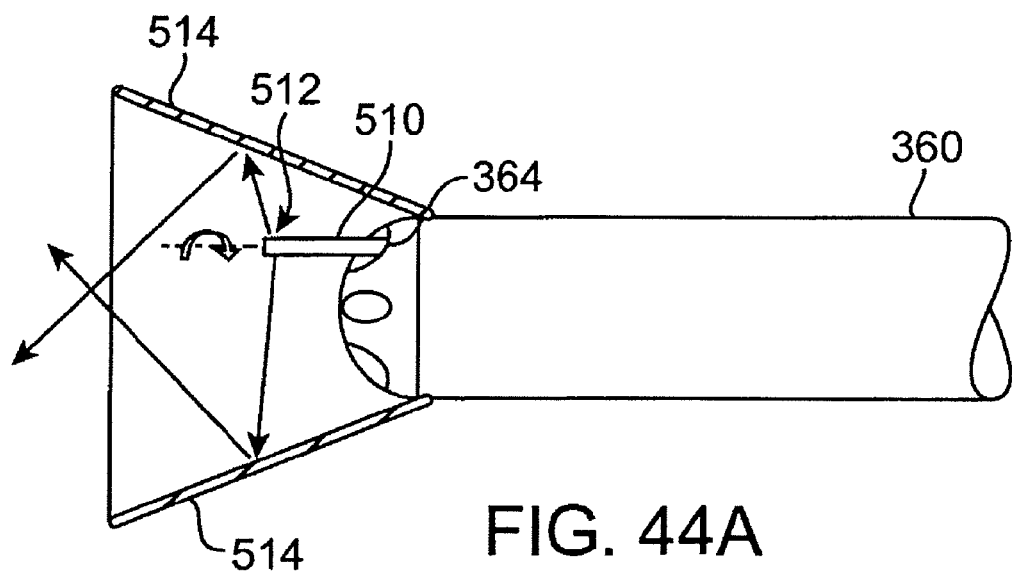
FIGS. 44A and 44B show partial cross-sectional side and end views, respectively, of another variation of an in-line imaging assembly utilizing one or more pivoting reflectors.

Another example for in-line off-axis imaging is provided in FIG. 44A, which shows a partial side view of elongate body 360 having an imaging assembly 510, such as optical fibers or imaging chips, rotatably positioned relative to elongate body 360. An off-axis imaging chip 512 may be positioned near or at the distal end of imaging assembly 510. Mounted, removably or permanently, upon the distal end of elongate body 360 are one or more reflectors 514 which extend distally from and which are pivotally attached to elongate body 360. Off-axis imaging chip 512 may be selectively rotated to view a tissue region by viewing images reflected from the one or more reflectors 514. The reflectors 514 may be made from a number of highly reflective materials, such as polished stainless steels or other metals, reflective glass, etc.

Figure 44B:
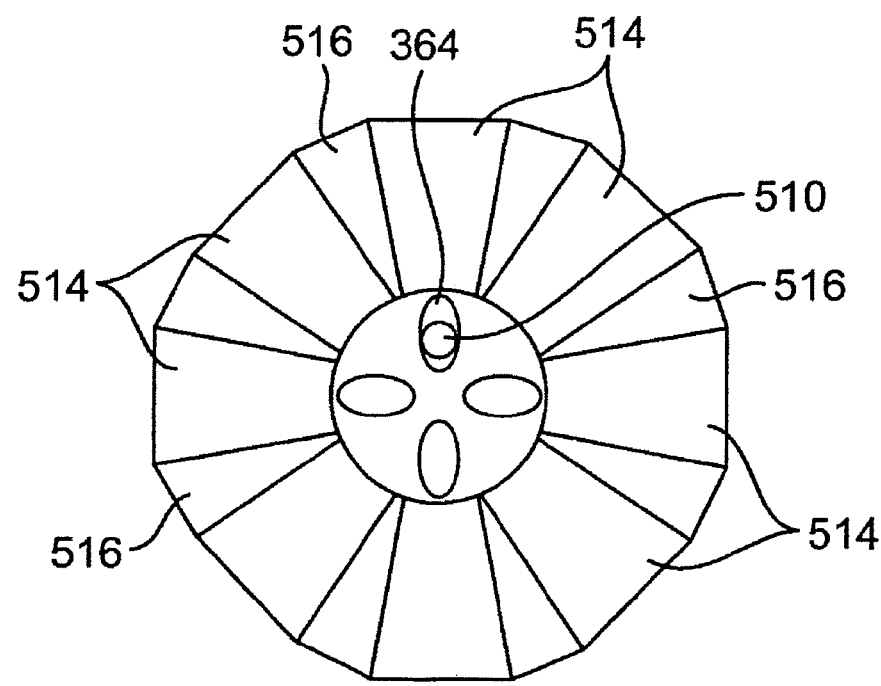

During endoluminal advancement through the patient body, the one or more reflectors 514 may be retracted into a low profile and then pivoted radially into an angled position to provide for imaging. Moreover, the radial expansion of the reflectors 514 may also provide for tissue retraction of any obstructing tissue structures adjacent or proximate to the tissue region being visualized. FIG. 44B shows an end view of the radially expanded reflectors 514. To prevent pinching of tissue between the expanded reflectors 514, an expandable covering 516 made from a distensible material, such as silicone, polyurethane, etc., may be optionally provided between the reflectors 514 or around the entire imaging assembly.

In addition to providing for the off-axis visualization, whether in-line or off-axis relative to the longitudinal axis of the elongate body, additional visualization enhancements may be optionally provided in any of the variations described herein. One example of such a visualization enhancement is shown in FIG. 45A, which illustrates an end view of elongate body 360 with an imaging assembly 520 translatably positioned within lumen 364. Imaging assembly 520 may provide multiple adjacent imaging chips 522, e.g., CCD or CMOS chips, positioned at the distal end of assembly 520.

FIGS. 45B to 45D show a detail view of the imaging chips 522 and illustrate an example for their use. In this example, first chip 524, second chip 526, and third chip 528 may be uniformly and linearly aligned relative to one another. To provide the visualization, first chip 524 may be activated at a time $t=t_0$ to provide a first field-of-view 524', as shown in FIG. 45B. The image provided in the first-field of view 524' may be captured and stored via a computer (not shown). Second chip 526 may be activated subsequently at a time $t=t_0+dt_1$ to provide a second field-of-view 526' upon first chip 524 being de-activated, as shown in FIG. 45C. The image provided in the second field-of-view 526' may comprise an image of the region visualized which is slightly adjacent to the image captured in the first field-of-view 524'. Second field-of-view 526' may likewise be captured and stored via the computer. Third chip 528 may then be activated subsequently at a time t=$t_0$+$dt_2$ to provide a third field-of-view 528' upon second chip 526 being de-activated, as shown in FIG. 45D. The image provided by the third field-of-view 528' may likewise comprise an image of the region which is slightly adjacent to the image captured in the second field-of-view 526'. Third field-of-view 528' may also be captured and stored in the computer.

Once all three images have been sequentially captured, the stored images may be processed via the computer or processor to result in a simulated singular panoramic composite image 530 of the tissue region, as shown in FIG. 45E. The sequential imaging, capturing, and displaying may be continuously performed during a procedure to provide enhanced imaging to the practitioner.

Figure 46:
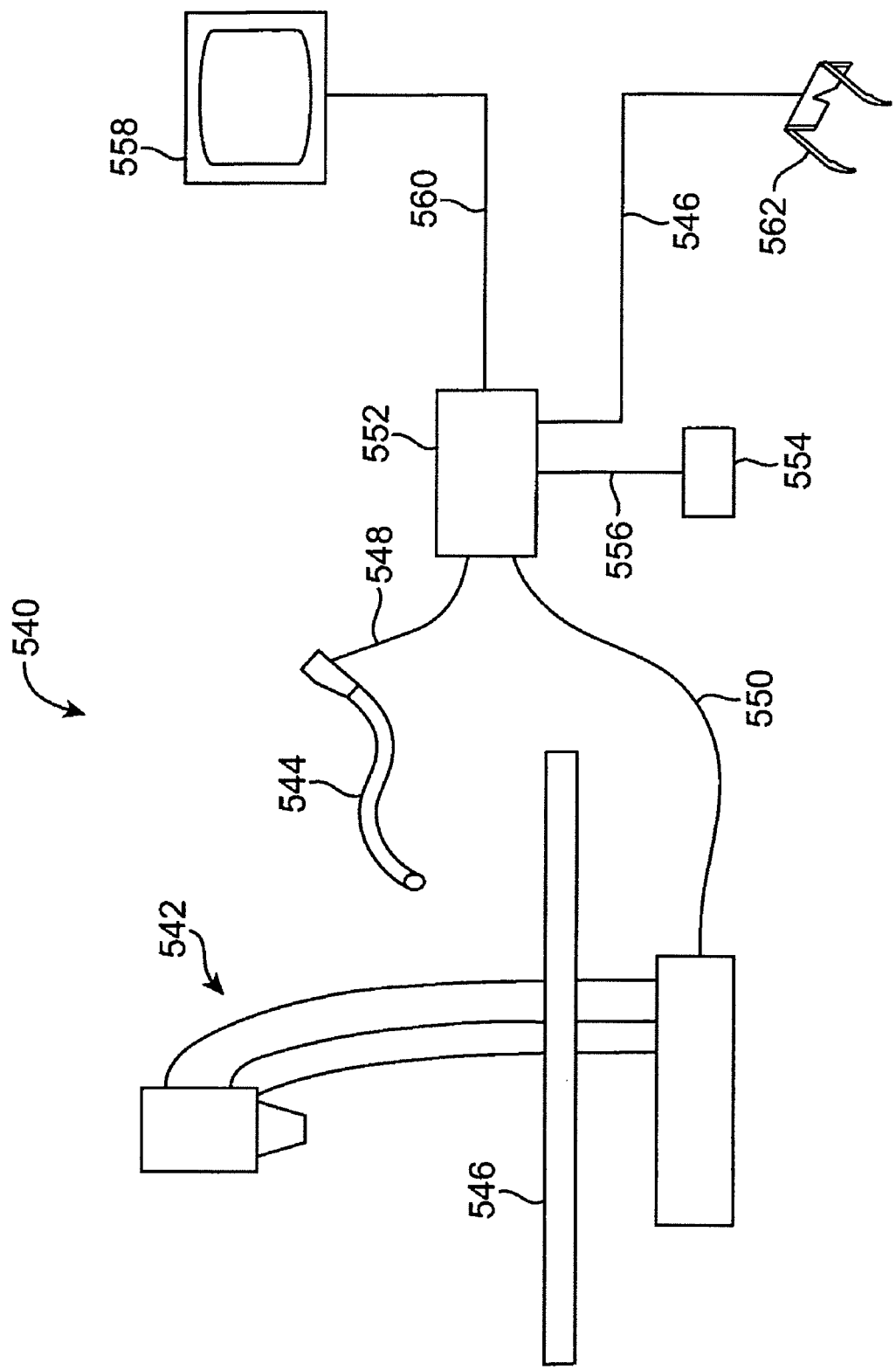
FIG. 46 illustrates another example for image enhancement utilizing a combined fluoroscopic-endoscopic imaging system for display on a monitor and/or goggles.

Another example for providing enhanced imaging in any of the variations described herein is shown in FIG. 46. In this example, imaging provided by any of the endoluminal instruments described herein may be combined into a fluoroscopic-endoscopic imaging system 540 where images provided by a fluoroscope 542, which is typically used to provide fluoroscopic images via extra-corporeal imaging, may be combined with images provided by any of the endoluminal instruments 544 described herein (or even with conventional endoscopes), which provide images obtained via endoluminal intra-corporeal imaging.

A patient may be positioned upon a platform 546 for fluoroscopic imaging. The fluoroscopic images may be transmitted via electrical connection 550 to a processor 552. The endoluminal instrument 544 may be likewise connected via electrical connection 548 to processor 552 to provide endoluminal images. Processor 552 may be configured to process both the fluoroscopic and endoluminal images or separate processors may be utilized to individually process each respective images which may then be combined via a third processor (not shown) in communication with each separate processor.

In either case, the fluoroscopic and endoluminal images may then be transmitted and displayed via electrical connection 560 on a monitor 558 and/or optionally via electrical connection 564 through goggles or glasses 562, which may be worn by the practitioner during the procedure. A switch 554 (e.g., toggle, foot switch, etc.) connected to processor 552 via electrical connection 556 may be actuated by the practitioner, nurse, or technician to selectively switch the image displayed on the monitor 558 and/or goggles 562 between the fluoroscopic image and the endoluminal image. Alternatively, the fluoroscopic image and/or the endoluminal image may be displayed simultaneously on the monitor 558 and/or goggles 562 in a split-screen or picture-in-picture manner to allow the practitioner to view both the fluoroscopic and endoluminal images simultaneously without having to toggle between the two. Such a system 540 may facilitate efficient visualization and may also reduce the amount of equipment in the operating room and/or endoscopy suite during a procedure.

Although various illustrative embodiments are described above, it will be evident to one skilled in the art that a variety of combinations of aspects of different variations, changes, and modifications are within the scope of the invention. It is intended in the appended claims to cover all such changes and modifications that fall within the true spirit and scope of the invention.

The invention claimed is:

1. A surgical method, comprising:
    advancing an imager at a distal end of an endoscope through an elongate body until the imager moves out of the elongate body through a front end opening at a distal end of the elongate body;
    positioning the imager at a first position to obtain a first field of view of a surgical site;
    partially withdrawing the endoscope proximally until the imager is adjacent to or proximal of a skive opening through an outermost sidewall of the elongate body;
    re-advancing the endoscope to move the imager through the skive opening and into a second position outside of the elongate body without moving the imager through the distal end of the elongate body, to obtain a second field of view of the surgical site, with the second field of view different from the first field of view.

2. The method of claim 1 further including the imager viewing surrounding environment through the skive opening.

3. The method of claim 1 wherein the imager is entirely outside of the elongate body after moving through the skive opening.

4. The method of claim 1 wherein the imager is distal of the distal end of the elongate body when the imager is in the first position.

5. The method of claim 1 wherein the imager is proximal of the distal end of the elongate body when the imager is in the second position.

6. The method of claim 1 wherein the first field of view is aligned on a first view axis that forms an acute angle with a central axis of the elongate body.

7. The method of claim 1 wherein the second field of view is aligned on a second view axis that forms an acute angle with a central axis of the elongate body.

8. The method of claim 1 wherein the first position is closer to the surgical site than the second position.

9. The method of claim 1 wherein the distal end of the endoscope is free to move in left/right and up/down directions after moving through the skive opening.

10. An endoluminal surgical method, comprising:
    advancing an imager on a front end of an endoscope through an elongate body;
    moving the imager out of a front end of the elongate body and into a first viewing position to provide a first field of view of a surgical site;
    pulling the endoscope back from the front end of the elongate body;
    steering the front end of the endoscope in an at least partially radially outward direction from a central axis of the elongate body;
    advancing the front end of the endoscope through a skive opening in an outermost sidewall of the elongate body, and
    steering the endoscope to move the imager to a second viewing position to provide a second field of view of the surgical site, with the second field of view different from the first field of view.

11. The endoluminal surgical method of claim 10 with first viewing position at a first distance from the surgical site, and the second viewing position at a second distance from the surgical site different from the first distance.

12. The endoluminal surgical method of claim 10 with the first field of view aligned on a first view axis converging with the central axis of the elongate body.

13. The endoluminal surgical method of claim 10 with the second field of view aligned on a second view axis converging with the central axis of the elongate body.

14. The endoluminal surgical method of claim 10 with the first viewing position closer to the central axis of the elongate body than the second viewing position.

15. The endoluminal surgical method of claim 10 with the first viewing position forward of the front end of the elongate body.

16. The endoluminal surgical method of claim 10 with the second viewing position behind the front end of the elongate body.

17. The method of claim 10 wherein the distal end of the endoscope is free to move in left/right and up/down directions after moving through the skive opening.

18. A surgical method comprising:
- advancing an imager at a distal end of an endoscope through an elongate body until the imager moves out of the elongate body through a front end opening at a distal end of the elongate body;
- positioning the imager at a first position to obtain a first field of view of a surgical site;
- partially withdrawing the endoscope proximally until the imager is adjacent to or proximal of a skive opening through an outermost sidewall of the elongate body;
- re-advancing the endoscope to move the imager through the skive opening and into a second position outside of the elongate body without moving the imager through the distal end of the elongate body, to obtain a second field of view of the surgical site, with the second field of view different from the first field of view;
- with the imager, while positioned inside of the elongate body, able to view an environment around the elongate body through the skive opening; and
- wherein the imager is entirely outside of the elongate body after moving through the skive opening, and the distal end of the endoscope is free to move in left/right and up/down directions after moving through the skive opening.

* * * * *